US011440932B2

(12) United States Patent
Falson et al.

(10) Patent No.: US 11,440,932 B2
(45) Date of Patent: Sep. 13, 2022

(54) SURFACTANT COMPOUNDS-CLIPS FOR EXTRACTION AND STABILIZATION IN SOLUTION OF MEMBRANE PROTEINS

(71) Applicants: CENTRE NATIONAL DE LA RECHERCHE SCIENTIFIQUE, Paris (FR); UNIVERSITE CLAUDE BERNARD LYON 1, Villeurbanne (FR); UNIVERSITE GRENOBLE ALPES, Saint-Martin d'Hères (FR)

(72) Inventors: Pierre Falson, Annonay (FR); Julien Dauvergne, Lyons (FR); Ahcène Boumendjel, Meylan (FR); Marine Peuchmaur, Saint-Jean-de-Moirans (FR); Kim Anh Nguyen, Grenoble (FR); Sandrine Magnard, La Valla-en-Gier (FR)

(73) Assignees: CENTRE NATIONAL DE LA RECHERCHE SCIENTIFIQUE, Paris (FR); UNIVERSITE CLAUDE BERNARD LYON 1, Villeurbanne (FR); UNIVERSITE GRENOBLE ALPES, Saint-Martin d'Héres (FR)

( * ) Notice: Subject to any disclaimer, the term of this patent is extended or adjusted under 35 U.S.C. 154(b) by 285 days.

(21) Appl. No.: 16/492,005

(22) PCT Filed: Dec. 27, 2017

(86) PCT No.: PCT/FR2017/053857
§ 371 (c)(1),
(2) Date: Sep. 6, 2019

(87) PCT Pub. No.: WO2018/162806
PCT Pub. Date: Sep. 13, 2018

(65) Prior Publication Data
US 2021/0130385 A1 May 6, 2021

(30) Foreign Application Priority Data
Mar. 9, 2017 (FR) .................................. 1751922

(51) Int. Cl.
*C07H 15/26* (2006.01)
*C07D 249/04* (2006.01)
*C07K 1/14* (2006.01)

(52) U.S. Cl.
CPC ........... *C07H 15/26* (2013.01); *C07D 249/04* (2013.01); *C07K 1/145* (2013.01)

(58) Field of Classification Search
CPC ........ C07H 15/04; C07H 15/14; C07H 15/26; C07K 1/145; C07D 249/04; C07C 237/22; C07C 237/12

USPC ......................................................... 536/17.4
See application file for complete search history.

(56) References Cited

U.S. PATENT DOCUMENTS 6,492,501 B1   12/2002   Popot et al.
2011/0144314 A1   6/2011   Coleman et al.

FOREIGN PATENT DOCUMENTS

JP    200863267 A  *  3/2008  ............... A61K 8/44
WO    WO 98/27434 A1    6/1998
WO    WO 2009/144419 A1    12/2009

OTHER PUBLICATIONS

Barui et al, Molecular Pharmaceutics 2016, 13, 404-419.*
Torrijos et al, Molecules 2012, 17, 11346-11362.*
Chae et al, Nat Methods 2010, 7(12), 1003-1008.*
O'Brien et al, J. Am. Chem. Soc. 2012, 134, 979-987.*
Yeh, J.I. et al, "Peptergents: Peptide Detergents That Improve Stability and Functionality of a Membrane Protein, Glycerol-3-phosphate Dehydrogenase," Biochemistry, American Chemical Society, vol. 44, No. 51, Jan. 1, 2005, pp. 16912-16919, XP008135586.
Matsumoto, K. et al, "Designer Peptide Surfactants Stabilize Functional Photosystem-I Membrane Complex in Aqueous Solution for Extended Time," Journal of Physical Chemistry Part B: Condensed Matter, Materials, Surfaces, Interfaces & Biophysical, vol. 113, No. 1, Jan. 8, 2009, pp. 75-83, XP055410595.
Chae, P.S. et al, "Tandem Facial Amphiphiles for Membrane Protein Stabilization," Journal of the American Chemical Society, vol. 132, No. 47, Nov. 1, 2010, pp. 16750-16752, XP055377702.
Chae, P.S. et al, "Maltose-neopentyl glycol (MNG) amphiphiles for solubilization, stabilization and crystallization of membrane proteins," Nature Methods, vol. 7, No. 12, Oct. 31, 2010, pp. 1003-1008, XP055377701.
International Search Report dated Mar. 8, 2018, in PCT/FR2017/053857 filed on Dec. 27, 2017.

* cited by examiner

*Primary Examiner* — Ganapathy Krishnan
(74) *Attorney, Agent, or Firm* — Oblon, McClelland, Maier & Neustadt, L.L.P.

(57) ABSTRACT

The present invention relates to a compound of formula (I): (I) as defined in the description. The present invention also relates to a method for extracting biological membrane-associated membrane proteins, comprising a step of bringing an aqueous solution of biological membrane-associated membrane proteins into contact with at least one compound of the invention. The present invention also relates to a method for stabilizing membrane proteins in solution in an aqueous solution, comprising a step (i) consisting in bringing an aqueous solution of a membrane protein in solution into contact with at least one compound of the invention.

10 Claims, 11 Drawing Sheets

SURFACTANT COMPOUNDS-CLIPS FOR EXTRACTION AND STABILIZATION IN SOLUTION OF MEMBRANE PROTEINS

TECHNICAL FIELD

The present invention relates to surfactant compounds and the use thereof for extracting and stabilizing in solution membrane proteins extracted in aqueous solution.

The present invention is industrially applicable in the field of biochemistry and also in the medical field, and especially in the field of structure-based drug design.

In the description below, the references between square brackets ([ ]) refer to the reference list presented at the end of the text.

PRIOR ART

The structure of membrane proteins (MPs) is unstable outside the lipid membrane which surrounds them. This is the case when they are extracted from membranes using detergents in order thereafter to purify them and crystallize them or use them as antigens. However, it is vital that this structure is indeed the one adopted by the MP in its original membrane and that it is not more or less altered by the extraction process which is carried out using detergents.

More than a hundred detergents are proposed on the market for extracting MPs. They are excellent competitors for the lipids in which the MPs are embedded and extract said MPs with a high level of effectiveness. This is in part due to the fact that the detergents are exchanged very quickly with the medium, unlike lipids (Israelachvili, J. N., Mitchell, D. J. & Ninham, B. W. Theory of self-assembly of lipid bilayers and vesicles. Biochimica et Biophysics Acta (BBA)—Biomembranes 470, 185-201 (1977) ([1])). However, this high exchange capacity leads to destabilization of the membrane domain of the MPs which, being less well maintained than with lipids, tends to become destructured over time. Thus, an aggregation of the MPs is observed, due to the temporary exposure of the hydrophobic regions of the MPs, which group together to protect each other from the aqueous medium.

In terms of drug design, this is a major challenge for industries which adopt a structure-based drug design approach. Indeed, among the 324 pharmacological targets identified to date, more than 60% are MPs and it is estimated that the number of targets will eventually exceed 3000, 80% of which will be membrane-based (Overington, J. P., Al-Lazikani, B. & Hopkins, A. L. How many drug targets are there? Nat Rev Drug Discov 5, 993-996 (2006) ([2])). This strategy involves knowing the 3D structure of the target, whether apo or associated with its ligand, in order to develop a generation of modulators that are optimized on a structural basis (Mason, J. S., Bortolato, A., Congreve, M. & Marshall, F. H. New insights from structural biology into the drugability of G protein-coupled receptors. Trends in Pharmacological Sciences 33, 249-260 (2012) ([3]); Schaffhausen, J. Advances in structure-based drug design. Trends in Pharmacological Sciences 33, 223 (2012) ([4]); Shoichet, B. K. & Kobilka, B. K. Structure-based drug screening for G-protein-coupled receptors. Trends in Pharmacological Sciences 33, 268-272 (2012) ([5])). For all that, it is necessary to have structural data which actually represent the native state of the protein. This is significantly more limiting when the target is membrane-based, and in this context new tools which remove this limitation have a major impact on this type of approach.

In terms of vaccination, the targets are predominantly accessible at the surface of the pathogens and are therefore anchored or embedded in the plasma membrane. Extracting and maintaining the target MPs, which are sometimes homo- and/or heterooligomeric, in their native state while they are dealt with by the immune system makes it possible to improve the quality of the antibodies, since their effectiveness is directly linked to the structural integrity of the injected proteins. This is also important in terms of the production of antigens which, in the correct conformation, can be injected at a lower dose, enabling an economy of scale.

The design of more stabilizing detergents is a highly active area of research. Thus, among the best stabilizing detergents, lauryl maltose neopentyl glycols (LMNGs), comprising 2 short fatty chains to mimic lipids, have recently been developed (Chae, P. S. et al. Maltose-neopentyl glycol (MNG) amphiphiles for solubilization, stabilization and crystallization of membrane proteins. Nat Meth 7, 1003-1008, (2010) ([6])). Detergents based on bile acids have also been developed (Chae, P. S. et al. Tandem Facial Amphiphiles for Membrane Protein Stabilization. Journal of the American Chemical Society 132, 16750-16752 (2010) ([7]); Zhang, Q. et al. Designing Facial Amphiphiles for the Stabilization of Integral Membrane Proteins. Angewandte Chemie International Edition 46, 7023-7025 (2007) ([8]); Lee, S. C. et al. Steroid-based facial amphiphiles for stabilization and crystallization of membrane proteins. Proceedings of the National Academy of Sciences of the United States of America 110, E1203-1211 (2013) ([9])). The design of these molecules is based on classical concepts such as hydrophilic-hydrophobic balance, which limits their potential. Another generation of detergents incorporating weak acid functions made it possible to increase stability, based on a calix[4]arene skeleton (Suwinska, K. et al. Tri-Anionic Calix[4]arene Monoalkyl Derivatives: Synthesis, Solid-State Structures and Self-Assembly Properties. New Journal of Chemistry 32, 1988-1998, (2008) ([10]); Matar-Merheb, R. et al. Structuring detergents for extracting and stabilizing functional membrane proteins. PLoS One 6, e18036, (2011) ([11])). These acid functions promote the formation of multiple salt bridges with the amino acids located at the membrane-cytoplasm interface in a greater number than elsewhere in the protein (von Heijne, G. The distribution of positively charged residues in bacterial inner membrane proteins correlates with the trans-membrane topology. Embo J 5, 3021-3027 (1986) ([12]); Nilsson, J., Persson, B. & von Heijne, G. Comparative analysis of amino acid distributions in integral membrane proteins from 107 genomes. Proteins: Structure, Function, and Bioinformatics 60, 606-616, (2005) ([13]); von Heijne, G. Membrane-protein topology. Nat Rev Mol Cell Biol 7, 909-918 (2006) ([14])). These calix[4]arene detergents absorb strongly in the UV range, especially at 280 nm at which proteins are most commonly detected, and chelate divalent metals, which may be undesirable.

There is therefore a real need for novel tools that overcome these drawbacks, disadvantages and obstacles of the prior art, in particular novel tools making it possible to extract membrane proteins and to increase the stability thereof in aqueous solution.

DESCRIPTION OF THE INVENTION

Following significant amounts of research, the Applicants have designed novel compounds that make it possible to solve this technical problem.

The compounds of the invention consist of a series of amphiphilic surfactants enabling the extraction of membrane proteins (MPs) while having a low impact on the native and functional state of the MPs.

Advantageously, the compounds of the invention significantly increase the stability of the MPs extracted in aqueous solution.

These molecules have the unique property of encircling the hydrophobic region of the MPs like clips by a triple capacity for interaction: 1/ hydrophobic interaction between the residues of the membrane-bound region of the protein and the fatty chain of the detergents, 2/ interaction of hydrogen bonding type, in particular reinforced by the presence of saccharides or polyether chain, and 3/ ionic interaction between the functions of weak acid type of the polar head of the detergent and the basic residues, the abundance of which is particularly high at the membrane-cytoplasm interface of the MPs.

The molecules of the invention also make it possible to extract and stabilize, in the short and long term (several tens of days), the MPs at 4° C.

These molecules also have the property of not absorbing in the UV range and of not chelating divalent cations.

Thus, a first subject of the invention relates to compounds of formula (I):

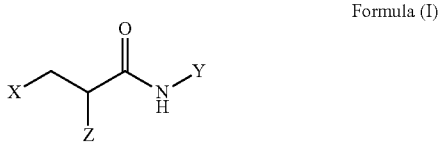

Formula (I)

in which:

X represents —OH,

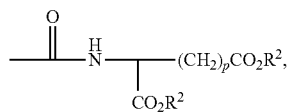

—S(CH$_2$)$_n$CH$_3$,

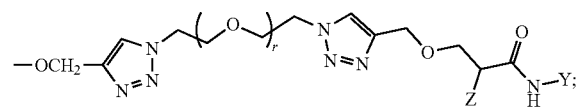

—CO$_2$R$^2$ or

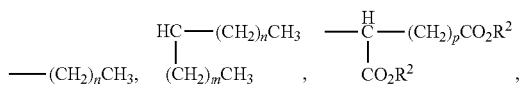

Y represents

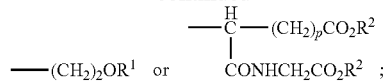

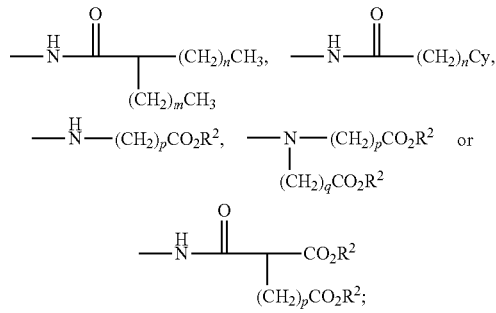

Z represents —NHCO(CH$_2$)$_n$CH$_3$, and in which:

R$^1$ represents a monosaccharide, a disaccharide or polyethylene glycol;
R$^2$ represents H, Na or K;
m is an integer ranging from 4 to 21;
n is an integer ranging from 4 to 21;
p is an integer ranging from 1 to 3;
q is an integer ranging from 1 to 5;
r is an integer ranging from 1 to 10;
Cy represents cyclohexyl;
or a pharmaceutically acceptable salt thereof.

For the purposes of the present invention, "monosaccharide" is intended to mean a carbohydrate monomer comprising from 3 to 14 carbon atoms. This may for example be a monosaccharide chosen from glyceraldehyde, dihydroxyacetone, erythrose, threose, erythrulose, deoxyribose, ribose, arabinose, xylose, lyxose, ribulose, xylulose, allose, altrose, galactose, glucose, gulose, idose, mannose, talose, fructose, psicose, sorbose, tagatose, fucose, rhamnose, sedoheptulose, mannoheptulose, heptahydroxyoctanal, neuraminic acid and sialic acid, and also derivatives thereof. It may preferably be glucose. It may be a cyclic or acylic monosaccharide. Among the cyclic monosaccharides, it may be a monosaccharide of pyranic form or furanic form, for example β-D-glucopyranose.

For the purposes of the present invention, "disaccharide" is intended to mean a disaccharide formed by two carbohydrate monomers via a glycosidic linkage. It may be a homodisaccharide or a heterodisaccharide. If it is a homodisaccharide, it may for example be a homodisaccharide of fructose, such as inulobiose, or of mannose, such as 2alpha-mannobiose or 3alpha-mannobiose, or of glucose, such as trehalose, kojibiose, nigerose, maltose, isomaltose, sophorose, laminaribiose, cellobiose or gentiobiose, or derivatives thereof. It may for example be ethyl maltoside. Alternatively, if it is a heterodisaccharide, it may be a heterodisaccharide of glucose-fructose, for example chosen from trehalulose, sucrose, turanose, maltulose, leucrose, isomaltulose and gentiobiulose, and also derivatives thereof, or else a heterodisaccharide chosen from melibiose, lactulose, lactose and rutinose, and also derivatives thereof.

In the context of the invention, m may be chosen from the integers 4, 5, 6, 7, 8, 9, 10, 11, 12, 13, 14, 15, 16, 17, 18, 19, 20 and 21.

In the context of the invention, n may be chosen from the integers 4, 5, 6, 7, 8, 9, 10, 11, 12, 13, 14, 15, 16, 17, 18, 19, 20 and 21. It may for example be the numbers 10, 12 or 14.

In the context of the invention, p may be chosen from the integers 1, 2 and 3.

In the context of the invention, q may be chosen from the integers 1, 2, 3, 4 and 5.

In the context of the invention, r may be chosen from the integers 1, 2, 3, 4, 5, 6, 7, 8, 9 and 10.

The integers m, n, p, q and r are independent of one another and all the combinations of these integers belong to the invention.

In the context of the present invention, the term "pharmaceutically acceptable salts" comprises non-toxic salts prepared with acids or bases depending on the substituents present on the compounds. When the compounds of the invention comprise acid functions, the corresponding salts can be obtained by adding an organic or inorganic base to the compound in neutralized form, optionally in the presence of a preferably inert solvent. Examples of addition salts of a base can be the sodium, potassium, calcium, ammonium, (organic) amino or magnesium salts.

Thus, the invention is for example a compound of formula (I), in which:

X represents

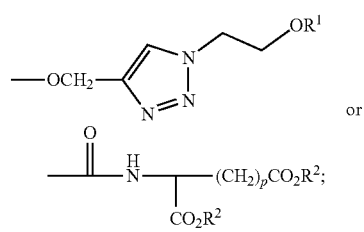

Y represents

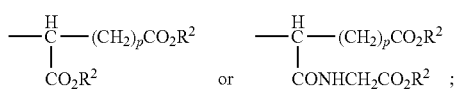

Z represents —NHCO(CH$_2$)$_n$CH$_3$ or

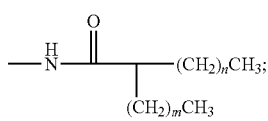

R$^1$ represents a monosaccharide, for example glucose, a disaccharide, for example maltose, or polyethylene glycol;

R$^2$ represents H, Na or K;

m is an integer ranging from 4 to 21, for example equal to 11;

n is an integer ranging from 4 to 21, for example equal to 8, 10, 11, 12, 14 or 17;

p is an integer equal to 1 to 3, for example equal to 2; or a pharmaceutically acceptable salt thereof.

In this case, it may for example be compounds of the group 3.7, for example 3.7b, 3.7c, 3.7e, 3.7g, 3.7j, 3.7l, or of the group 4.6, for example 4.6b or 4.6d, as described in the "Examples" section below.

Alternatively, the invention is for example a compound of formula (I), in which:

X represents —S(CH$_2$)$_n$CH$_3$;

Y represents —(CH$_2$)$_2$OR$^1$;

Z represents

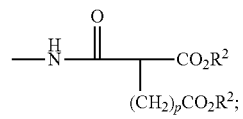

R$^1$ represents a monosaccharide, a disaccharide, for example maltose, or polyethylene glycol;

R$^2$ represents H, Na or K;

n is an integer ranging from 4 to 21, for example equal to 11, 13, 15 or 17;

p is an integer equal to 1 to 3, for example equal to 2; or a pharmaceutically acceptable salt thereof.

In this case, it may for example be compounds of the group 5.3, for example 5.3a, b, c or d, and in particular compound 5.3a, as described in the "Examples" section below.

Generally speaking, each of the compounds corresponding to formula (I) and described in the "Examples" section and in particular in tables 1 and 2 of the "Examples" section are molecules forming the subject of the invention.

Advantageously, the molecules of the present invention do not absorb, or only negligibly absorb, at from 220 to 500 nm (and beyond) and therefore do not prevent the detection of proteins at 280 nm.

Advantageously, the molecules of the invention do not form an insoluble complex with divalent metals. This absence of interaction with metals is for example very useful during steps of metal affinity-type chromatography, which use nickel or cobalt and which cannot be implemented with high concentrations of conventional detergents, unlike the molecules of the invention. It is also very useful for avoiding the precipitation of complexes in the presence of calcium and magnesium, which are protein cofactors commonly encountered in living organisms.

The inventors have demonstrated experimentally that it is possible to vary the CMC (critical micelle concentration) of the compounds of the invention by varying their substituents, for example by varying the length of the aliphatic chain and/or the size of the polar heads, as a function of the intended purpose, for example easily eliminating, by dialysis or ultrafiltration, a detergent with a high CMC or else retaining said detergent by using compounds with a lower CMC.

The inventors have demonstrated experimentally that it is possible to carry out selective extractions, as a function of the membrane proteins to be extracted, using the molecules of the invention, by varying the technical characteristics thereof, especially their substituents, in particular when membrane proteins of interest are generally co-purified with a contaminant using conventional techniques.

Advantageously, the extraction of membrane proteins by means of the molecules of the invention does not cause a reduction in the functional activity of the MPs once they are extracted. Optionally, the extraction by means of the molecules of the invention may enable an increase in the functional activity of the extracted MP, depending on the nature of the MP to be extracted.

The inventors have also demonstrated experimentally that the molecules of the invention stabilize in solution membrane proteins for at least twice as long, for example twice, three times, four times, five times or even more, than a conventional detergent.

The compounds of the invention can be prepared by means of any suitable method known to those skilled in the art, including at least one of the methods including peptide coupling, deprotection of the Fmoc (fluorenylmethoxycarbonyl) group, amide formation, catalytic hydrogenation, deprotection of the tBu (tert-butyl) group, deprotection of methyl or ethyl esters, deprotection of Boc groups, Huisgen cycloaddition, deacetylation reaction, formation of (Na, K) carboxylate salts, and trityl deprotection and thiol-ene coupling. Protocols for synthesis of each of the compounds of the invention are described for example in the "Examples" section below.

A second subject of the invention relates to a process for extracting membrane proteins associated with a biological membrane, comprising a step of bringing an aqueous solution of membrane proteins associated with the biological membrane into contact with at least one compound of formula (I) as defined above.

For the purposes of the present invention, "biological membrane" is intended to mean any assembly of lipophilic molecules into a double leaflet separating a cell from its environment, composed of a bilayer of amphiphilic lipids, especially phospholipids, each membrane lipid being formed of a hydrophilic polar head oriented towards the outside of the membrane and a hydrophobic tail oriented towards the inside. This may be a membrane of a prokaryotic cell or eukaryotic, animal cell—with the exception of human embryonic stem cells—or plant cell, or a virus. If it is a eukaryotic cell, it may for example be a plasma membrane, an intracellular membrane such as a nuclear membrane, a lysosome, an exosome, a proteoliposome, a smooth or rough endoplasmic reticulum membrane, or a Golgi apparatus membrane, this list being non-limiting. It may also be an isolated transgenic host cell originating from a cell line in which one or more antigens of interest are expressed, for example by techniques of genetic engineering of recombinant RNA or DNA or by infecting a cell with a viral vector expressing one or more vaccine antigens of interest. Any genetic engineering technique known to those skilled in the art, enabling expression of a transgene in a cell, may be used. It may be a technique involving expression of a DNA or an RNA, for example a synthetic coding mRNA, introduced into a cell by transduction, for example by electroporation, microinjection, ultrasound, infection or transfection. The expression may for example be transient and/or inducible and/or constitutive of at least one antigen of interest, as described for example in document WO02090533 ([29]). The cell may further be any isolated cell, especially with the exception of human embryonic stem cells, for example an isolated human cell—human embryonic stems cells being for example excluded—or an isolated animal—non-human—or plant cell. The isolated cell may originate from a cell line chosen from Vero (ATCC No. CCL-81) such as Vero 76 (ATCC No. CRL-1587), CHO such as CHO—KI (CCL 61, ATCC), BHK such as BHK-21 [C-13] (ATCC® CCL-10™), HELA, perC6® (Crucell), HEK293 (ATCC® CRL-1573™), Sf9 (ATCC, CRL-1711), MDCK, for example MDCK (NBL-2) (ATCC® CCL-34™), this list being non-limiting.

The biological membrane may be whole, that is to say intact, or be a biological membrane fraction, that is to say a portion of a biological membrane.

For the purposes of the present invention, "membrane protein" is intended to mean a protein associated with biological membranes, that is to say either anchored or integral, and not free to diffuse in aqueous media. Among the protein membranes, mention may for example be made of plasma membrane proteins and intracellular membrane proteins, for example mitochondrial, nuclear or lysosomal membrane proteins. It may for example be a transport protein, for example an ABC transporter, optionally selected from the group comprising P-glycoproteins (Pgp/ABCB1), MRP1/ABCC1, MRP2/ABCC2, BCRP/ABCG2 and BmrA. Alternatively, it may be a protein of interest expressed transgenically in a biological membrane, for example the proteins mentioned above and expressed in eukaryotic cells, as described by Baiceanu et al. (Baiceanu E et al: "2-Indolylmethylenebenzofuranones as first effective inhibitors of ABCC2", Eur J Med Chem. 2016 Oct. 21; 122:408-18 ([30])) for ABCB1, C1, C2 and G2, or BmrA expressed in bacteria (Matar-Merheb, R. et al. ([11])).

The biological membrane may be brought into contact with at least one compound of formula (I) as defined above, or at least two, or at least three of these compounds, or even more. Advantageously, the selection of a plurality of one or a plurality of compound(s) of the invention may enable the selective extraction of a membrane protein, for example in order to do away with contaminants.

In the context of the invention, the biological membrane may be placed in aqueous solution beforehand, for example in a buffer solution.

The step of bringing an aqueous solution comprising the membrane protein to be extracted into contact with at least one compound of formula (I) may be carried out at a pH at which the carboxylic groups of the molecules of the invention are ionized, in order to maximize the clip effect of the molecules. Advantageously, the pH is a pH of between 5.0 and 12, for example a pH of 5.0, or 6.0, or 7.0, or 8.0, or 9.0, or 10.0, or 11.0, or 12.0.

The extraction process according to the invention may further comprise a step of incubating the membrane protein and the compound of the invention. The incubation time can be adapted such that all or a portion of the membrane proteins to be extracted are in solution. The incubation time can be determined by those skilled in the art, who will know how to adapt it as a function of the membrane to be solubilized and/or the protein to be extracted and/or the desired extraction yield. The incubation time may for example be 15 minutes, or 30 minutes, or 1 hour, or 2 hours, or 3 hours, or even greater than 3 hours.

The incubation step may be carried out at a temperature suited to the protein to be extracted, especially so as to avoid denaturation thereof, especially by heat. The temperature may be consequently adapted by those skilled in the art; typically, for proteins that are not thermostable, it may be between 4 and 40° C. and for thermostable proteins 40-90° C.

The extraction process of the invention may further comprise a separation step, in order to obtain the fraction containing the desired protein. This may be any method known to those skilled in the art, for example centrifugation. At the end of the separation step, a fraction containing the protein extracted from the membrane is obtained.

Advantageously, at the end of the extraction, the protein may be retained in a solution comprising at least one compound of the invention. Advantageously, the compounds of the invention enable the functional stabilization of the proteins, especially after the latter have been extracted from their membrane.

Another subject of the invention thus relates to a process for stabilizing membrane proteins in solution, that is to say therefore outside of the biological membrane in which they were initially located, in an aqueous solution, comprising a step (i) consisting in bringing an aqueous solution of a membrane protein in solution into contact with at least one compound of formula (I) of the invention.

The stabilization of the protein may be a conservation of all or some of the functional properties thereof compared to the native state thereof. This may be a conservation of at least 50% of the activity of the protein compared to the native state thereof, or at least 60%, or at least 70%, or at least 80%, or at least 90%, or 100% of this activity.

Advantageously, the protein is thus stabilized at a temperature of from 0° C. to 10° C., for a duration of greater than 1 day, for example greater than 5 days, or greater than 10 days, or greater than 20 days, or greater than 30 days, or greater than 40 days.

The membrane proteins may have been placed in solution by a step of extraction by means of a compound of the invention as defined previously, or by means of a step of extraction by another detergent, that is to say a commercial detergent, for example DDM (n-dodecyl β-d-maltoside), LMNG (lauryl maltose neopentyl glycol), Triton X100 or FA3 (facial amphiphile 3).

Other advantages may yet become apparent to those skilled in the art on reading the examples below, illustrated by the appended figures, given by way of illustration.

BRIEF DESCRIPTION OF THE FIGURES

FIG. 8 depicts the extraction of BmrA tested at different concentrations (expressed in mM and in ×CMC) of different detergents (DDM, LMNG and FA3) and of molecules of the invention (3.7b, 3.7c, 3.7d, 3.7e, 3.7f, 3.7h, 3.7g, 3.7j, 3.7l, 3.9a, 4.3d, 5.3b) as indicated in FIG. 7. The total (T) and soluble (S) fractions of the solutions prepared in FIG. 7 are deposited on 10% SDS-PAGE after separation by centrifugation at 100 000×g for 30 min, 4° C. DDM=β-D-dodecyl maltoside; LMNG: lauryl maltose neopentyl glycol (Chae, P. S. et al. ([6])). FA3=facial amphiphile #3 (Lee, S. C. et al. ([9])).

EXAMPLES

Figure 1:
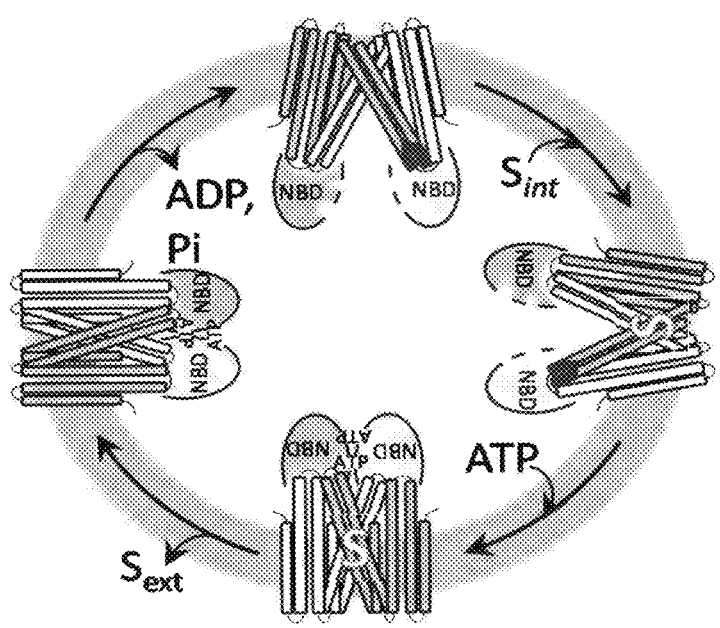
FIG. 1 depicts the topology of the ABC transporter BmrA and the cycle of transport of substrates through the plasma membrane. S=substrate; NBD=nucleotide-binding domain; ATP=adenosine triphosphate.

Example 1: Processes for Preparing the Compounds of the Invention

The different examples of the detergents belonging to formula (I) are prepared according to the following protocols:

General Protocol A: Peptide Coupling

According to Corzana et al., 2006 (Corzana, F. et al. New Insights into α-GalNAc-Ser Motif: Influence of Hydrogen Bonding versus Solvent Interactions on the Preferred Conformation. *Journal of the American Chemical Society* 128, 14640-14648 (2006) ([15])). The amino acid having a free amine function or in the form of tosylate salt (2 equiv.), DIEA (5 equiv.) and TBTU (1.2 equiv.) are added to a solution of amino acid derivative having a free carboxylic acid function (1 equiv.) in anhydrous DMF (15 ml/mmol). The reaction mixture is stirred under inert atmosphere at room temperature (RT) for 3 h. After adding water (15 ml/mmol), the reaction medium is extracted with ethyl ether. The organic phases are combined, washed with distilled water and a saturated aqueous NaCl solution, dried over MgSO$_4$, filtered then concentrated under vacuum. The crude product is purified by silica gel column chromatography.

General Protocol B1: Deprotection of the Fmoc Group

Diethylamine (20 equiv.) is added to a solution of amine protected in the form of Fmoc (1 equiv.) in anhydrous CH$_2$Cl$_2$ (20 ml/mmol). After stirring overnight at RT and under N$_2$, the reaction medium is concentrated under vacuum. The residue is taken up in CH$_2$Cl$_2$. This solution is washed with a saturated solution of NaHCO$_3$, dried over K$_2$CO$_3$, then concentrated under vacuum.

General Protocol B2: Deprotection of the Fmoc Group

Protocol identical to B1, except the diethylamine is replaced with piperidine.

General Protocol C: Amide Formation

An acid chloride (2 equiv.), DMAP (0.5 equiv.) and pyridine (34 equiv.) are added to a solution of deprotected amine (1 equiv.) in anhydrous $CH_2Cl_2$ (30 ml/mmol). After stirring overnight at RT and under $N_2$, the reaction medium is acidified (pH=3) by addition of an aqueous solution of 10% HCl. The reaction medium is extracted with $CH_2Cl_2$. The organic phases are combined, washed with a saturated aqueous NaCl solution, dried over $MgSO_4$, filtered then concentrated under vacuum. The crude product is purified by silica gel column chromatography.

General Protocol D1: Catalytic Hydrogenation

10% Pd/C (200 mg/mmol) is added to a solution of benzyl ester (1 equiv.) in MeOH (100 ml/mmol). After 4 hours to one night of stirring under $H_2$ at RT, the reaction medium is filtered over Celite® then concentrated under vacuum. The crude product obtained is directly used in the following step without purification. In the case of PEGylated detergents, the residue is washed with cyclohexane and/or $CH_2Cl_2$.

General Protocol D2: Catalytic Hydrogenation

5% Pd/C (120 mg/mmol) is added to a solution of benzyl ester (1 equiv.) in THF (30 ml/mmol). After stirring overnight under $H_2$ at RT, the reaction medium is filtered over Celite® then concentrated under vacuum. The crude product obtained is directly used in the following step without purification.

General Protocol E: Deprotection of the Tert-Butyl (tBu) Group

According to Christensen et al., 2005 (Christensen, C. A. & Meldal, M. Efficient solid-phase synthesis of peptide-based phosphine ligands: towards combinatorial libraries of selective transition metal catalysts. *Chemistry* 11, 4121-4131, doi:10.1002/chem.200500105 (2005) ([16])). Trifluoroacetic acid TFA (4 ml/mmol) is added at 0° C. to a solution of alcohol protected in the form of t-butyl ether (1 equiv.) in $CH_2Cl_2$ (12 ml/mmol). After stirring overnight at RT and under $N_2$, the reaction medium is concentrated under vacuum. The residue is taken up in $CH_2Cl_2$ then a 2 M aqueous solution of NaOH is added (pH=11-12). The aqueous phase is washed with EtOAc then acidified with a concentrated solution of HCl (pH=1-2) before being extracted with EtOAc. The organic phases are combined, dried over $MgSO_4$, filtered and concentrated under vacuum. The residue is washed with $CH_2Cl_2$ to eliminate the remaining fatty acid.

General Protocol F: Deprotection of Methyl or Ethyl Esters

A solution of LiOH (5 equiv.) in water (10.4 ml/mmol) is added to a solution of acid protected in the form of methyl or ethyl ester (1 equiv.) in THF (10.4 ml/mmol). The reaction medium is stirred for 4 h at RT. After adding an aqueous solution of $H_3PO_4$ 5% (pH=1-2), the reaction medium is extracted with EtOAc (unless the desired compound precipitates; in this case, it is washed with distilled water, cooled beforehand). The organic phases are combined, washed with a saturated aqueous NaCl solution, dried over $MgSO_4$, filtered then concentrated under vacuum. The crude product is subsequently purified by C18 reversed-phase column chromatography (eluent: $H_2O$ then MeOH).

General Protocol G: Deprotection of the Boc Groups

TFA (2.5 ml/g) is added at 0° C. to a solution of amine protected by a Boc group (1 equiv.) in anhydrous $CH_2Cl_2$ (5 ml/g). After 4-5 h of stirring at RT under $N_2$, the reaction medium is concentrated under vacuum. The residue is taken up in $CH_2Cl_2$ and an aqueous solution of NaOH (2 M) is added (pH=11-12). The aqueous phase is washed with EtOAc, acidified with a concentrated solution of HCl (pH=1-2), washed with $CH_2Cl_2$ then extracted with EtOAc. The organic phases are combined, dried over $MgSO_4$, filtered then concentrated under vacuum. The crude product obtained is directly used in the following step without purification.

General Protocol I: Huisgen Cycloaddition

According to Munteanu et al., 2008 (Munteanu, M., Choi, S. & Ritter, H. Cyclodextrin Methacrylate via Microwave-Assisted Click Reaction. *Macromolecules* 41, 9619-9623 (2008) ([18])). A few drops of water are added to a solution of alkyne (1 equiv.), of azidosaccharide protected in the form of acetate or azido-PEG (1-1.5 equiv.), of $CuSO_4.5H_2O$ (0.1 equiv.) and of sodium ascorbate (0.2 equiv.) in DMF (6 ml/mmol). The reaction mixture is stirred under microwave irradiation at 140° C. for 1 h. After adding water, the reaction medium is extracted with EtOAc. The organic phases are combined, dried over $MgSO_4$, filtered then concentrated under vacuum. The crude product is purified by silica gel column chromatography.

General Protocol J: Deacetylation Reaction

According to Chae, P. S. et al., 2010 ([6]). MeONa (0.2 equiv.) is added to a solution of saccharide derivative protected in the form of acetate (1 equiv.) in MeOH (16.7 ml/mmol). After stirring overnight at RT, the proton exchange resin (Dowex-H⁺) is added and the reaction medium is stirred for 30 min before being filtered. The filtrate is concentrated under vacuum and the crude product obtained is used directly in the following step without purification.

General Protocol K: Formation of (Na, K) Carboxylate Salts

MeONa or MeOK (1 equiv. per carboxylate function to be salified) is added to a solution of carboxylic acid (1 equiv.) in a minimal amount of MeOH. After 5 min of stirring, the solvent is evaporated and the final product is recovered in solid form.

General Protocol L: Trityl Deprotection and Thiol-Ene Coupling

TFA (5 ml/g) is added at 0° C. to a suspension of L-Fmoc-Cys(Trt)-OH (1 equiv.) in $CH_2Cl_2$ (10 ml/g) in the presence of $Et_3SiH$ (1.5 equiv.). After 3 h of stirring, the reaction medium is concentrated under vacuum to give a gray solid. This residue, the alkene (1.2 equiv.) and the DMPA photoinitiator (0.5 equiv.) are dissolved in THF (7.5 ml/g). The medium is stirred for 3 h at RT and under UV. After concentration under vacuum, the crude product is purified by silica gel column chromatography.

Example 2: Example of Compounds 1.1 to 1.5

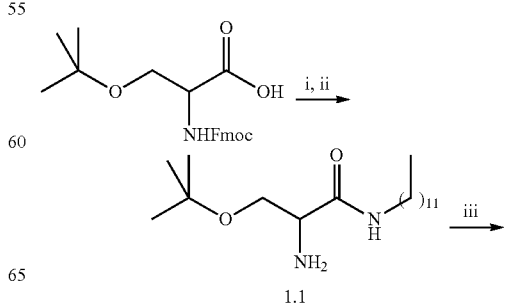

-continued

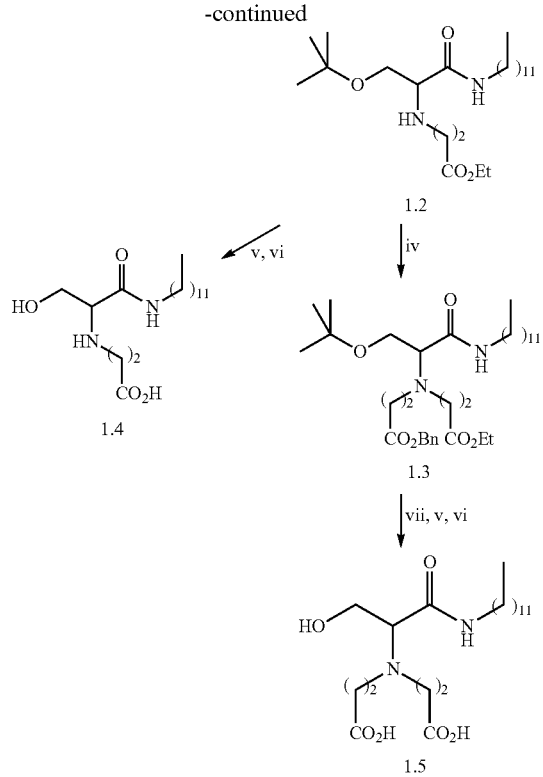

i. CH$_3$(CH$_2$)$_{11}$NH$_2$, TBTU, DIEA, DMF;
ii. Piperidine/DMF 20:80;
iii. Ethyl acrylate, MeOH;
iv. Benzyl acrylate, 70° C.;
v. LiOH, THF, H$_2$O, RT;
vi. TFA, CH$_2$Cl$_2$, RT;
vii. H$_2$, Pd/C 10%, MeOH.

Compound 1.1

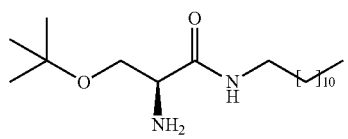

Dodecylamine (2.9 g, 15.64 mmol, 2 equiv.) then DIEA (6.8 ml, 39.11 mmol, 5 equiv.) and TBTU (3.01 g, 9.38 mmol, 1.2 equiv.) are added to a solution of Fmoc-Ser(tBu)-OH (3.0 g, 7.82 mmol, 1 equiv.) in DMF (300 ml). After 4 h of stirring at RT, the reaction medium is concentrated under vacuum and diluted with ether. The organic phase is washed successively with a saturated solution of NaCl, a solution of HCl (0.1 N) then with a solution of NaHCO$_3$ (5%) before being dried over Na$_2$SO$_4$, filtered and concentrated under vacuum. The residue obtained is taken up in a mixture of piperidine/DMF (20:80, 300 ml). After 1 h of stirring at RT, the reaction medium is subsequently concentrated under vacuum. The crude product obtained is purified by silica gel column chromatography (CH$_2$Cl$_2$/MeOH 98:2) to give the expected compound (2.44 g, 7.43 mmol, 95%) in the form of a yellow oil. Rf=0.45 (0H$_2$Cl$_2$/MeOH 95:5); $^1$H NMR (400 MHz, CDCl$_3$) δ ppm 0.89 (t, J=7.2 Hz, 3H), 1.20 (s, 9H), 1.26-1.35 (m, 22H), 3.25 (q, J=4.4 Hz, 2H), 3.42-3.51 (m, 2H), 3.62 (dd, J=4.0, 4.0 Hz, 1H), 7.39 (m, 1H); $^1$H NMR (400 MHz, CDCl$_3$) δ ppm 14.4 (CH$_3$), 23.0 (CH$_2$), 27.3 (CH$_2$), 27.8 (3×CH$_3$), 29.6 (2×CH$_2$), 29.9 (3×CH$_2$), 30.0 (CH$_2$), 32.0 (CH$_2$), 36.8 (CH$_2$), 39.4 (CH$_2$), 55.7 (CH), 64.3 (CH$_2$), 73.7 (C), 173.2 (C); Mass (ESI+): m/z (%) 329 [M+H]$^+$ (100).

Compound 1.2

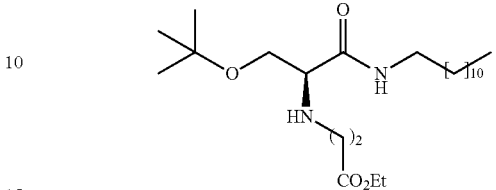

Ethyl acrylate (1.37 ml, 12.9 mmol, 2.5 equiv.) was added to a solution of intermediate 1.1 (1.06 g, 3.22 mmol, 1 equiv.) in methanol (3.5 ml). The mixture was flushed with nitrogen, covered with aluminum foil and stirred for 5 days at RT. The crude product obtained is purified by silica gel column chromatography (CH$_2$Cl$_2$/MeOH 95:5) to give the expected compound (1.24 g, 2.90 mmol, 83%) in the form of a yellow oil. Rf=0.56 (CH$_2$Cl$_2$/MeOH 98:2); $^1$H NMR (400 MHz, CDCl$_3$) δ ppm 0.89 (t, J=6.8 Hz, 3H), 1.13 (s, 9H), 1.22-1.25 (m, 25H), 1.46-1.49 (m, 2H), 2.04 (m, 1H), 2.44 (t, J=6.0 Hz, 2H), 2.79-2.83 (m, 2H), 3.16 (dd, J=4.0, 4.0 Hz, 1H), 3.20 (q, J=6.8 Hz, 2H), 3.29 (t, J=4.8 Hz, 1H), 3.62 (dd, J=4.0, 4.0 Hz, 1H), 4.12 (q, J=7.2 Hz, 2H), 7.46 (t, J=4.8 Hz, 1H); $^{13}$C NMR (400 MHz, CDCl$_3$) δ ppm 14.3 (CH$_3$), 14.4 (CH$_3$), 22.8 (CH$_2$), 27.1 (CH$_2$), 27.7 (3×CH$_3$), 29.5-29.8 (7×CH$_2$), 32.1 (CH$_2$), 35.0 (CH$_2$), 39.2 (CH$_2$), 44.0 (CH$_2$), 60.7 (CH$_2$), 62.6 (CH), 63.5 (CH$_2$), 73.5 (C), 172.0 (C), 172.7 (C); Mass (ESI+): m/z (%) 429 [M+H]$^+$ (100); HRMS (ESI+) m/z calculated for C$_{24}$H$_{49}$N$_2$O$_4$ 429.3692, found 429.3696.

Compound 1.3

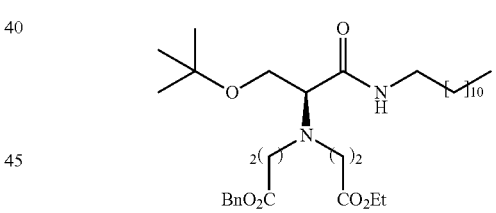

A solution of intermediate 1.2 (1.40 g, 3.26 mmol, 1 equiv) and benzyl acrylate (1.32 g, 8.16 mmol, 2.5 equiv.) is stirred at 70° C. for 7 days then the reaction medium is concentrated under vacuum. The crude product obtained is purified by silica gel column chromatography (CH$_2$Cl$_2$ 100%) to give the expected compound (640 mg, 1.07 mmol, 33%) in the form of a yellow oil. Rf=0.47 (CH$_2$Cl$_2$/MeOH 98:2); $^1$H NMR (400 MHz, CDCl$_3$) δ ppm 0.80 (t, J=6.8 Hz, 3H), 1.10 (s, 9H), 1.13-1.25 (m, 22H), 1.40 (m, 2H), 2.30-2.52 (m, 4H), 2.87-3.04 (m, 4H), 3.09 (q, J=6.4 Hz, 2H), 3.38 (dd, J=8.8, 4.4 Hz, 1H), 3.57 (ddd, J=19.2, 12.8, 3.2 Hz, 1H), 3.89 (dd, J=6.0, 2.4 Hz, 1H), 4.04 (q, J=7.2 Hz, 2H), 5.04 (s, 2H), 7.23-7.33 (m, 5H), 7.51 (t, J=6.0 Hz, 1H), $^{13}$C NMR (400 MHz, CDCl$_3$) δ ppm 14.1 (CH$_3$), 14.2 (CH$_3$), 22.7 (CH$_2$), 27.0 (CH$_2$), 27.5 (3×CH$_3$), 29.4-29.7 (7×CH$_2$), 31.9 (2×CH$_2$), 33.5 (CH$_2$), 39.2 (CH$_2$), 47.0 (2×CH$_2$), 60.0 (CH$_2$), 60.4 (CH$_2$), 65.1 (CH), 66.3 (CH$_2$), 73.3 (C), 128.3-128.6 (5×CH), 136.3 (C), 171.6 (C), 172.4 (C), 172.5 (C); Mass (ESI+) m/z (%) 613 (46) [M+Na]$^+$, 591

(100) [M+H]+; HRMS (ESI+) m/z calculated for C34H59N2O6 591.4373, found 591.4384.

Compound 1.4

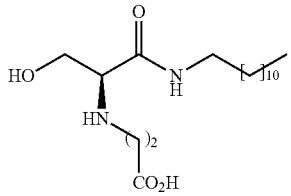

The compound 1.4 (yellow oil, 17 mg, 0.05 mmol, 38%) was obtained from the compound 1.2 (59 mg, 0.13 mmol) by following the general protocols F then K (however without carrying out the acid-base washes); $^1$H NMR (400 MHz, MeOD) δ ppm 0.64 (t, J=8.0 Hz, 3H), 1.06-1.07 (m, 18H), 1.27-1.31 (m, 2H), 2.55 (t, J=8.0 Hz, 2H), 3.00 (t, J=8.0 Hz, 2H), 3.04-3.05 (m, 2H), 3.60 (dd, J=8.0, 8.0 Hz, 1H), 3.69-3.77 (m, 2H); $^{13}$C NMR (100 MHz, MeOD) δ ppm 14.3 (CH$_3$), 23.6 (CH$_2$), 27.4 (CH$_2$), 27.8 (CH$_2$), 30.1 (CH$_2$), 30.2 (CH$_2$), 30.3 (CH$_2$), 30.5 (CH$_2$), 30.6 (3×CH$_2$), 32.9 (CH$_2$), 40.8 (CH$_2$), 43.5 (CH$_2$), 60.4 (CH), 60.9 (CH$_2$), 167.0 (2×C); mass (ESI+) m/z (%) 345 (100) [M+H]+; HRMS (ESI+) m/z calculated for C$_{18}$H$_{37}$N$_2$O$_4$ 345.2747, found 345.2746.

Compound 1.5

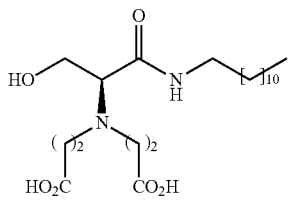

The compound 1.5 (yellow oil, 147 mg, 0.35 mmol, 72%) was obtained from the compound 1.3 (300 mg, 0.50 mmol) by following the general protocols D1, F then K (without however carrying out the acid-base washes); $^1$H NMR (400 MHz, MeOD) δ ppm 0.90 (t, 3H, J=8.0 Hz), 1.22-1.37 (m, 22H), 1.53-1.57 (m, 2H), 2.90 (t, J=8.0 Hz, 4H), 3.18-3.29 (m, 3H), 3.64 (m, J=8.0 Hz, 4H), 4.08 (t, J=4.0 Hz, 1H), 4.16-4.18 (m, 1H), 8.42 (t, J=4.0 Hz, NH); $^{13}$C NMR (100 MHz, MeOD) δ ppm 14.5 (CH$_3$), 17.9 (CH$_2$), 23.8 (CH$_2$), 24.3 (CH$_2$), 28.1 (CH$_2$), 29.8 (CH$_2$), 30.2 (CH$_2$), 30.5 (CH$_2$), 30.6 (CH$_2$), 30.8 (2×CH$_2$), 33.2 (2×CH$_2$), 41.0 (CH$_2$), 54.9 (2×CH$_2$), 59.4 (CH), 69.2 (CH$_2$), 173.8 (3×C); mass (ESI+) m/z (%) 417 (100) [M+H]+; HRMS (ESI+) m/z calculated for C$_{21}$H$_{41}$N$_2$O$_6$ 417.2959, found 417.2956.

Example 3: Compounds 2.1 to 2.3

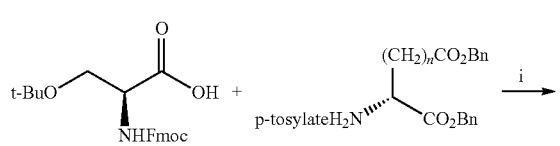

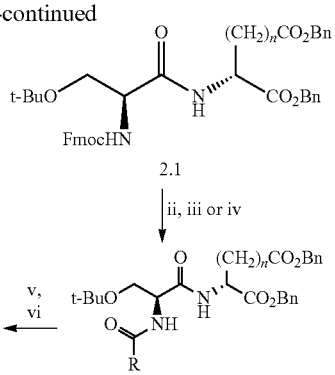

i. TBTU, DIEA, DMF;
ii. Et$_2$NH, CH$_2$Cl$_2$
iii. RCOCl, DMAP, pyridine, CH$_2$Cl$_2$;
iv. RCOOH, TBTU, DIEA, DMF;
v. H$_2$, Pd/C, MeOH;
vi. TFA, CH$_2$Cl$_2$.

Example 2.1a

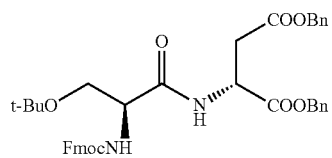

The compound 2.1a (white solid, 2.95 g, 4.34 mmol, 83%) was obtained from the commercial compounds Fmoc-L-Ser(t-Bu)-OH (2.00 g, 5.22 mmol) and H-D-Asp(OBn)-OBn.p-tosylate (5.07 g, 10.43 mmol) by following the general protocol A (purification: silica gel column chromatography, element: cyclohexane/EtOAc 9:1 to 7:3).

Rf=0.32 (cyclohexane/EtOAc 7:3); Tm=115-117° C.; $^1$H NMR (400 MHz, CDCl$_3$) δ ppm 1.15 (s, 9H), 2.82-2.96 (m, 1H), 3.06 (dd, J=17.1, 4.6 Hz, 1H), 3.38 (dd, J=8.3, 8.3 Hz, 1H), 3.74-3.77 (m, 1H), 4.19-4.26 (m, 2H), 4.35-4.37 (m, 2H), 4.88-4.93 (m, 1H), 5.01 (s, 2H), 5.12 (s, 2H), 5.74 (d, J=3.6 Hz, 1H), 7.25-7.34 (m, 12H, H3"), 7.38 (dd, J=7.5, 7.5 Hz, 2H), 7.59-7.61 (m, 2H), 7.65 (d, J=6.3 Hz, 1H), 7.74 (d, J=7.5 Hz, 2H); $^{13}$C NMR (100 MHz, CDCl$_3$) δ ppm 27.5 (3×CH$_3$), 36.6 (CH$_2$), 47.3 (CH), 49.0 (CH), 54.8 (CH), 61.7 (CH$_2$), 66.9 (CH$_2$), 67.3 (CH$_2$), 67.7 (CH$_2$), 74.4 (C), 120.1 (2×CH), 125.3 (2×CH), 127.3 (2×CH), 127.9 (2×CH), 128.4 (CH), 128.5 (CH), 128.6 (CH), 128.6 (CH), 128.7 (CH), 135.3 (C), 135.5 (C), 141.5 (2×C), 143.9 (2×C), 156.2 (C), 170.3 (2×C), 170.6 (C); Mass (ESI+) m/z (%) 426 (100), 701 (60) [M+Na]+; HRMS (ESI+) m/z calculated for C$_{40}$H$_{43}$N$_2$O$_8$ 679.3019, found 679.3013.

Example 2.1b

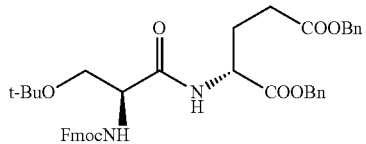

The compound 2.1b (white solid, 5.14 g, 7.42 mmol, 81%) was obtained from the commercial compounds Fmoc-L-Ser(t-Bu)-OH (3.5 g, 9.12 mmol) and H-D-Glu(OBn)-OBn.p-tosylate (9 g, 18.24 mmol) by following the general protocol A (modification: after adding water, the desired compound precipitates and was purified by recrystallization in a CH$_2$Cl$_2$/Et$_2$O mixture).

Rf=0.50 (cyclohexane/EtOAc 7:3); Tm=126-128° C.; $^1$H NMR (400 MHz, CDCl$_3$) δ ppm 1.19 (s, 9H), 1.99-2.11 (m, 1H), 2.22-2.35 (m, 1H), 2.32-2.55 (m, 2H), 3.41 (dd, J=8.3, 8.3 Hz, 1H), 3.75-3.87 (m, 1H), 4.23 (t, J=7.1 Hz, 1H), 4.24-4.33 (m, 1H), 4.40 (d, J=6.8 Hz, 2H), 4.68-4.76 (m, 1H), 5.09 (s, 2H), 5.17 (s, 2H), 5.78 (bs, 1H), 7.21-7.46 (m, 15H), 7.61 (d, J=7.0 Hz, 2H), 7.76 (d, J=7.5 Hz, 2H); $^{13}$C NMR (100 MHz, CDCl$_3$) δ ppm 27.4 (3×CH$_3$), 27.5 (CH$_2$), 30.0 (CH$_2$), 47.1 (CH), 51.8 (CH), 54.6 (CH), 61.7 (CH$_2$), 66.5 (CH$_2$), 67.2 (CH$_2$), 67.4 (CH$_2$), 74.3 (C), 120.0 (2×CH), 125.1 (2×CH), 127.1 (2×CH), 127.7 (2×CH), 128.2-128.7 (10×CH), 135.1 (C), 135.7 (C), 141.3 (2×C), 143.7 (2×C), 156.1 (C), 170.1 (C), 171.2 (C), 172.3 (C); Mass (ESI+) m/z (%) 426 (100), 570 (3), 715 (1) [M+Na]$^+$; HRMS (ESI+) m/z calculated for C$_{41}$H$_{45}$N$_2$O$_8$ 693.3176, found 693.3156.

Example 2.2a

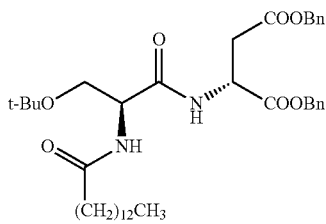

The compound 2.2a (white solid, 105 mg, 0.16 mmol, 27%) was obtained from the compound 2.1a by following the general protocols B then C.

Rf=0.30 (cyclohexane/EtOAc 7:3); Tm=59-61° C.; $^1$H NMR (400 MHz, CDCl$_3$) δ ppm 0.88 (t, J=6.9 Hz, 3H), 1.16 (s, 9H), 1.18-1.36 (m, 20H), 1.56-1.67 (m, 2H), 2.20 (t, J=7.2 Hz, 2H), 2.89 (dd, J=17.1, 4.7 Hz, 1H), 3.07 (dd, J=17.1, 4.7 Hz, 1H), 3.27 (dd, J=8.6, 8.6 Hz, 1H), 3.79 (dd, J=8.6, 4.1 Hz, 1H), 4.43-4.50 (m, 1H), 4.87-4.93 (m, 1H), 5.06 (s, 2H), 5.13 (s, 2H), 6.36 (d, J=6.3 Hz, 1H, NH), 7.26-7.38 (m, 10H), 7.60 (d, J=8.1 Hz, NH); $^{13}$C NMR (100 MHz, CDCl$_3$) δ ppm 14.2 (CH$_3$), 22.8 (CH$_2$), 25.6 (CH$_2$), 27.4 (3×CH$_3$), 29.4-29.8 (8×CH$_2$), 32.0 (CH$_2$), 36.5 (CH$_2$), 36.7 (CH$_2$), 48.9 (CH), 53.1 (CH), 61.3 (CH$_2$), 66.9 (CH$_2$), 67.6 (CH$_2$), 74.3 (C), 128.5-128.8 (10×CH), 135.3 (C), 135.5 (C), 170.3 (C), 170.6 (C), 170.6 (C), 173.4 (C); Mass (ESI+) m/z (%) 690 (100) [M+Na]$^+$; HRMS (ESI+) m/z calculated for C$_{39}$H$_{59}$N$_2$O$_7$ 667.4322, found 667.4318.

Example 2.2b

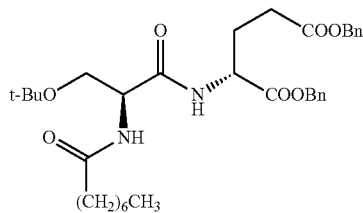

The compound 2.2b (white solid, 67 mg, 0.11 mmol, 39%) was obtained from the compound 2.1b by following the general protocols B then C.

Rf=0.35 (7:3 cyclohexane/EtOAc); Tm=86° C.; $^1$H NMR (400 MHz, CDCl$_3$) δ ppm 0.87 (t, 3H, J=7.0 Hz), 1.17 (s, 9H), 1.23-1.38 (m, 8H), 1.57-1.72 (m, 2H), 1.98-2.11 (m, 1H), 2.19-2.35 (m, 3H), 2.35-2.53 (m, 2H), 3.38 (t, J=8.5 Hz, 1H), 3.78 (dd, J=8.8, 4.2 Hz, 1H), 4.53-4.60 (m, 1H), 4.67-4.75 (m, 1H), 5.10 (s, 2H), 5.15 (s, 2H), 6.66 (d, J=6.9 Hz, 1H, NH), 7.27-7.38 (m, 10H), 7.45 (d, J=7.9 Hz, 1H, NH); $^{13}$C NMR (100 MHz, CDCl$_3$) δ ppm 14.1 (CH$_3$), 22.6 (2×CH$_2$), 27.4 (3×CH$_3$), 27.5 (CH$_2$), 29.0-30.0 (3×CH$_2$), 31.7 (CH$_2$), 36.6 (CH$_2$), 51.8 (CH), 53.0 (CH), 61.3 (CH$_2$), 66.5 (CH$_2$), 67.41 (CH$_2$), 74.4 (3×CH$_3$), 128.3-128.7 (10× CH), 135.1 (C), 135.8 (C), 170.36 (C), 171.23 (C), 172.34 (C), 173.34 (C); Mass (ESI+) m/z (%) 597 (100) [M+H]$^+$; HRMS (ESI+) m/z calculated for C$_{34}$H$_{49}$N$_2$O$_7$ 597.3540, found 597.3538.

Example 2.2c

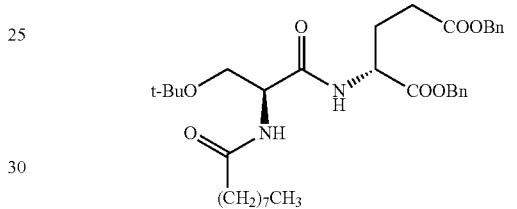

The compound 2.2c (white solid, 69 mg, 0.11 mmol, 39%) was obtained from the compound 2.1b by following the general protocols B then C.

Rf=0.38 (cyclohexane/EtOAc 7:3); Tm=91° C.; $^1$H NMR (400 MHz, CDCl$_3$) δ ppm 0.87 (t, J=7.0 Hz, 3H), 1.17 (s, 9H), 1.22-1.38 (m, 10H), 1.56-1.70 (m, 2H), 1.98-2.10 (m, 1H), 2.18-2.34 (m, 3H), 2.36-2.53 (m, 2H), 3.41 (t, J=8.5 Hz, 1H), 3.76 (dd, J=8.9, 4.1 Hz, 1H), 4.57-4.64 (m, 1H), 4.68-4.76 (m, 1H), 5.09 (s, 2H), 5.14 (s, 2H), 6.75 (d, J=6.9 Hz, 1H, NH), 7.26-7.38 (m, 10H), 7.53 (d, J=7.9 Hz, 1H, NH); $^{13}$C NMR (100 MHz, CDCl$_3$) δ ppm 14.2 (CH$_3$), 22.8 (2×CH$_2$), 27.5 (3×CH$_3$), 27.7 (CH$_2$), 29.3-30.1 (4×CH$_2$), 32.0 (CH$_2$), 36.7 (CH$_2$), 51.9 (CH), 53.1 (CH), 61.4 (CH$_2$), 66.7 (CH$_2$), 67.5 (CH$_2$), 74.5 (C), 128.4-128.8 (10×CH), 135.2 (C), 135.9 (C), 170.5 (C), 171.3 (C), 172.5 (C), 173.5 (C); Mass (ESI+) m/z (%) 633 (100) [M+H]$^+$; HRMS (ESI+) m/z calculated for C$_{35}$H$_{51}$N$_2$O$_7$ 611.3696, found 611.3681.

Example 2.2d

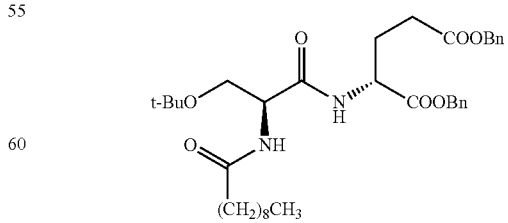

The compound 2.2d (white solid, 195 mg, 0.31 mmol, 45%) was obtained from the compound 2.1b by following the general protocols B then C.

Rf=0.18 (cyclohexane/EtOAc 7:3); Tm=82-85° C.; $^1$H NMR (400 MHz, CDCl$_3$) δ ppm 0.87 (t, J=6.9 Hz, 3H), 1.16 (s, 9H), 1.19-1.35 (m, 12H), 1.55-1.66 (m, 2H), 1.96-2.07 (m, 1H), 2.21 (t, J=7.8 Hz, 2H), 2.21-2.30 (m, 1H), 2.32-2.50 (m, 2H), 3.31 (dd, J=8.7, 8.7 Hz, 1H), 3.80 (dd, J=8.7, 4.2 Hz, 1H), 4.44-4.50 (m, 1H), 4.65-4.72 (m, 1H), 5.08 (s, 2H), 5.15 (s, 2H), 6.40 (d, J=6.4 Hz, 1H, NH), 7.27-7.36 (m, 11H); $^{13}$C NMR (100 MHz, CDCl$_3$) δ ppm 14.1 (CH$_3$), 22.7 (2×CH$_2$), 25.6 (CH$_2$), 27.4 (3×CH$_3$), 27.5 (CH$_2$), 29.3-29.44 (4×CH$_2$), 30.0 (CH$_2$), 31.9 (CH$_2$), 36.6 (CH$_2$), 51.8 (CH), 53.0 (CH), 61.3 (CH$_2$), 66.5 (CH$_2$), 67.3 (CH$_2$), 74.3 (C), 128.3-128.7 (10×CH), 135.2 (C), 135.8 (C), 170.4 (C), 171.2 (C), 172.3 (C), 173.3 (C); Mass (ESI+) m/z (%) 626 (30) [M+H]$^+$, 648 (100) [M+Na]$^+$; HRMS (ESI+) m/z calculated for C$_{36}$H$_{53}$N$_2$O$_7$ 625.3853, found 625.3846.

Example 2.2e

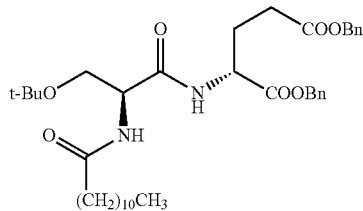

The compound 2.2e (white solid, 182 mg, 0.28 mmol, 48%) was obtained from the compound 2.1b by following the general protocols B then C.

Rf=0.12 (cyclohexane/EtOAc 8:2); Tm=67-69° C.; $^1$H NMR (400 MHz, CDCl$_3$) δ ppm 0.88 (t, J=6.9 Hz, 3H), 1.17 (s, 9H), 1.19-1.35 (m, 16H), 1.56-1.67 (m, 2H), 1.96-2.08 (m, 1H), 2.21 (t, J=7.6 Hz, 2H), 2.21-2.32 (m, 1H), 2.32-2.50 (m, 2H), 3.30 (dd, J=8.7, 8.7 Hz, 1H), 3.81 (dd, J=8.7, 4.2 Hz, 1H), 4.42-4.49 (m, 1H), 4.64-4.72 (m, 1H), 5.09 (s, 2H), 5.16 (s, 2H), 6.38 (d, J=6.3 Hz, 1H, NH), 7.23-7.39 (m, 11H); $^{13}$C NMR (100 MHz, CDCl$_3$) δ ppm 14.2 (CH$_3$), 22.8 (CH$_2$), 25.6 (CH$_2$), 27.5 (3×CH$_3$), 27.6 (CH$_2$), 29.4-29.7 (6×CH$_2$), 30.0 (CH$_2$), 32.0 (CH$_2$), 36.7 (CH$_2$), 51.9 (CH), 53.1 (CH), 61.4 (CH$_2$), 66.6 (CH$_2$), 67.5 (CH$_2$), 74.4 (C), 128.4-128.8 (10×CH), 135.2 (C), 135.9 (C), 170.4 (C), 171.3 (C), 172.4 (C), 173.4 (C); Mass (ESI+) m/z (%) 131 (30), 199 (40), 654 (50) [M+H]$^+$, 677 (100), 699 (20); HRMS (ESI+) m/z calculated for C$_{38}$H$_{57}$N$_2$O$_7$ 653.4166, found 653.4158.

Example 2.2f

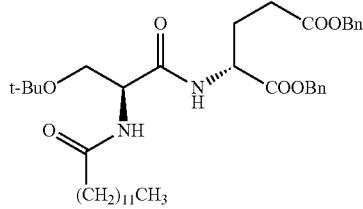

The compound 2.2f (white solid, 233 mg, 0.35 mmol, 50%) was obtained from the compound 2.1b by following the general protocols B then C.

Rf=0.24 (cyclohexane/EtOAc 7:3); Tm=68-71° C.; $^1$H NMR (400 MHz, CDCl$_3$) δ ppm 0.88 (t, J=6.9 Hz, 3H), 1.17 (s, 9H), 1.20-1.36 (m, 18H), 1.55-1.67 (m, 2H), 1.96-2.08 (m, 1H), 2.21 (t, J=7.6 Hz, 2H), 2.21-2.32 (m, 1H), 2.32-2.50 (m, 2H), 3.31 (dd, J=8.7, 8.7 Hz, 1H), 3.80 (dd, J=8.7, 4.2 Hz, 1H), 4.44-4.50 (m, 1H), 4.63-4.73 (m, 1H), 5.08 (s, 2H), 5.15 (s, 2H), 6.41 (d, J=6.4 Hz, 1H, NH), 7.25-7.37 (m, 11H); $^{13}$C NMR (100 MHz, CDCl$_3$) δ ppm 14.1 (CH$_3$), 22.7 (CH$_2$), 25.5 (CH$_2$), 27.4 (3×CH$_3$), 27.5 (CH$_2$), 29.3-29.7 (7×CH$_2$), 29.9 (CH$_2$), 31.9 (CH$_2$), 36.5 (CH$_2$), 51.8 (CH), 53.0 (CH), 61.3 (CH$_2$), 66.5 (CH$_2$), 67.3 (CH$_2$), 74.2 (C), 128.3-128.6 (10×CH), 135.2 (C), 135.8 (C), 170.4 (C), 171.2 (C), 172.3 (C), 173.3 (C); Mass (ESI+) m/z (%) 668 (20) [M+H]$^+$, 690 (100) [M+Na]$^+$, HRMS (ESI+) m/z calculated for C$_{39}$H$_{59}$N$_2$O$_7$ 667.4322, found 667.4334.

Example 2.2g

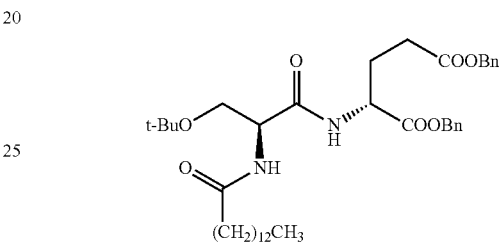

The compound 2.2g (white solid, 187 mg, 0.27 mmol, 48%) was obtained from the compound 2.1b by following the general protocols B then C.

Rf=0.07 (cyclohexane/EtOAc 8:2); Tm=71-73° C.; $^1$H NMR (400 MHz, CDCl$_3$) δ ppm 0.88 (t, J=6.9 Hz, 3H), 1.17 (s, 9H), 1.20-1.36 (m, 20H), 1.56-1.67 (m, 2H), 1.97-2.08 (m, 1H), 2.21 (t, J=7.6 Hz, 2H), 2.23-2.50 (m, 3H), 3.29 (dd, J=8.7, 8.7 Hz, 1H), 3.80 (dd, J=8.7, 4.2 Hz, 1H), 4.41-4.49 (m, 1H), 4.63-4.72 (m, 1H), 5.09 (s, 2H), 5.14 (d, J=12.3 Hz, 1H), 5.18 (d, J=12.3 Hz, 1H), 7.25-7.39 (m, 11H); $^{13}$C NMR (100 MHz, CDCl$_3$) δ ppm 14.2 (CH$_3$), 22.8 (CH$_2$), 25.6 (CH$_2$), 27.5 (3×CH$_3$), 27.6 (CH$_2$), 29.4-29.8 (8×CH$_2$), 30.0 (CH$_2$), 32.0 (CH$_2$), 36.7 (CH$_2$), 51.9 (CH), 53.1 (CH), 61.4 (CH$_2$), 66.6 (CH$_2$), 67.5 (CH$_2$), 74.4 (C), 128.4-128.8 (10×CH), 135.2 (C), 135.8 (C), 170.5 (C), 171.3 (C), 172.4 (C), 173.4 (C); Mass (ESI+) m/z (%) 131 (65), 199 (100), 682 (60) [M+H]$^+$; HRMS (ESI+) m/z calculated for C$_{40}$H$_{51}$N$_2$O$_7$ 681.4479, found 681.4447.

Example 2.2h

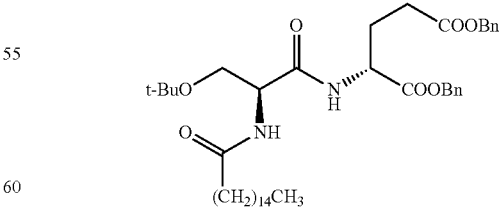

The compound 2.2h (white solid, 93 mg, 0.13 mmol, 30%) was obtained from the compound 2.1b by following the general protocols B then C. Rf=0.11 (cyclohexane/EtOAc 8:2); Tm=69-71° C.; $^1$H NMR (400 MHz, CDCl$_3$) δ ppm 0.86 (t, J=6.8 Hz, 3H), 1.15 (s, 9H), 1.19-1.31 (m, 24H), 1.56-1.63 (m, 2H), 1.96-2.05 (m, 1H), 2.19 (t, J=7.6 Hz, 2H), 2.23-2.47 (m, 3H), 3.27 (dd, J=8.7, 8.7 Hz, 1H), 3.79 (dd, J=8.7, 4.2 Hz, 1H), 4.41-4.45 (m, 1H), 4.63-4.68 (m, 1H), 5.07 (s, 2H), 5.14 (s, 2H), 7.22-7.37 (m, 10H); $^{13}$C NMR (100 MHz, CDCl$_3$) δ ppm 14.3 (CH$_3$), 22.9 (CH$_2$), 25.7 (CH$_2$), 27.6 (3×CH$_3$), 27.7 (CH$_2$), 29.5-30.2 (11×CH$_2$), 32.1 (CH$_2$), 36.8 (CH$_2$), 52.0 (CH), 53.2 (CH), 61.5 (CH$_2$), 66.7 (CH$_2$), 67.6 (CH$_2$), 74.6 (C), 128.5-128.9 (10×CH), 135.3 (C), 136.0 (C), 170.5 (C), 171.4 (C), 172.5 (C), 173.5 (C); Mass (ESI+) m/z (%) 199 (15), 710 (100) [M+H]$^+$, 732 (15) [M+Na]$^+$; HRMS (ESI+) m/z calculated for C$_{42}$H$_{65}$N$_2$O$_7$ 709.4792, found 709.4805.

Example 2.2i

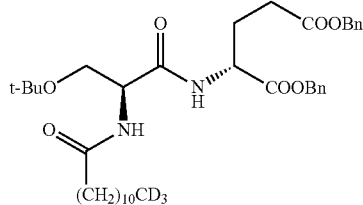

The compound 2.2i (white solid, 162 mg, 0.24 mmol, 83%) was obtained from the compound 2.1b by following the general protocol A (purification: silica gel column chromatography, eluent: cyclohexane/EtOAc 9:1 to 7:3).

Rf=0.28 (cyclohexane/EtOAc 7:3); Tm=70-72° C.; $^1$H NMR (400 MHz, CDCl$_3$) δ ppm 1.15 (s, 9H), 1.94-2.06 (m, 1H), 2.17-2.29 (m, 1H), 2.29-2.48 (m, 2H), 3.29 (dd, J=8.6, 8.6 Hz, 1H), 3.78 (dd, J=8.6, 4.1 Hz, 1H), 4.39-4.48 (m, 1H), 4.60-4.71 (m, 1H), 5.06 (s, 2H), 5.13 (s, 2H), 6.36 (d, J=6.4 Hz, 1H, NH), 7.22-7.35 (m, 11H); $^{13}$C NMR (100 MHz, CDCl$_3$) δ ppm 13.1 (st, J$_{C,D}$=18.6 Hz, CD$_3$), 21.4 (qt, J$_{C,D}$=18.4 Hz, CD$_2$), 24.5 (qt, J$_{C,D}$=19.2 Hz, CD$_2$), 27.4 (3×CH$_3$), 27.5 (CH$_2$), 27.2-28.8 (6×CD$_2$), 30.0 (CH$_2$), 30.5 (qt, J=18.7 Hz, CD$_2$), 35.7 (qt, J=19.5 Hz, CD$_2$), 51.8 (CH), 53.0 (CH), 61.4 (CH$_2$), 66.5 (CH$_2$), 67.4 (CH$_2$), 74.3 (C), 128.3-128.7 (10×CH), 135.2 (C), 135.8 (C), 170.4 (C), 171.2 (C), 172.3 (C), 173.4 (C); Mass (ESI+) m/z (%) 199 (40), 265 (100), 677 (80) [M+H]$^+$; HRMS (ESI+) m/z calculated for C$_{38}$H$_{34}$D$_{23}$N$_2$O$_7$ 676.5610, found 676.5610.

Example 2.3a

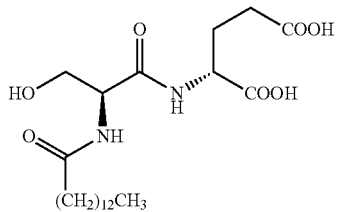

The compound 2.3a (white solid, 55 mg, 0.13 mmol, 98%) was obtained from the compound 2.2a by following the general protocols D1 then K.

Tm=125-135° C.; $^1$H NMR (400 MHz, CD$_3$OD) δ ppm 0.90 (t, J=6.2 Hz, 3H), 1.19-1.42 (m, 20H), 1.54-1.71 (m, 2H), 2.23-2.33 (m, 2H), 2.76-2.93 (m, 2H), 3.71-3.83 (m, 2H), 4.47 (dd, J=5.4, 5.4 Hz, 1H), 4.74 (dd, J=5.4, 5.4 Hz, 1H); $^{13}$C NMR (100 MHz, CD$_3$OD) δ ppm 14.4 (CH$_3$), 23.7 (CH$_2$), 26.8 (CH$_2$), 30.4-30.9 (8×CH$_2$), 33.1 (CH$_2$), 36.9 (CH$_2$), 37.0 (CH$_2$), 50.3 (CH), 56.7 (CH), 63.0 (CH$_2$), 172.2 (C), 174.3 (C), 176.5 (C), 176.5 (C); Mass (ESI–) m/z (%) 429 (100) [M–H]$^-$; HRMS (ESI–) m/z calculated for C$_{21}$H$_{37}$N$_2$O$_7$ 429.2601, found 429.2591.

Example 2.3b

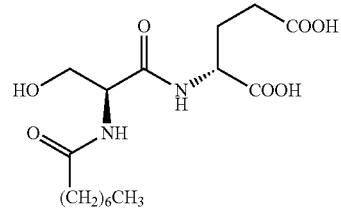

The compound 2.3b (hygroscopic colorless solid, 27 mg, 0.07 mmol, quantitative) was obtained from the compound 2.2b by following the general protocols D1 then K.

Tm=39-40° C.; $^1$H NMR (400 MHz, MeOD) δ ppm 0.89 (t, J=7.0 Hz, 3H), 1.23-1.39 (m, 8H), 1.57-1.67 (m, 2H), 1.90-2.02 (m, 1H), 2.16-2.32 (m, 3H), 2.40 (t, J=7.5 Hz, 2H), 3.72-3.84 (m, 2H), 4.42-4.50 (m, 2H); $^{13}$C NMR (100 MHz, MeOD) δ ppm 14.4 (CH$_3$), 23.6 (CH$_2$), 26.8 (CH$_2$), 27.9 (CH$_2$), 30.1-31.1 (3×CH$_2$), 32.8 (CH$_2$), 36.9 (CH$_2$), 53.3 (CH), 56.7 (CH), 63.0 (CH$_2$), 172.6 (C), 175.0 (C), 176.5 (C), 176.6 (C); Mass (ESI–) m/z (%) 360 (100) [M–H]$^-$; HRMS (ESI–) m/z calculated for C$_{16}$H$_{27}$N$_2$O$_7$ 359.1818, found 359.1803.

Example 2.3c

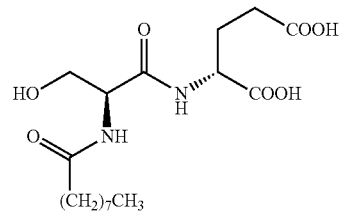

The compound 2.3c (hygroscopic colorless solid, 31 mg, 0.08 mmol, quantitative) was obtained from the compound 2.2c by following the general protocols D1 then K.

Tm=46° C.; $^1$H NMR (400 MHz, MeOD) δ ppm 0.89 (t, J=7.0 Hz, 3H), 1.22-1.40 (m, 10H), 1.56-1.68 (m, 2H), 1.90-2.02 (m, 1H), 2.15-2.32 (m, 3H), 2.40 (t, J=7.7 Hz, 2H), 3.73-3.83 (m, 2H), 4.43-4.50 (m, 2H); $^{13}$C NMR (100 MHz, MeOD) δ ppm 14.4 (CH$_3$), 23.7 (CH$_2$), 26.8 (CH$_2$), 27.9 (CH$_2$), 30.2-31.1 (4×CH$_2$), 33.0 (CH$_2$), 36.9 (CH$_2$), 53.3 (CH), 56.7 (CH), 63.0 (CH$_2$), 172.6 (C), 175.1 (C), 176.5 (C), 176.6 (C); Mass (ESI–) m/z (%) 373 (100) [M–H]$^-$; HRMS (ESI–) m/z calculated for C$_{17}$H$_{29}$N$_2$O$_7$ 373.1975, found 373.1992.

Example 2.3d

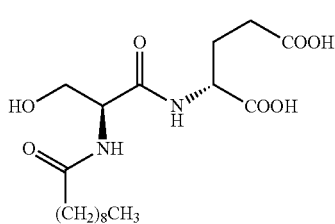

The compound 2.3d (white solid, 182 mg, 0.47 mmol, 94%) was obtained from the compound 2.2d by following the general protocols D1 then K.

Tm=53-57° C.; $^1$H NMR (400 MHz, CD$_3$OD) δ ppm 0.89 (t, J=6.8 Hz, 3H), 1.22-1.38 (m, 12H), 1.56-1.69 (m, 2H), 1.90-2.03 (m, 1H), 2.14-2.26 (m, 1H), 2.29 (t, J=7.3 Hz, 2H), 2.36-2.43 (m, 2H), 3.73-3.84 (m, 2H), 4.42-4.52 (m, 2H). $^{13}$C NMR (100 MHz, CD$_3$OD) δ ppm 14.4 (CH$_3$), 23.7 (CH$_2$), 26.8 (CH$_2$), 27.9 (CH$_2$), 30.3-30.5 (4×CH$_2$), 31.1 (CH$_2$), 33.0 (CH$_2$), 36.9 (CH$_2$), 53.3 (CH), 56.6 (CH), 63.1 (CH$_2$), 172.5 (C), 174.9 (C), 176.5 (C), 176.5 (C); Mass (ESI−) m/z (%) 387 (100) [M−H]$^−$, 404 (20); HRMS (ESI−) m/z calculated for C$_{18}$H$_{31}$N$_2$O$_7$ 387.2131, found 387.2140.

Example 2.3e

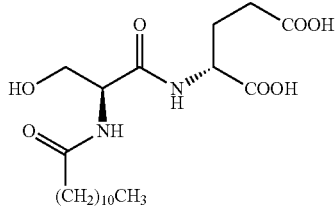

The compound 2.3e (white solid, 1.683 g. 4.04 mmol, 70%) was obtained from the compound 2.2e by following the general protocols D1 then K.

Tm=100-102° C.; $^1$H NMR (400 MHz, CD$_3$OD) δ ppm 0.90 (t, J=6.9 Hz, 3H), 1.22-1.38 (m, 16H), 1.57-1.67 (m, 2H), 1.91-2.01 (m, 1H), 2.15-2.26 (m, 1H), 2.29 (t, J=7.2 Hz, 2H), 2.37-2.44 (m, 2H), 3.72-3.81 (m, 2H), 4.43-4.51 (m, 2H); $^{13}$C NMR (100 MHz, CD$_3$OD) δ ppm 14.4 (CH$_3$), 23.7 (CH$_2$), 26.8 (CH$_2$), 27.9 (CH$_2$), 30.4-30.7 (6×CH$_2$), 31.0 (CH$_2$), 33.1 (CH$_2$), 36.9 (CH$_2$), 53.1 (CH), 56.6 (CH), 63.1 (CH$_2$), 172.6 (C), 174.6 (C), 176.4 (C), 176.5 (C); Mass (ESI−) m/z (%) 157 (40), 199 (30), 387 (80), 415 (100) [M−H]$^−$; HRMS (ESI−) m/z calculated for C$_{20}$H$_{35}$N$_2$O$_7$ 415.2444, found 415.2447.

Example 2.3f

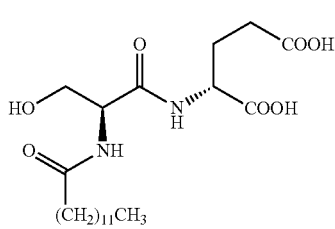

The compound 2.3f (white solid, 115 mg, 0.27 mmol, 89%) was obtained from the compound 2.2f by following the general protocols D1 then K.

Tm=58-63° C.; $^1$H NMR (400 MHz, CD$_3$OD) δ ppm 0.89 (t, J=6.9 Hz, 3H), 1.21-1.41 (m, 16H), 1.54-1.68 (m, 2H), 1.90-2.04 (m, 1H), 2.14-2.27 (m, 1H), 2.29 (t, J=7.4 Hz, 2H), 2.36-2.48 (m, 2H), 3.71-3.83 (m, 2H), 4.43-4.53 (m, 2H); $^{13}$C NMR (100 MHz, CD$_3$OD) δ ppm 14.4 (CH$_3$), 23.7 (CH$_2$), 26.8 (CH$_2$), 27.8 (CH$_2$), 30.3-30.9 (7×CH$_2$), 31.0 (CH$_2$), 33.0 (CH$_2$), 36.9 (CH$_2$), 53.1 (CH), 56.6 (CH), 63.1 (CH$_2$), 172.6 (C), 174.6 (C), 176.4 (C), 176.5 (C); Mass (ESI−) m/z (%) 429 (100) [M−H]$^−$, 446; HRMS (ESI−) m/z calculated for C$_{21}$H$_{37}$N$_2$O$_7$ 429.2601, found 429.2599.

Example 2.3q

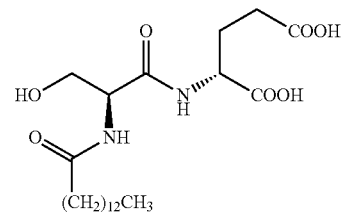

The compound 2.3g (white solid, 57 mg, 0.13 mmol, quantitative) was obtained from the compound 2.2g by following the general protocols D1 then K.

Tm=109-112° C.; $^1$H NMR (400 MHz, CD$_3$OD) δ ppm 0.90 (t, J=6.8 Hz, 3H), 1.19-1.39 (m, 20H), 1.57-1.67 (m, 2H), 1.90-2.02 (m, 1H), 2.16-2.26 (m, 3H), 2.29 (t, J=7.4 Hz, 2H), 2.36-2.45 (m, 2H), 3.71-3.84 (m, 2H), 4.43-4.52 (m, 2H); $^{13}$C NMR (100 MHz, CD$_3$OD) δ ppm 14.4 (CH$_3$), 23.7 (CH$_2$), 26.8 (CH$_2$), 27.9 (CH$_2$), 30.4-30.9 (8×CH$_2$), 31.1 (CH$_2$), 33.0 (CH$_2$), 36.9 (CH$_2$), 53.3 (CH), 56.6 (CH), 63.1 (CH$_2$), 172.6 (C), 174.9 (C), 176.5 (C), 176.5 (C). Mass (ESI−) m/z (%) 443 (100) [M−H]$^−$; HRMS (ESI−) m/z calculated for C$_{22}$H$_{39}$N$_2$O$_7$ 443.2757, found 443.2754.

Example 2.3h

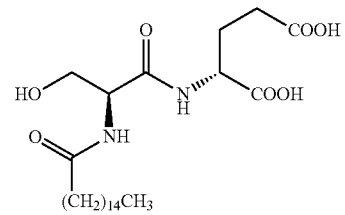

The compound 2.3h (white solid, 36 mg, 0.08 mmol, 65%) was obtained from the compound 2.2h by following the general protocols D1 then K.

Tm=111-113° C.; $^1$H NMR (400 MHz, CD$_3$OD) (δ ppm 0.90 (t, J=6.8 Hz, 3H), 1.19-1.37 (m, 24H), 1.55-1.68 (m, 2H), 1.90-2.03 (m, 1H), 2.15-2.26 (m, 1H), 2.29 (t, J=7.4 Hz, 2H), 2.36-2.44 (m, 2H), 3.72-3.82 (m, 2H), 4.43-4.52 (m, 2H); $^{13}$C NMR (100 MHz, CD$_3$OD) δ ppm 14.4 (CH$_3$), 23.7 (CH$_2$), 26.8 (CH$_2$), 27.9 (CH$_2$), 30.4-30.8 (10×CH$_2$), 31.1 (CH$_2$), 33.1 (CH$_2$), 36.9 (CH$_2$), 53.2 (CH), 56.6 (CH), 63.1 (CH$_2$), 172.6 (C), 174.7 (C), 176.5 (C), 176.5 (C); Mass (ESI−) m/z (%) 471 (100) [M−H]⁻; HRMS (ESI−) m/z calculated for $C_{24}H_{43}N_2O_7$ 471.3070, found 471.3057.

Example 2.3i

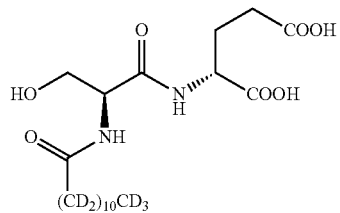

The compound 2.3i (white solid, 33 mg, 0.08 mmol, 75%) was obtained from the compound 2.2i by following the general protocols D1 then K.

Tm>80° C. (décomposé); ¹H NMR (400 MHz, CD₃OD) (δ ppm 1.90-2.03 (m, 1H), 2.14-2.27 (m, 1H), 2.33-2.48 (m, 2H), 3.72-3.84 (m, 2H), 4.41-4.54 (m, 2H); ¹³C NMR (100 MHz, CD₃OD) δ ppm 13.3 (st, $J_{C,D}$=19.8 Hz. CD₃), 22.4 (qt, $J_{C,D}$=19.6, Hz, CD₂), 25.7 (qt, $J_{C,D}$=20.2 Hz, CD₂), 27.9 (CH₂), 28.6-29.9 (6×CD₂), 31.1 (CH₂), 31.7 (qt, $J_{C,D}$=16.9 Hz, CD₂), 36.1 (qt, $J_{C,D}$=21.1 Hz, CD₂), 53.2 (CH), 56.6 (CH), 63.1 (CH₂), 172.6 (C), 174.8 (C), 176.5 (C), 176.6 (C); Mass (ESI−) m/z (%) 438 (100) [M−H]⁻; HRMS (ESI−) m/z calculated for $C_{20}H_{12}D_{23}N_2O_7$ 438.3888, found 438.3889.

Example 4: Compounds 3.1 to 3.9

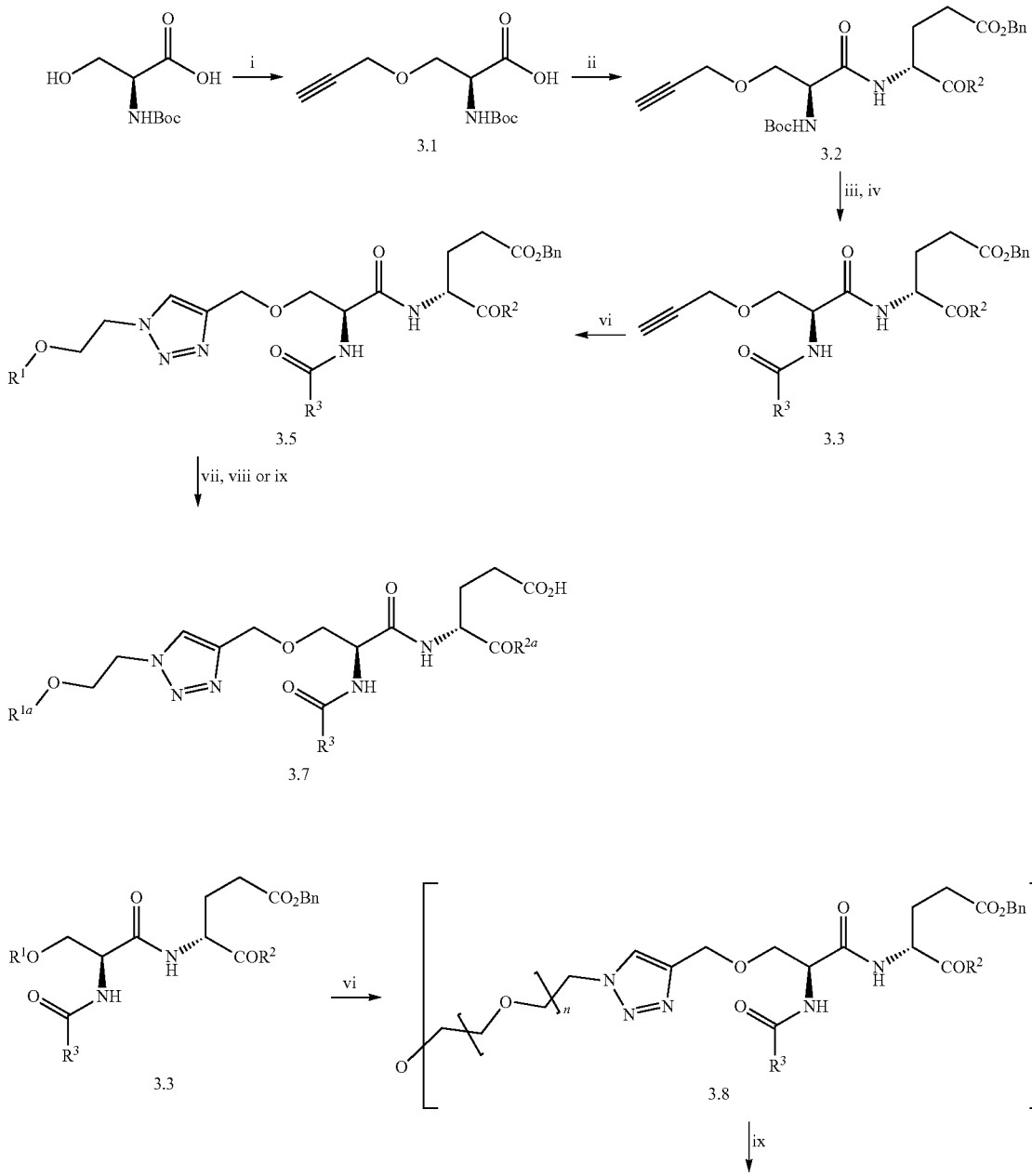

-continued

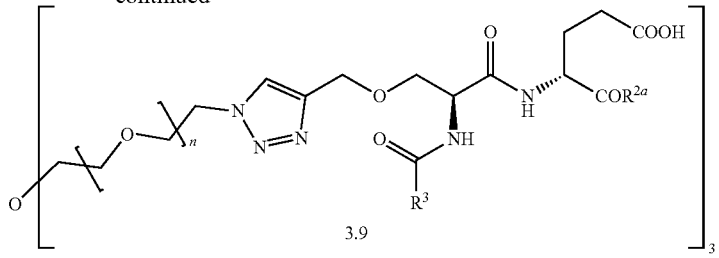

3.9 i. Allyl or propargyl bromide, NaH, DMF;
ii. H-D-Glu(OBn).p-tosylate or H-L-Glu(OBn)-Gly-OBn, TBTU, DIEA, DMF;
iii. TFA, CH$_2$Cl$_2$;
iv. R$^3$COCl, DMAP, pyridine, CH$_2$Cl$_2$;
vi. Azidosaccharide (acetate) or PEG-N$_3$ or N$_3$-PEG-N$_3$, CuSO$_4$·5H$_2$O, sodium ascorbate, DMF, H$_2$O;
vii. MeONa, MeOH then Dowex;
viii. LiOH, THF/H$_2$O;
ix. H$_2$, Pd/C, MeOH. With R$^1$ = Acsaccharide or PEG; R$^{1a}$ = saccharide or PEG R$^2$ = -OBn or -NHCH$_2$COOBn;

$R^{2a}$=—OH or —NHCH$_2$COOH; $R^3$=—(CH$_2$)$_n$CH$_3$, —CH[(CH$_2$)$_n$CH$_3$]$_2$ or —(CH$_2$)$_n$cyclohexyl.

Compound 3.1b

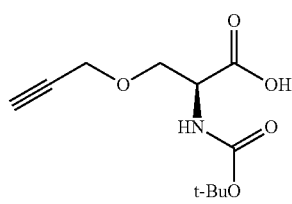 [SMILES: C#CCOC[C@H](NC(=O)OC(C)(C)C)C(=O)O]

The product 3.1b (yellowish oil, 915 mg, 3.76 mmol, 77%) was obtained according to the protocol above (example 3.1a) using propargyl bromide. The crude product obtained (colorless oil) is directly used for the following step.

Compound 3.2b

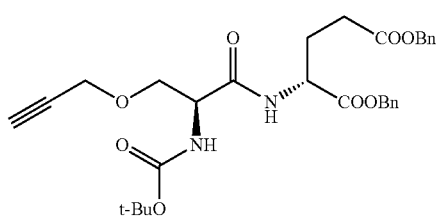

The compound 3.2b (yellowish oil, 1.91 g, 3.45 mmol, 77%) was obtained from the compound 3.1a by following the general protocol A (purification: silica gel column chromatography, eluent: cyclohexane/EtOAc 9:1 to 7:3).

Rf=0.33 (cyclohexane/EtOAc 7:3); $^1$H NMR (400 MHz, CDCl$_3$) δ ppm 1.44 (s, 9H), 1.95-2.08 (m, 1H), 2.22-2.32 (m, 1H), 2.32-2.53 (m, 3H), 3.66 (dd, J=9.3, 6.1 Hz, 1H), 3.87 (dd, J=9.3, 4.0 Hz, 1H), 4.08 (dd, J=15.9, 2.4 Hz, 1H), 4.15 (dd, J=15.9, 2.4 Hz, 1H), 4.25-4.38 (m, 1H), 4.66-4.74 (m, 1H), 5.08 (s, 2H), 5.15 (s, 2H), 5.38 (s, 1H, NH), 6.98 (d, J=7.9 Hz, 1H, NH), 7.26-7.39 (m, 10H); $^{13}$C NMR (100 MHz, CDCl$_3$) δ ppm 27.4 (CH$_2$), 28.3 (3×CH$_3$), 30.0 (CH$_2$), 51.7 (CH), 54.0 (CH), 58.6 (CH$_2$), 66.5 (CH$_2$), 67.4 (CH$_2$), 69.3 (CH$_2$), 75.4 (CH), 79.0 (C), 80.4 (C), 128.3-128.7 (10×CH), 135.2 (C), 135.8 (C), 155.6 (C), 170.0 (C), 171.4 (C), 172.5 (C); Mass (ESI+) m/z (%) 453 (40), 497 (35), 553 (100) [M+H]$^+$; HRMS (ESI+) m/z calculated for C$_{30}$H$_{37}$N$_2$O$_8$ 553.2550, found 553.2528.

Compound 3.2c

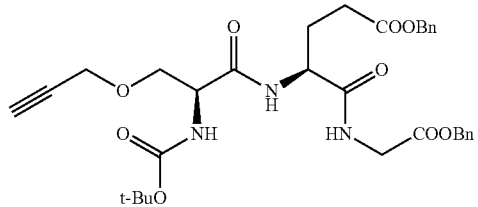

The compound 3.2c (yellowish oil, 886 mg, 1.45 mmol, 65%) was obtained from the compound 3.1b and H-L-Glu(OBn)-Gly-OBn (not described) by following the general protocol A (purification: silica gel column chromatography, eluent: cyclohexane/EtOAc 9:1 to 7:3).

Rf=0.28 (cyclohexane/EtOAc 5:5); $^1$H NMR (400 MHz, CDCl$_3$) δ ppm 1.43 (s, 9H), 1.99-2.13 (m, 1H), 2.15-2.27 (m, 1H), 2.39 (t, J=2.4 Hz, 1H), 2.42-2.54 (m, 1H), 2.54-2.66 (m, 1H), 3.69 (dd, J=9.2, 5.6 Hz, 1H), 3.86 (dd, J=9.3, 4.4 Hz, 1H), 3.95 (dd, J=17.9, 5.1 Hz, 1H), 4.12 (dd, J=17.9, 6.0 Hz, 1H), 4.09 (dd, J=15.8, 2.4 Hz, 1H), 4.14 (dd, J=15.8, 2.4 Hz, 1H), 4.22-4.32 (m, 1H), 4.52-4.61 (m, 1H), 5.11 (d, J=12.4 Hz, 1H), 5.12 (d, J=12.2 Hz, 1H), 5.14 (d, J=12.4 Hz, 1H), 5.17 (d, J=12.2 Hz, 1H), 5.41 (d, J=5.3 Hz, 1H, NH), 7.15 (bs, 1H, NH), 7.28-7.43 (m, 10H); $^{13}$C NMR (100 MHz, CDCl$_3$) δ ppm 26.9 (CH$_2$), 28.4 (3×CH$_3$), 30.5 (CH$_2$), 52.9 (CH), 54.7 (CH), 58.8 (CH$_2$), 66.8 (CH$_2$), 67.2 (CH$_2$), 69.5 (CH$_2$), 75.6 (CH), 78.9 (C), 80.8 (C), 128.4-128.7 (10×CH), 135.4 (C), 135.8 (C), 155.9 (C), 169.5 (C), 170.3 (C), 171.2 (C), 174.0 (C); Mass (ESI+) m/z (%) 610 (15) [M+H]$^+$, 632 (100) [M+Na]$^+$; HRMS (ESI+) m/z calculated for C$_{32}$H$_{40}$N$_3$O$_9$ 610.2765, found 610.2764.

Compound 3.3d

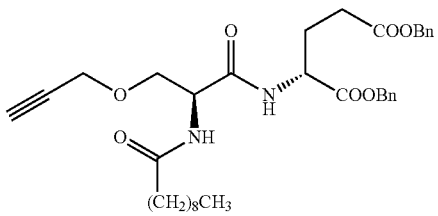

The compound 3.3d (white solid, 813 mg, 1.34 mmol, 67%) was obtained from the compound 3.2b by following the general protocols G then C.

Rf=0.13 (cyclohexane/EtOAc 7:3); Tm=93-94° C.; $^1$H NMR (400 MHz, CDCl$_3$) δ ppm 0.87 (t, J=6.9 Hz, 3H), 1.19-1.35 (m, 12H), 1.56-1.67 (m, 2H), 1.97-2.10 (m, 1H), 2.16-2.32 (m, 3H), 2.32-2.51 (m, 3H), 3.62 (dd, J=9.2, 6.6 Hz, 1H), 3.88 (dd, J=9.2, 4.0 Hz, 1H), 4.10 (dd, J=16.0, 2.4 Hz, 1H), 4.18 (dd, J=16.0, 2.4 Hz, 1H), 4.58-4.72 (m, 2H), 5.09 (s, 2H), 5.15 (s, 2H), 6.32 (d, J=7.0 Hz, 1H, NH), 7.02 (d, J=7.8 Hz, 1H, NH), 7.28-7.40 (m, 10H); $^{13}$C NMR (100 MHz, CDCl$_3$) δ ppm 14.2 (CH$_3$), 22.8 (CH$_2$), 25.6 (CH$_2$), 27.3 (CH$_2$), 29.4-29.5 (4×CH$_2$), 30.1 (CH$_2$), 32.0 (CH$_2$), 36.7 (CH$_2$), 52.0 (CH), 52.4 (CH), 58.7 (CH$_2$), 66.7 (CH$_2$), 67.5 (CH$_2$), 69.0 (CH$_2$), 75.5 (CH), 79.0 (C), 128.4-128.8 (10×CH), 135.2 (C), 135.9 (C), 169.8 (C), 171.3 (C), 172.6 (C), 173.5 (C); Mass (ESI+) m/z (%) 491 (100), 608 (20) [M+H]$^+$, 630 (95) [M+Na]$^+$; HRMS (ESI+) m/z calculated for C$_{35}$H$_{47}$N$_2$O$_7$ 607.3383, found 607.3373.

Compound 3.3e

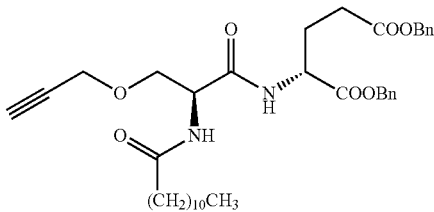

The compound 3.3e (white solid, 651 mg. 1.03 mmol, 77%) was obtained from the compound 3.2b by following the general protocols G then C.

Rf=0.16 (cyclohexane/EtOAc 7:3); Tm=99-100° C.; $^1$H NMR (400 MHz, CDCl$_3$) δ ppm 0.88 (t, J=6.9 Hz, 3H), 1.19-1.35 (m, 16H), 1.56-1.67 (m, 2H), 1.96-2.09 (m, 1H), 2.16-2.31 (m, 3H), 2.32-2.50 (m, 3H), 3.62 (dd, J=9.2, 6.6 Hz, 1H), 3.89 (dd, J=9.2, 4.0 Hz, 1H), 4.10 (dd, J=16.0, 2.4 Hz, 1H), 4.18 (dd, J=16.0, 2.4 Hz, 1H), 4.59-4.72 (m, 2H), 5.09 (s, 2H), 5.15 (s, 2H), 6.32 (d, J=7.0 Hz, 1H, NH), 7.02 (d, J=7.8 Hz, 1H, NH), 7.27-7.39 (m, 10H); $^{13}$C NMR (100 MHz, CDCl$_3$) δ ppm 14.2 (CH$_3$), 22.8 (CH$_2$), 25.6 (CH$_2$), 27.3 (CH$_2$), 29.4-29.7 (6×CH$_2$), 30.1 (CH$_2$), 32.0 (CH$_2$), 36.7 (CH$_2$), 52.0 (CH), 52.4 (CH), 58.7 (CH$_2$), 66.7 (CH$_2$), 67.5 (CH$_2$), 69.0 (CH$_2$), 75.5 (CH), 79.0 (C), 128.4-128.8 (10×CH), 135.2 (C), 135.9 (C), 169.8 (C), 171.3 (C), 172.6 (C), 173.5 (C1'); Mass (ESI+) m/z (%) 636 (25) [M+H]$^+$, 658 (100) [M+Na]$^+$; HRMS (ESI+) m/z calculated for C$_{37}$H$_{51}$N$_2$O$_7$ 635.3696, found 635.3697.

Compound 3.3f

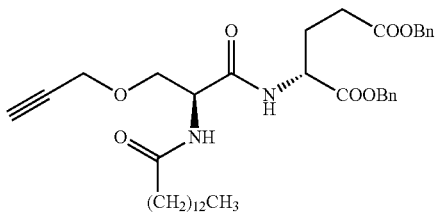

The compound 3.3f (white solid, 1.085 g, 1.64 mmol, 84%) was obtained from the compound 3.2b by following the general protocols G then C.

Rf=0.21 (cyclohexane/EtOAc 7:3); Tm=101-103° C.; $^1$H NMR (400 MHz, CDCl$_3$) δ ppm 0.88 (t, J=6.8 Hz, 3H), 1.17-1.37 (m, 20H), 1.56-1.66 (m, 2H), 1.97-2.08 (m, 1H), 2.14-2.32 (m, 3H), 2.32-2.50 (m, 3H), 3.62 (dd, J=9.2, 6.6 Hz, 1H), 3.89 (dd, J=9.2, 4.1 Hz, 1H), 4.10 (dd, J=16.0, 2.4 Hz, 1H), 4.17 (dd, J=16.0, 2.4 Hz, 1H), 4.62-4.72 (m, 2H), 5.09 (s, 2H), 5.15 (s, 2H), 6.39 (d, J=7.1 Hz, 1H, NH), 7.10 (d, J=7.9 Hz, 1H, NH), 7.28-7.39 (m, 10H); $^{13}$C NMR (100 MHz, CDCl$_3$) δ ppm 14.2 (CH$_3$), 22.8 (CH$_2$), 25.6 (CH$_2$), 27.2 (CH$_2$), 29.4-29.8 (8×CH$_2$), 30.1 (CH$_2$), 32.0 (CH$_2$), 36.6 (CH$_2$), 51.9 (CH), 52.4 (CH), 58.7 (CH$_2$), 66.6 (CH$_2$), 67.5 (CH$_2$), 69.0 (CH$_2$), 75.5 (CH), 79.0 (C), 128.4-128.8 (10×CH), 135.2 (C), 135.8 (C), 169.8 (C), 171.3 (C), 172.6 (C), 173.5 (C); Mass (ESI+) m/z (%) 199 (15), 664 (100) [M+H]$^+$, 686 (20) [M+Na]$^+$; HRMS (ESI+) m/z calculated for C$_{39}$H$_{55}$N$_2$O$_7$ 663.4009, found 663.4006.

Compound 3.3g

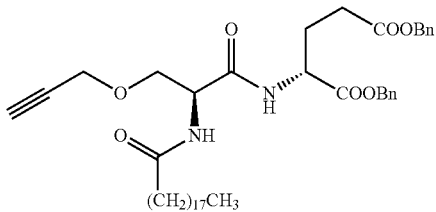

The compound 3.3g (white solid, 467 mg, 0.64 mmol, 47%) was obtained from the compound 3.2b by following the general protocols G then C.

Rf=0.18 (cyclohexane/EtOAc 7:3); Tm=105-108° C.; $^1$H NMR (400 MHz, CDCl$_3$) δ ppm 0.88 (t, J=6.9 Hz, 3H), 1.18-1.36 (m, 30H), 1.56-1.68 (m, 2H), 1.96-2.09 (m, 1H), 2.15-2.32 (m, 3H), 2.33-2.50 (m, 3H), 3.62 (dd, J=9.2, 6.6 Hz, 1H), 3.89 (dd, J=9.2, 4.0 Hz, 1H), 4.10 (dd, J=16.0, 2.4 Hz, 1H), 4.17 (dd, J=16.0, 2.4 Hz, 1H), 4.60-4.72 (m, 2H), 5.09 (s, 2H), 5.15 (s, 2H), 6.35 (d, J=7.0 Hz, 1H, NH), 7.05 (d, J=7.9 Hz, 1H, NH), 7.29-7.39 (m, 10H); $^{13}$C NMR (100 MHz, CDCl$_3$) δ ppm 14.2 (CH$_3$), 22.8 (CH$_2$), 25.6 (CH$_2$), 27.2 (CH$_2$), 29.4-29.8 (13×CH$_2$), 30.1 (CH$_2$), 32.0 (CH$_2$), 36.6 (CH$_2$), 52.0 (CH), 52.4 (CH), 58.7 (CH$_2$), 66.6 (CH$_2$), 67.5 (CH$_2$), 69.0 (CH$_2$), 75.5 (CH), 79.0 (C); 128.4-128.8 (10×CH), 135.2 (C), 135.8 (C), 169.8 (C), 171.3 (C), 172.6 (C), 173.6 (C); Mass (ESI+) m/z (%) 734 (55) [M+H]$^+$, 756 (100) [M+Na]$^+$; HRMS (ESI+) m/z calculated for C$_{44}$H$_{64}$N$_2$O$_7$Na 755.4611, found 755.4612.

Compound 3.3h

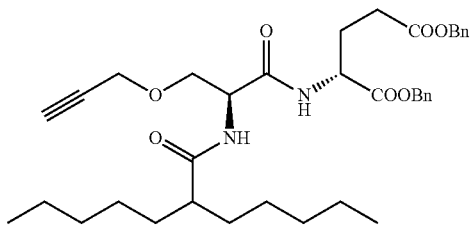

The compound 3.3h (white solid, 206 mg, 0.32 mmol, 65%) was obtained from the compound 3.2b by following the general protocols G then C.

Rf=0.38 (cyclohexane/EtOAc 7:3); Tm=87-90° C.; $^1$H NMR (400 MHz, CDCl$_3$) δ ppm 0.84 (t, J=6.7 Hz, 3H), 0.86 (t, J=7.0 Hz, 3H), 1.15-1.32 (m, 12H), 1.32-1.46 (m, 2H), 1.51-1.67 (m, 2H), 1.94-2.14 (m, 2H), 2.37 (dd, J=2.4, 2.4 Hz, 1H), 2.21-2.50 (m, 3H), 3.63 (dd, J=9.2, 6.3 Hz, 1H), 3.89 (dd, J=9.2, 4.7 Hz, 1H), 4.09 (dd, J=16.0, 2.4 Hz, 1H), 4.14 (dd, J=16.0, 2.4 Hz, 1H), 4.65-4.77 (m, 2H), 5.08 (s, 2H), 5.11 (d, J=12.2 Hz, 1H), 5.15 (d, J=12.2 Hz, 1H), 6.44 (d, J=7.1 Hz, 1H, NH), 7.16 (d, J=8.0 Hz, 1H, NH), 7.24-7.37 (m, 10H); $^{13}$C NMR (100 MHz, CDCl$_3$) δ ppm 14.0 (2×CH$_3$), 22.4 (CH$_2$), 22.5 (CH$_2$), 27.2, 27.2 (2×CH$_2$), 27.4 (CH$_2$), 29.9 (CH$_2$), 31.8 (CH$_2$), 31.9 (CH$_2$), 32.8 (CH$_2$), 32.9 (CH$_2$), 47.7 (CH), 51.6 (CH), 52.2 (CH), 58.5 (CH$_2$), 66.4 (CH$_2$), 67.3 (CH$_2$), 69.1 (CH$_2$), 75.4 (CH), 78.9 (C), 128.2-128.6 (10×CH), 135.1 (C), 135.8 (C), 169.6 (C), 171.1 (C), 172.3 (C), 176.3 (C). Mass (ESI+) m/z (%) 413 (30), 635 (40) [M+H]$^+$, 657 (100) [M+Na]$^+$; HRMS (ESI+) m/z calculated for C$_{37}$H$_{50}$N$_2$O$_7$Na 657.3516, found 657.3532.

Compound 3.3i

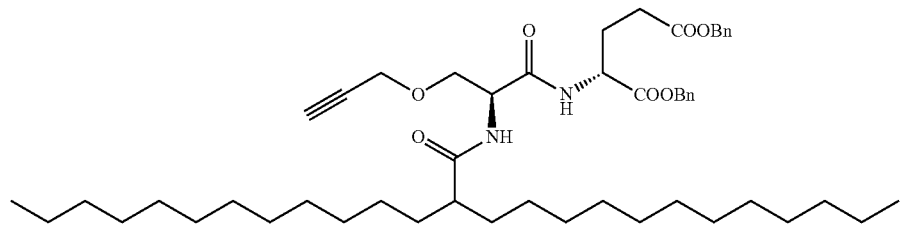

The compound 3.3i (white solid, 361 mg, 0.43 mmol, 40%) was obtained from the compound 3.2b by following the general protocols G then C.

Rf=0.52 (cyclohexane/EtOAc 7:3); Tm=91-93° C.; $^1$H NMR (400 MHz, CDCl$_3$) δ ppm 0.87 (t, J=6.9 Hz, 3H), 0.88 (t, J=6.9 Hz, 3H), 1.11-1.33 (m, 40H), 1.35-1.47 (m, 2H), 1.50-1.65 (m, 2H), 1.94-2.14 (m, 2H), 2.37 (dd, J=2.4, 2.4 Hz, 1H), 2.21-2.50 (m, 3H), 3.62 (dd, J=9.2, 6.6 Hz, 1H), 3.90 (dd, J=9.2, 4.0 Hz, 1H), 4.10 (dd, J=16.0, 2.4 Hz, 1H), 4.18 (dd, J=16.0, 2.4 Hz, 1H), 4.62-4.75 (m, 2H), 5.09 (s, 2H), 5.15 (s, 2H), 6.34 (d, J=7.0 Hz, 1H, NH), 7.01 (d, J=7.9 Hz, 1H, NH), 7.26-7.38 (m, 10H); $^{13}$C NMR (100 MHz, CDCl$_3$) δ ppm 14.2 (2×CH$_3$), 22.8 (2×CH$_2$), 27.5 (CH$_2$), 27.7 (2×CH$_2$), 29.5-30.0 (16×CH$_2$), 32.0 (CH$_2$), 32.9 (CH$_2$), 33.1 (CH$_2$), 47.9 (CH), 51.8 (CH), 52.2 (CH), 58.6 (CH$_2$), 66.6 (CH$_2$), 67.5 (CH$_2$), 69.0 (CH$_2$), 75.5 (CH), 79.0 (C), 128.4-128.7 (10×CH), 135.2 (C), 135.8 (C), 169.6 (C), 171.2 (C), 172.4 (C), 176.5 (C). Mass (ESI+) m/z (%) 853 (100) [M+Na]$^+$; HRMS (ESI+) m/z calculated for C$_{51}$H$_{78}$N$_2$O$_7$Na 853.5707, found 853.5693.

Compound 3.3j

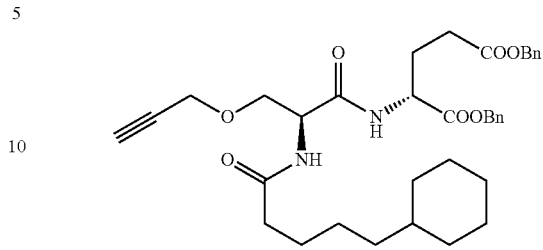

The compound 3.3j (white solid, 337 mg, 0.54 mmol, 66%) was obtained from the compound 3.2b by following the general protocols G then C.

Rf=0.13 (cyclohexane/EtOAc 7:3); Tm=100-102° C.; $^1$H NMR (400 MHz, CDCl$_3$) δ ppm 0.76-0.91 (m, 2H), 1.05-1.24 (m, 6H), 1.23-1.35 (m, 2H), 1.53-1.73 (m, 7H), 1.94-2.08 (m, 1H), 2.13-2.31 (m, 3H), 2.31-2.52 (m, 3H), 3.62 (dd, J=9.2, 6.5 Hz, 1H), 3.89 (dd, J=9.2, 4.1 Hz, 1H), 4.09 (dd, J=16.0, 2.4 Hz, 1H), 4.16 (dd, J=16.0, 2.4 Hz, 1H), 4.61-4.72 (m, 2H), 5.09 (s, 2H), 5.13 (s, 2H), 6.38 (d, J=7.1 Hz, 1H, NH), 7.11 (d, J=7.9 Hz, 1H, NH), 7.28-7.39 (m, 10H); $^{13}$C NMR (100 MHz, CDCl$_3$) δ ppm 25.9 (CH$_2$), 26.5 (2×CH$_2$), 26.6 (CH$_2$), 26.8 (CH$_2$), 27.2 (CH$_2$), 30.1 (CH$_2$), 33.4 (2×CH$_2$), 36.6 (CH$_2$), 37.2 (CH$_2$), 37.5 (CH), 51.9 (CH), 52.3 (CH), 58.6 (CH$_2$), 66.6 (CH$_2$), 67.4 (CH$_2$), 69.0 (CH$_2$), 75.4 (CH), 79.0 (C), 128.3-128.7 (10×CH), 135.2 (C), 135.8 (C), 169.8 (C), 171.2 (C), 172.6 (C), 173.5 (C). Mass (ESI+) m/z (%) 619 (60) [M+H]$^+$, 641 (100) [M+Na]$^+$; HRMS (ESI+) m/z calculated for C$_{36}$H$_{46}$N$_2$O$_7$Na 641.3203, found 641.3199.

Compound 3.3k

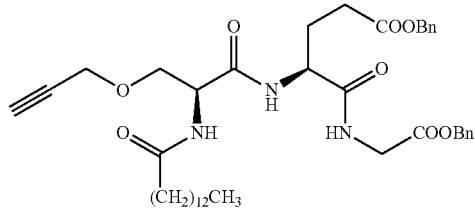

The compound 3.3k (white solid, 506 mg, 0.70 mmol, 72%) was obtained from the compound 3.2c by following the general protocols G then C.

Rf=0.19 (cyclohexane/EtOAc 5:5); Tm=122-123° C.; $^1$H NMR (400 MHz, CDCl$_3$) δ ppm 0.87 (t, J=6.9 Hz, 3H), 1.15-1.35 (m, 20H), 1.54-1.69 (m, 2H), 2.01-2.29 (m, 4H), 2.39 (dd, J=2.4, 2.4 Hz, 1H), 2.43-2.66 (m, 2H), 3.67 (dd, J=9.3, 6.0 Hz, 1H), 3.89 (dd, J=9.3, 4.3 Hz, 1H), 3.96 (dd, J=17.9, 5.4 Hz, 1H), 4.10 (dd, J=15.8, 2.4 Hz, 1H), 4.14 (dd, J=17.9, 6.2 Hz, 1H), 4.15 (dd, J=15.8, 2.4 Hz, 1H), 4.54-4.63 (m, 2H), 5.11 (s, 2H), 5.12 (d, J=12.2 Hz, 1H), 5.16 (d, J=12.2 Hz, 1H), 6.45 (d, J=6.8 Hz, 1H, NH), 7.21 (dd, J=6.2, 5.4 Hz, 1H, NH), 7.28-7.38 (m, 10H), 7.57 (d, J=7.7 Hz, 1H, NH); $^{13}$C NMR (100 MHz, CDCl$_3$) δ ppm 14.2 (CH$_3$), 22.8 (CH$_2$), 25.6 (CH$_2$), 26.7 (CH$_2$), 29.4-29.8 (8×CH$_2$), 30.5 (CH$_2$), 32.0 (CH$_2$), 36.5 (CH$_2$), 41.4 (CH$_2$), 53.0 (CH), 53.1 (CH), 58.8 (CH$_2$), 66.8 (CH$_2$), 67.2 (CH$_2$), 69.4 (CH$_2$), 75.6 (CH), 78.9 (C), 128.3-128.7 (10×CH), 135.4 (C), 135.7 (C), 169.6 (C), 170.0 (C), 171.1 (C), 173.9 (C), 174.2 (C); Mass (ESI+) m/z (%) 720 (20) [M+H]$^+$, 742 (100) [M+Na]$^+$; HRMS (ESI+) m/z calculated for C$_{41}$H$_{57}$N$_3$O$_8$Na 742.4043, found 742.4042.

Compound 3.5a

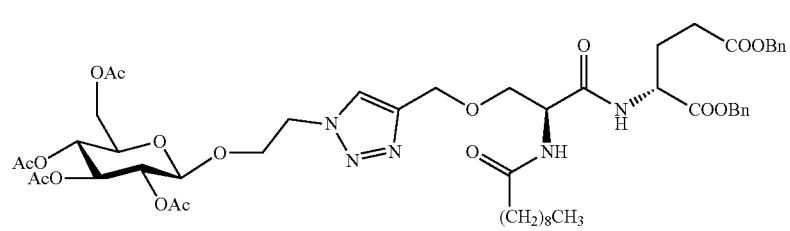

The compound 3.5a (yellowish oil, 541 mg, 0.53 mmol, 71%) was obtained from the compound 3.3d by following the general protocol I.

Rf=0.07 (CH$_2$Cl$_2$/EtOAc 1:1); $^1$H NMR (400 MHz, CD$_3$OD) δ ppm 0.88 (t, J=6.7 Hz, 3H), 1.20-1.36 (m, 12H), 1.54-1.65 (m, 2H), 1.91 (s, 3H), 1.93 (s, 3H), 1.99 (s, 3H), 2.02 (s, 3H), 1.96-2.09 (m, 1H), 2.15-2.30 (m, 3H), 2.34-2.48 (m, 2H), 3.68 (dd, J=9.5, 5.4 Hz, 1H), 3.77 (dd, J=9.5, 5.1 Hz, 1H), 3.85 (ddd, J=9.6, 4.7, 1.8 Hz, 1H), 3.90-3.99 (m, 1H), 4.12 (dd, J=12.5, 1.8 Hz, 1H), 4.12-4.20 (m, 1H), 4.26 (dd, J=12.5, 4.7 Hz, 1H), 4.45-4.69 (m, 6H), 4.66 (d, J=8.0 Hz, 1H), 4.90 (dd, J=9.5, 8.0 Hz, 1H), 5.01 (dd, J=9.6, 9.6 Hz, 1H), 5.09 (s, 2H), 5.12 (d, J=12.5 Hz, 1H), 5.17 (d, J=12.5 Hz, 1H), 5.23 (dd, J=9.6, 9.6 Hz, 1H), 7.24-7.40 (m, 10H), 7.83 (s, 1H); $^{13}$C NMR (100 MHz, CD$_3$OD) δ ppm 14.5 (CH$_3$), 20.6 (2×CH$_3$), 20.7 (2×CH$_3$), 23.7 (CH$_2$), 26.8 (CH$_2$), 27.6 (CH$_2$), 30.3, 30.4, 30.5, 30.6 (4×CH$_2$), 31.0 (CH$_2$), 33.0 (CH$_2$), 36.8 (CH$_2$), 51.3 (CH$_2$), 53.1 (CH), 54.5 (CH), 63.0 (CH$_2$), 65.2 (CH$_2$), 67.4 (CH$_2$), 68.0 (CH$_2$), 69.0 (CH$_2$), 69.7 (CH), 70.9 (CH$_2$), 72.5 (CH), 72.9 (CH), 74.0 (CH), 101.6 (CH), 125.8 (CH), 129.2-129.6 (10×CH), 137.1 (C), 137.5 (C), 145.4 (C), 171.1 (2×C), 171.5 (C), 172.2 (2×C), 172.6 (C), 174.0 (C), 176.2 (C); Mass (ESI+) m/z (%) 1047 (100) [M+Na]$^+$; HRMS (ESI+) m/z calculated for C$_{51}$H$_{70}$N$_5$O$_{17}$ 1024.4767, found 1024.4784.

Compound 3.5b

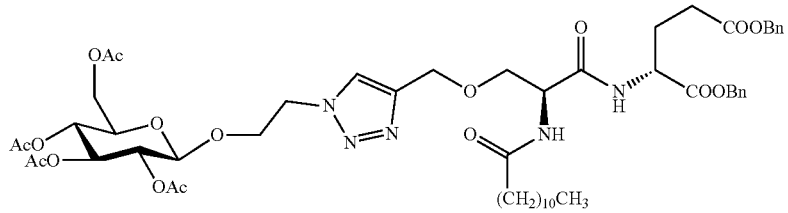

The compound 3.5b (yellowish oil, 181 mg, 0.17 mmol, 72%) was obtained from the compound 3.3e by following the general protocol I.

Rf=0.11 (CH$_2$Cl$_2$/EtOAc 1:1); $^1$H NMR (400 MHz, CD$_3$OD) δ ppm 0.89 (t, J=6.9 Hz, 3H), 1.20-1.36 (m, 12H), 1.54-1.65 (m, 2H), 1.91 (s, 3H), 1.93 (s, 3H), 1.99 (s, 3H), 2.02 (s, 3H), 1.94-2.06 (m, 1H), 2.15-2.31 (m, 3H), 2.36-2.44 (m, 2H), 3.65-3.73 (m, 1H), 3.73-3.81 (m, 1H), 3.85 (ddd, J=10.0, 4.7, 2.4 Hz, 1H), 3.91-3.99 (m, 1H), 4.12 (dd, J=12.4, 2.4 Hz, 1H), 4.14-4.20 (m, 1H), 4.26 (dd, J=12.4, 4.7 Hz, 1H), 4.48-4.64 (m, 6H), 4.66 (d, J=8.0 Hz, 1H), 4.89 (dd, J=9.7, 8.0 Hz, 1H), 5.01 (dd, J=10.1, 9.7 Hz, 1H), 5.09 (s, 2H), 5.12 (d, J=12.4 Hz, 1H), 5.17 (d, J=12.4 Hz, 1H), 5.23 (dd, J=9.7, 9.7 Hz, 1H), 7.26-7.37 (m, 10H), 7.83 (s, 1H); $^{13}$C NMR (100 MHz, CD$_3$OD) δ ppm 14.5 (CH$_3$), 20.6 (2×CH$_3$), 20.7 (2×CH$_3$), 23.7 (CH$_2$), 26.8 (CH$_2$), 27.6 (CH$_2$), 30.3-30.7 (6×CH$_2$), 31.0 (CH$_2$), 33.0 (CH$_2$), 36.8 (CH$_2$), 51.2 (CH$_2$), 53.2 (CH), 54.5 (CH), 63.0 (CH$_2$), 65.2 (CH$_2$), 67.4 (CH$_2$), 68.0 (CH$_2$), 69.0 (CH$_2$), 69.7 (CH), 70.9 (CH$_2$), 72.5 (CH), 72.9 (CH), 74.0 (CH), 101.6 (CH), 125.8 (CH), 129.2-129.6 (10×CH), 137.1 (C), 137.5 (C), 145.3 (C), 171.1 (C), 171.2 (C), 171.5 (C), 172.2 (C), 172.6 (C), 174.0 (C), 176.2 (C); Mass (ESI+) m/z (%) 1075 (100) [M+Na]$^+$; HRMS (ESI+) m/z calculated for C$_{53}$H$_{74}$N$_5$O$_{17}$ 1052.5080, found 1052.5117.

Compound 3.5c

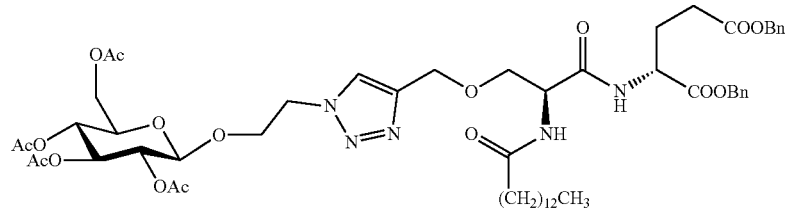

The compound 3.5c (yellowish oil, 568 mg, 0.53 mmol, 77%) was obtained from the compound 3.3f by following the general protocol I.

Rf=0.08 (CH$_2$Cl$_2$/EtOAc 1:1); $^1$H NMR (400 MHz, CD$_3$OD) δ ppm 0.89 (t, J=6.9 Hz, 3H), 1.21-1.34 (m, 20H), 1.53-1.65 (m, 2H); 1.91, 1.93, 1.99, 2.02 (s, 12H), 1.86-1.99 (m, 1H), 2.15-2.31 (m, 3H), 2.34-2.48 (m, 2H), 3.69 (dd, J=9.6, 5.4 Hz, 1H), 3.77 (dd, J=9.6, 5.1 Hz, 1H), 3.85 (ddd, J=10.1, 4.7, 2.4 Hz, 1H), 3.92-3.99 (m, 1H), 4.12 (dd, J=12.3, 2.4 Hz, 1H), 4.13-4.20 (m, 1H), 4.26 (dd, J=12.3, 4.7 Hz, 1H), 4.47-4.64 (m, 6H), 4.66 (d, J=7.9 Hz, 1H), 4.88 (dd, J=9.5, 7.9 Hz, 1H), 5.01 (dd, J=10.1, 9.5 Hz, 1H), 5.10 (s, 2H), 5.11-5.20 (m, 2H), 5.23 (dd, J=9.5, 9.5 Hz, 1H), 7.27-7.37 (m, 10H), 7.84 (s, 1H); $^{13}$C NMR (100 MHz, CD$_3$OD) δ ppm 14.5 (CH$_3$), 20.6 (CH$_3$), 20.7 (2×CH$_3$), 20.9 (CH$_3$), 23.7 (CH$_2$), 26.8 (CH$_2$), 27.6 (CH$_2$), 30.4-30.8 (8×CH$_2$), 33.1 (CH$_2$), 31.0 (CH$_2$), 36.8 (CH$_2$), 51.3 (CH$_2$), 53.2 (CH), 54.6 (CH), 61.5 (CH$_2$), 65.2 (CH$_2$), 67.4 (CH$_2$), 68.0 (CH$_2$), 69.0 (CH$_2$), 69.7 (CH), 70.9 (CH$_2$), 72.6 (CH), 72.9 (CH), 74.0 (CH), 101.6 (CH), 125.8 (CH), 129.2-129.6 (10×CH), 137.2 (C), 137.5 (C), 145.4 (C), 171.1 (C), 171.2 (C), 171.5 (C), 172.3 (C), 172.6 (C), 173.0 (C), 174.1 (C), 176.3 (C); Mass (ESI+) m/z (%) 130 (35), 199 (40), 1081 (100) [M+H]$^+$; HRMS (ESI+) m/z calculated for C$_{55}$H$_{78}$N$_5$O$_{17}$ 1080.5393, found 1080.5375.

Compound 3.5d

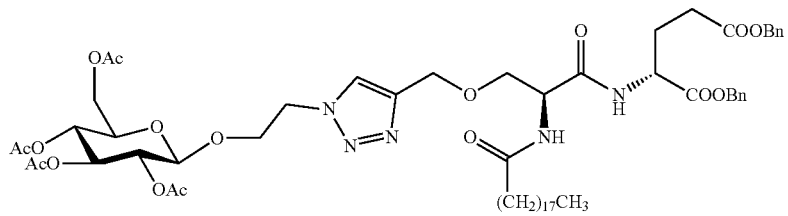

The compound 3.5d (white solid, 160 mg, 0.14 mmol, 87%) was obtained from the compound 3.3f by following the general protocol I.

Rf=0.09 (CH$_2$Cl$_2$/EtOAc 1:1); Tm=58-60° C.; $^1$H NMR (400 MHz, CD$_3$OD) δ ppm 0.83 (t, J=6.8 Hz, 3H), 1.08-1.30 (m, 30H), 1.49-1.64 (m, 2H), 1.87, 1.93, 1.96, 2.02 (s, 12H), 1.86-1.99 (m, 1H), 2.11-2.85 (m, 3H), 2.26-2.45 (m, 2H), 3.51-3.60 (m, 1H), 3.66 (ddd, J=10.1, 4.7, 1.9 Hz, 1H), 3.78-3.97 (m, 2H), 4.08 (dd, J=12.4, 1.9 Hz, 1H), 4.11-4.18 (m, 1H), 4.21 (dd, J=12.4, 4.7 Hz, 1H), 4.33-4.69 (m, 6H), 4.43 (d, J=7.9 Hz, 1H), 4.95 (dd, J=9.5, 8.0 Hz, 1H), 5.03 (dd, J=10.1, 9.5 Hz, 1H), 5.03 (s, 2H), 5.10 (s, 2H), 5.13 (dd, J=9.5, 9.5 Hz, 1H), 6.80 (bs, 1H), 7.18-7.35 (m, 10H), 7.39 (d, J=6.8 Hz, 1H), 7.58 (s, 1H); $^{13}$C NMR (100 MHz, CD$_3$OD) δ ppm 14.1 (CH$_3$), 20.5, 20.5, 20.5 (3×CH$_3$), 20.6 (CH$_3$), 22.6 (CH$_2$), 25.5 (CH$_2$), 26.9 (CH$_2$), 29.3-29.6 (13×CH$_2$), 30.0 (CH$_2$), 31.8 (CH$_2$), 36.3 (CH$_2$), 49.9 (CH$_2$), 51.8 (CH), 52.5 (CH), 61.7 (CH$_2$), 64.6 (CH$_2$), 66.4 (CH$_2$), 67.1 (CH$_2$), 67.7 (CH$_2$), 68.1 (CH), 69.7 (CH$_2$), 70.9 (CH), 71.9 (CH), 72.4 (CH), 100.4 (CH), 124.0 (CH), 128.1-128.5 (10×CH), 135.2 (C), 135.8 (C), 144.1 (C), 169.3 (C), 169.5 (C), 170.0 (C), 170.0 (C), 170.5 (C), 171.2 (C), 172.4 (C), 173.5 (C); Mass (ESI+) m/z (%) 1151 (100) [M+H]$^+$; HRMS (ESI+) m/z calculated for C$_{60}$H$_{38}$N$_5$O$_{17}$ 1150.6175, found 1150.6163.

Compound 3.5e

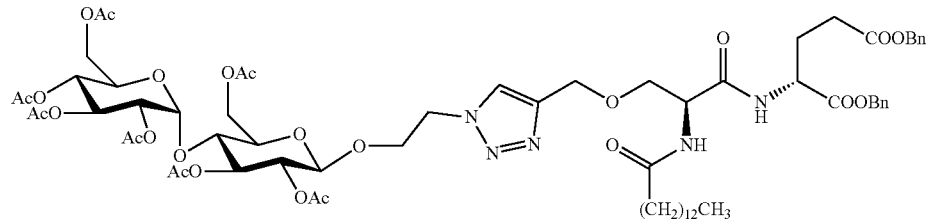

The compound 3.5e (white solid, 302 mg. 0.22 mmol, 74%) was obtained from the compound 3.3f by following the general protocol I.

Rf=0.06 (CH$_2$Cl$_2$/EtOAc 1:1); Tm=78-80° C.; $^1$H NMR (400 MHz, CD$_3$OD) δ ppm 0.89 (t, J=6.9 Hz, 3H), 1.22-1.37 (m, 20H), 1.54-1.65 (m, 2H), 1.89, 1.96, 1.98, 2.00, 2.01, 2.05, 2.09 (s, 21H), 1.91-2.03 (m, 1H), 2.15-2.29 (m, 3H), 2.39-2.42 (m, 2H), 3.68 (dd, J=9.6, 5.5 Hz, 1H), 3.76 (dd, J=9.6, 5.1 Hz, 1H), 3.79-3.83 (m, 1H), 3.92-4.00 (m, 2H), 4.03-4.07 (m, 1H), 4.12 (dd, J=6.3, 2.5 Hz, 1H), 4.14-4.17 (m, 1H), 4.20-4.28 (m, 2H), 4.48-4.63 (m, 7H), 4.66 (d, J=7.9 Hz, 1H), 4.76 (dd, J=9.1, 7.9 Hz, 1H); 4.81-4.85 (m, 1H), 5.04 (dd, J=10.0, 10.0 Hz, 1H), 5.10 (s, 2H), 5.11-5.20 (m, 2H), 5.27 (dd, J=9.1, 9.1 Hz, 1H), 5.33-5.38 (m, 2H), 7.26-7.39 (m, 10H), 7.83 (s, 1H); $^{13}$C NMR (100 MHz, CD$_3$OD) δ ppm 14.5 (CH$_3$), 20.5-21.2 (7×CH$_3$), 23.7 (CH$_2$), 26.8 (CH$_2$), 27.6 (CH$_2$), 30.3-30.8 (8×CH$_2$), 31.0 (CH$_2$), 33.1 (CH$_2$), 36.8 (CH$_2$), 51.3 (CH$_2$), 53.1 (CH), 54.5 (CH), 63.0 (CH$_2$), 64.1 (CH$_2$), 65.2 (CH$_2$), 67.4 (CH$_2$), 68.0 (CH$_2$), 69.0 (CH$_2$); 69.6 (CH), 69.8 (CH), 70.7 (CH), 70.9 (CH$_2$), 71.6 (CH), 73.3 (CH), 73.5 (CH), 74.7 (CH), 76.3 (CH), 97.1 (CH), 101.4 (CH), 125.8 (CH), 129.2-129.6 (10×CH), 145.5 (C), 137.2 (C), 137.6 (C), 171.1-172.2 (7×C), 172.2 (C), 172.6 (C), 174.1 (C), 176.3 (C); Mass (ESI+) m/z (%) 1369 (100) [M+H]$^+$; HRMS (ESI+) m/z calculated for C$_{67}$H$_{94}$N$_5$O$_{25}$ 1368.6238, found 1368.6237.

Compound 3.5f

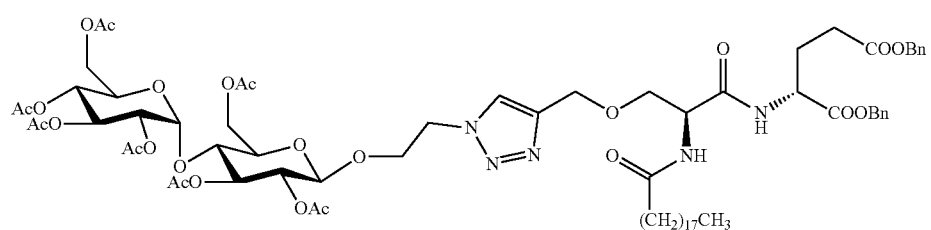

The compound 3.5f (white solid, 192 mg, 0.13 mmol, 83%) was obtained from the compound 3.3f by following the general protocol I.

Rf=0.10 (CH$_2$Cl$_2$/EtOAc 4:6); Tm=90-94° C.; $^1$H NMR (400 MHz, CDCl$_3$) δ ppm 0.84 (t, J=6.8 Hz, 3H), 1.14-1.31 (m, 30H), 1.52-1.62 (m, 2H), 1.87, 1.94, 1.96, 1.98, 1.99, 2.05, 2.09 (s, 21H), 1.91-2.03 (m, 1H), 2.13-2.26 (m, 3H), 2.26-2.43 (m, 2H), 3.50-3.59 (m, 1H), 3.60-3.66 (m, 1H), 3.80-3.99 (m, 4H), 4.02 (dd, J=12.4, 2.2 Hz, 1H), 4.09-4.25 (m, 3H), 4.33-4.70 (m, 7H), 4.46 (d, J=7.8 Hz, 1H), 4.75-4.85 (m, 2H), 5.02 (dd, J=9.8, 9.8 Hz, 1H), 5.04 (s, 2H), 5.09 (d, J=12.4 Hz, 1H), 5.13 (d, J=12.4 Hz, 1H), 5.19 (dd, J=9.2, 9.2 Hz, 1H), 5.32 (dd, J=10.3, 9.8 Hz, 1H), 5.36 (d, J=4.0 Hz, 1H), 6.70 (d, J=6.0 Hz, 1H, NH), 7.23-7.37 (m, 11H), 7.55 (s, 1H); $^{13}$C NMR (100 MHz, CDCl$_3$) δ ppm 14.1 (CH$_3$), 20.5-20.8 (7×CH$_3$), 22.7 (CH$_2$), 25.5 (CH$_2$), 27.0 (CH$_2$), 29.3-29.7 (13×CH$_2$), 30.0 (CH$_2$), 31.9 (CH$_2$), 36.4 (CH$_2$), 49.9 (CH$_2$), 51.9 (CH), 52.5 (CH), 61.5 (CH$_2$), 62.5 (CH$_2$), 64.6 (CH$_2$), 66.4 (CH$_2$), 67.2 (CH$_2$), 67.8 (CH$_2$), 68.0 (CH), 68.5 (CH), 69.3 (CH), 69.6 (CH$_2$), 70.0 (CH), 71.8 (CH), 72.4 (CH), 72.5 (CH), 75.0 (CH), 95.6 (CH), 100.2 (CH), 123.9 (CH), 128.1-128.6 (CH of Ph), 135.3 (C), 135.8 (C), 144.3 (C), 169.4-170.5 (7×C), 170.0 (C), 171.2 (C), 172.5 (C), 173.5 (C); Mass (ESI+) m/z (%) 1439 (100) [M+H]$^+$; HRMS (ESI+) m/z calculated for C$_{72}$H$_{104}$N$_5$O$_{25}$ 1438.7020, found 1438.7031.

Compound 3.5g

The compound 3.5g (white wax, 207 mg, 0.21 mmol, 85%) was obtained from the compound 3.3f by following the general protocol I (purification: silica gel column chromatography, eluent: CH$_2$Cl$_2$/MeOH 99:1 to 97:3).

Rf=0.18 (CH$_2$Cl$_2$/MeOH 97:3); Tm=50-52° C.; $^1$H NMR (500 MHz, CD$_3$OD) δ ppm 0.89 (t, J=6.9 Hz, 3H), 1.22-1.36 (m, 20H), 1.53-1.65 (m, 2H), 1.91-2.01 (m, 1H), 2.15-2.29 (m, 3H), 2.34-2.46 (m, 2H), 3.33 (s, 3H), 3.49-3.53 (m, 2H), 3.54-3.64 (m, 18H), 3.64-3.70 (m, 1H), 3.71-3.77 (m, 1H), 3.85 (t, J=4.8 Hz, 2H), 4.49-4.63 (m, 6H), 5.09 (s, 2H), 5.12 (d, J=12.4 Hz, 1H), 5.16 (d, J=12.4 Hz, 1H), 7.25-7.37 (m, 10H), 7.96 (s, 1H); $^{13}$C NMR (125 MHz, CD$_3$OD) δ ppm 14.5 (CH$_3$), 23.7 (CH$_2$), 26.8 (CH$_2$), 27.6 (CH$_2$), 30.3-30.8 (8×CH$_2$), 31.0 (CH$_2$), 33.1 (CH$_2$), 36.8 (CH$_2$), 51.5 (CH$_2$), 53.1 (CH), 54.5 (CH), 59.1 (CH$_3$), 65.1 (CH$_2$), 67.4 (CH$_2$), 68.0 (CH$_2$), 70.2 (CH$_2$), 70.8 (CH$_2$), 71.3-71.5 (9×CH$_2$), 73.0 (CH$_2$), 125.9 (CH), 129.2-129.6 (10×CH), 137.1 (C), 137.5 (C), 145.4 (C), 172.5 (C), 174.0 (2×C), 176.2 (C); Mass (ESI+) m/z (%) 985 (20) [M+H]$^+$, 1007 (100) [M+Na]$^+$; HRMS (ESI+) m/z calculated for C$_{52}$H$_{82}$N$_5$O$_{13}$ 984.5909, found 984.5892.

Compound 3.5h

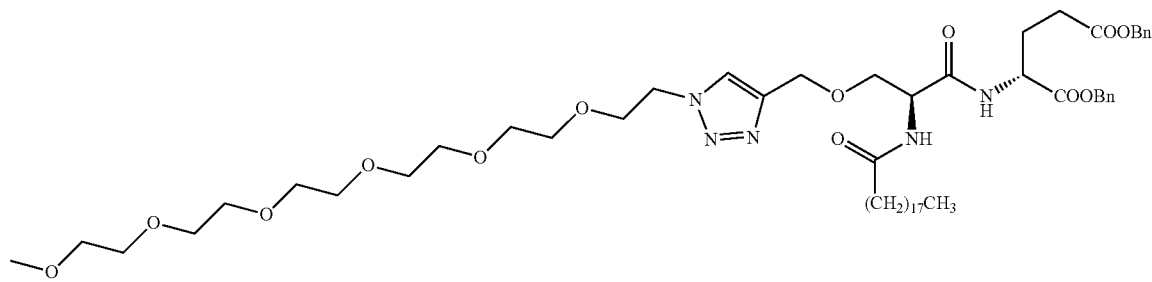

The compound 3.5h (white solid, 91 mg, 0.09 mmol, 88%) was obtained from the compound 3.3g by following the general protocol I (purification: silica gel column chromatography, eluent: CH$_2$Cl$_2$/MeOH 99:1 to 97:3).

Rf=0.20 (CH$_2$Cl$_2$/MeOH 97:3); Tm=61-63° C.; $^1$H NMR (500 MHz, CDCl$_3$) δ ppm 0.85 (t, J=6.9 Hz, 3H), 1.17-1.32 (m, 30H), 1.53-1.64 (m, 2H), 1.93-2.04 (m, 1H), 2.14-2.26 (m, 3H), 2.26-2.43 (m, 2H), 3.33 (s, 3H), 3.48-3.52 (m, 2H), 3.52-3.66 (m, 19H), 3.81 (t, J=5.0 Hz, 2H), 3.88-3.95 (m, 1H), 4.46 (t, J=5.0 Hz, 2H), 4.53-4.69 (m, 4H), 5.05 (s, 2H), 5.10 (d, J=12.3 Hz, 1H), 5.13 (d, J=12.3 Hz, 1H), 6.65 (d, J=5.9 Hz, 1H, NH), 7.24-7.35 (m, 10H), 7.42 (d, J=7.7 Hz, 1H, NH), 7.71 (s, 1H); $^{13}$C NMR (125 MHz, CDCl$_3$) δ ppm 14.1 (CH$_3$), 22.7 (CH$_2$), 25.5 (CH$_2$), 26.9 (CH$_2$), 29.3-29.7 (13×CH$_2$), 30.0 (CH$_2$), 31.9 (CH$_2$), 36.4 (CH$_2$), 50.3 (CH$_2$), 51.9 (CH), 52.5 (CH), 59.0 (CH$_3$), 65.1 (CH$_2$), 66.4 (CH$_2$), 67.2 (CH$_2$), 70.2 (CH$_2$), 70.8 (CH$_2$), 70.5-70.6 (9×CH$_2$), 71.9 (CH$_2$), 123.8 (CH), 128.2-128.6 (10×CH), 135.3 (C), 135.8 (C), 144.1 (C), 170.1 (C), 171.2 (C), 172.5 (C), 173.6 (C); Mass (ESI+) m/z (%) 892 (100), 1077 (70) [M+Na]$^+$; HRMS (ESI+) m/z calculated for C$_{57}$H$_{92}$N$_5$O$_{13}$ 1054.6692, found 1054.6696.

Compound 3.5i

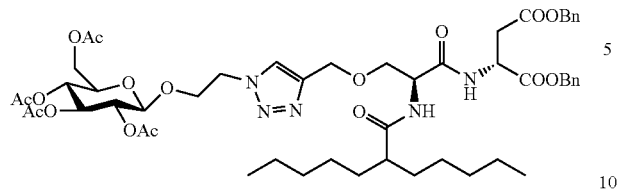

The compound 3.5i (yellowish wax, 115 mg, 0.11 mmol, 38%) was obtained from the compound 3.3h by following the general protocol I.

Rf=0.40 (CH$_2$Cl$_2$/EtOAc 1:1); $^1$H NMR (400 MHz, CD$_3$OD) δ ppm 0.84, 0.87 (t, J=6.9 Hz, 6H), 1.15-1.39 (m, 12H), 1.31-1.44 (m, 2H), 1.47-1.63 (m, 2H), 1.91, 1.93, 1.99, 2.02 (s, 12H), 1.89-2.05 (m, 1H), 2.14-2.25 (m, 1H), 2.26-2.35 (m, 1H), 2.34-2.46 (m, 2H), 3.68 (dd, J=9.6, 5.7 Hz, 1H), 3.76 (dd, J=9.6, 5.3 Hz, 1H), 3.85 (ddd, J=9.7, 4.7, 2.4 Hz, 1H), 3.90-3.99 (m, 1H), 4.12 (dd, J=12.4, 2.4 Hz, 1H), 4.13-4.20 (m, 1H), 4.26 (dd, J=12.4, 4.7 Hz, 1H), 4.49-4.62 (m, 6H), 4.66 (d, J=8.0 Hz, 1H), 4.89 (dd, J=9.7, 8.0 Hz, 1H), 5.02 (dd, J=9.7, 9.5 Hz, 1H), 5.09 (s, 2H), 5.13, 5.17 (d, J=12.4 Hz, 2H), 5.23 (dd, J=9.7, 9.5 Hz, 1H), 7.27-7.37 (m, 10H), 7.83 (s, 1H), 8.12 (d, J=7.5 Hz, 1H, NH), 8.13 (d, J=7.8 Hz, 1H, NH); $^{13}$C NMR (100 MHz, CD$_3$OD) δ ppm 14.4 (CH$_3$), 14.5 (CH$_3$), 20.6 (CH$_3$), 20.6 (CH$_3$), 20.7 (CH$_3$), 20.7 (CH$_3$), 23.5 (CH$_2$), 23.6 (CH$_2$), 27.9 (CH$_2$), 28.2 (CH$_2$), 28.3 (CH$_2$), 30.9 (CH$_2$), 32.9 (CH$_2$), 33.0 (CH$_2$), 34.0 (CH$_2$), 34.1 (CH$_2$), 47.9 (CH), 51.3 (CH$_2$), 53.0 (CH), 54.2 (CH), 63.0 (CH$_2$), 65.2 (CH$_2$), 67.4 (CH$_2$), 68.0 (CH$_2$), 69.0 (CH$_2$), 69.7 (CH), 71.0 (CH$_2$), 72.5 (CH), 72.9 (CH), 74.0 (CH), 101.6 (CH), 125.8 (CH), 129.2-129.6 (10×CH), 137.1 (C), 137.5 (C), 145.4 (C), 171.1 (C), 171.2 (C), 171.5 (C), 172.0 (C), 172.2 (C), 172.5 (C), 173.8 (C), 179.0 (C); Mass (ESI+) m/z (%) 1075 (100) [M+Na]$^+$; HRMS (ESI+) m/z calculated for C$_{53}$H$_{73}$N$_5$O$_{17}$Na 1074.4899, found 1074.4904.

Compound 3.5j

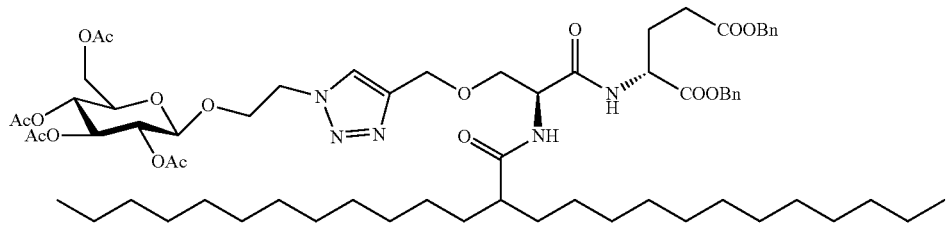

The compound 3.5j (white solid, 190 mg, 0.15 mmol, 90%) was obtained from the compound 3.3i by following the general protocol I.

Rf=0.40 (CH$_2$Cl$_2$/EtOAc 1:1); $^1$H NMR (400 MHz, CDCl$_3$) δ ppm 0.84, 0.85 (t, J=6.9 Hz, 6H), 1.13-1.31 (m, 40H), 1.33-1.44 (m, 2H), 1.48-1.63 (m, 2H), 1.90, 1.95, 1.99, 2.04 (s, 12H), 1.93-2.03 (m, 1H), 2.06-2.15 (m, 1H), 2.16-2.45 (m, 3H), 3.50-3.60 (m, 1H), 3.67 (ddd, J=9.7, 4.7, 2.2 Hz, 1H), 3.81-3.90 (m, 1H), 3.90-3.99 (m, 1H), 4.10 (dd, J=12.3, 2.2 Hz, 1H), 4.14-4.20 (m, 1H), 4.23 (dd, J=12.3, 4.7 Hz, 1H), 4.35-4.71 (m, 6H), 4.44 (d, J=7.9 Hz, 1H), 4.97 (dd, J=9.7, 7.9 Hz, 1H), 5.05 (dd, J=9.7, 9.7 Hz, 1H), 5.05 (s, 2H), 5.13 (s, 2H), 5.15 (dd, J=9.7, 9.7 Hz, 1H), 6.69 (d, J=6.0 Hz, 1H, NH), 7.23-7.40 (m, 11H), 7.57 (s, 1H); $^{13}$C NMR (100 MHz, CDCl$_3$) δ ppm 14.1 (2×CH$_3$), 20.5 (CH$_3$), 20.6 (2×CH$_3$), 20.7 (CH$_3$), 22.7 (2×CH$_2$), 27.3 (CH$_2$), 27.7 (2×CH$_2$), 29.4-30.3 (16×CH$_2$), 31.9 (CH$_2$), 32.9 (CH$_2$), 33.0 (CH$_2$), 47.7 (CH), 50.0 (CH$_2$), 51.8 (CH), 52.4 (CH), 61.8 (CH$_2$), 64.6 (CH$_2$), 66.4 (CH$_2$), 67.2 (CH$_2$), 67.7 (CH$_2$), 68.3 (CH), 69.8 (CH$_2$), 71.0 (CH), 72.0 (CH), 72.5 (CH), 100.6 (CH), 124.0 (CH), 128.2-128.6 (10×CH), 135.3 (C), 135.9 (C), 144.4 (C), 169.4 (C), 169.5 (C), 170.0 (2×C), 170.6 (C), 171.2 (C), 172.3 (C), 176.5 (C); Mass (ESI+) m/z (%) 1271 (100) [M+Na]$^+$; HRMS (ESI+) m/z calculated for C$_{67}$H$_{101}$N$_5$O$_{17}$Na 1270.7090, found 1270.7128.

Compound 3.5k

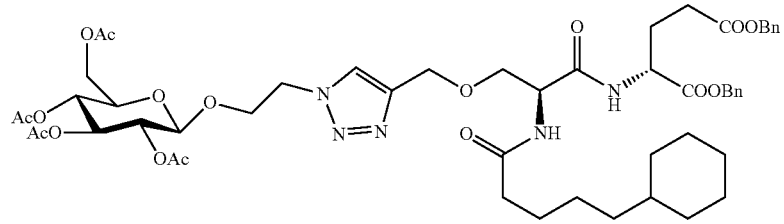

The compound 3.5k (yellowish gum, 200 mg, 0.19 mmol, 80%) was obtained from the compound 3.3j by following the general protocol I.

Rf=0.16 (CH$_2$Cl$_2$/MeOH 97.5:2.5); $^1$H NMR (400 MHz, CD$_3$OD) δ ppm 0.77-0.92 (m, 2H), 1.10-1.25 (m, 6H), 1.25-1.37 (m, 2H), 1.51-1.73 (m, 7H), 1.91, 1.93, 1.98, 2.02 (s, 12H), 1.94-2.08 (m, 1H), 2.14-2.30 (m, 3H), 2.34-2.48 (m, 2H), 3.69 (dd, J=9.6, 5.5 Hz, 1H), 3.78 (dd, J=9.6, 5.2 Hz, 1H), 3.85 (ddd, J=9.7, 4.6, 2.1 Hz, 1H), 3.95 (m, 1H), 4.12 (dd, J=12.4, 2.1 Hz, 1H), 4.12-4.20 (m, 1H), 4.26 (dd, J=12.4, 4.6 Hz, 1H), 4.48-4.64 (m, 6H), 4.66 (d, J=7.9 Hz, 1H), 4.89 (dd, J=9.5, 7.9 Hz, 1H), 5.02 (dd, J=9.7, 9.5 Hz, 1H), 5.09 (s, 2H), 5.12 (d, J=12.5 Hz, 1H), 5.17 (d, J=12.5 Hz, 1H), 5.23 (dd, J=9.5, 9.5 Hz, 1H), 7.25-7.38 (m, 10H), 7.82 (s, 1H); $^{13}$C NMR (100 MHz, CDCl$_3$) δ ppm 20.6 (2×CH$_3$), 20.7 (2×CH$_3$), 27.0 (CH$_2$), 27.4 (2×CH$_2$), 27.5 (CH$_2$), 27.6 (CH$_2$), 27.7 (CH$_2$), 31.0 (CH$_2$), 34.5 (2×CH$_2$), 36.8 (CH$_2$), 38.3 (CH$_2$), 38.7 (CH), 51.2 (CH$_2$), 53.1 (CH), 54.4 (CH), 63.0 (CH$_2$), 65.1 (CH$_2$), 67.4 (CH$_2$), 68.0 (CH$_2$), 68.9 (CH$_2$), 69.7 (CH), 70.9 (CH$_2$), 72.5 (CH), 72.8 (CH), 73.9 (CH), 101.6 (CH), 125.7 (CH), 129.1-129.6 (10×CH), 137.1 (C), 137.5 (C), 145.3 (C), 171.1 (2×C), 171.4 (C), 172.1 (C), 172.2 (C), 172.5 (C), 174.0 (C), 176.1 (C); Mass (ESI+) m/z (%) 1059 (100) [M+Na]$^+$; HRMS (ESI+) m/z calculated for C$_{52}$H$_{70}$N$_5$O$_{17}$ 1036.4767, found 1036.4760.

Compound 3.5l

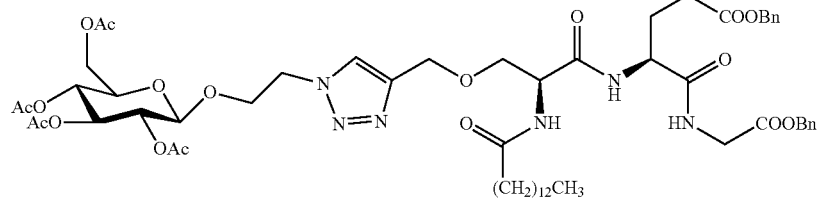

The compound 3.5l (yellowish solid, 153 mg, 0.13 mmol, 61%) was obtained from the compound 3.3k by following the general protocol I.

Rf=0.21 (CH$_2$Cl$_2$/MeOH 97.5:2.5); Tm=60-63° C.; $^1$H NMR (400 MHz, CD$_3$OD) δ ppm 0.89 (t, J=6.9 Hz, 3H), 1.21-1.34 (m, 20H), 1.53-1.65 (m, 2H), 1.92, 1.94, 1.99, 2.02 (s, 12H), 1.93-2.10 (m, 1H), 2.15-2.31 (m, 3H), 2.42-2.52 (m, 2H), 3.71 (dd, J=9.6, 5.2 Hz, 1H), 3.79-3.88 (m, 2H), 3.91-4.00 (m, 3H), 4.09-4.20 (m, 2H), 4.26 (dd, J=12.4, 4.7 Hz, 1H), 4.47-4.64 (m, 6H), 4.66 (d, J=8.0 Hz, 1H), 4.88 (dd, J=9.6, 8.0 Hz, 1H), 5.01 (dd, J=9.6, 9.6 Hz, 1H), 5.11 (s, 2H), 5.15 (s, 2H), 5.23 (dd, J=9.6, 9.6 Hz, 1H), 7.25-7.40 (m, 10H), 7.84 (s, 1H); $^{13}$C NMR (100 MHz, CDCl$_3$) δ ppm 14.6 (CH$_3$), 20.7 (CH$_3$), 20.7 (CH$_3$), 20.8 (CH$_3$), 20.8 (CH$_3$), 23.8 (CH$_2$), 26.8 (CH$_2$), 28.1 (CH$_2$), 30.5-30.9 (8×CH$_2$), 31.2 (CH$_2$), 33.1 (CH$_2$), 36.8 (CH$_2$), 42.2 (CH$_2$), 51.3 (CH$_2$), 53.7 (CH), 55.2 (CH), 63.1 (CH$_2$), 65.3 (CH$_2$), 67.4 (CH$_2$), 68.0 (CH$_2$), 69.0 (CH$_2$), 69.8 (CH), 70.9 (CH$_2$), 72.6 (CH), 73.0 (CH), 74.1 (CH), 101.7 (CH), 125.9 (CH), 129.3-129.7 (10×CH), 137.2 (C), 137.7 (C), 145.3 (C), 171.0 (C), 171.2 (C), 171.3 (C), 171.6 (C), 172.3 (C), 172.3 (C), 173.8 (C), 174.4 (C), 176.9 (C); Mass (ESI+) m/z (%) 1160 (100) [M+Na]$^+$; HRMS (ESI+) m/z calculated for C$_{57}$H$_{81}$N$_6$O$_{18}$ 1137.5607, found 1137.5610.

Compound 3.7a

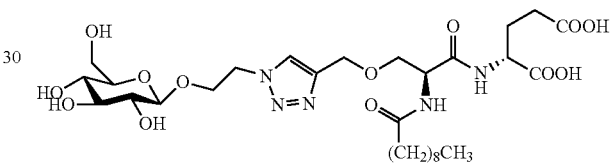

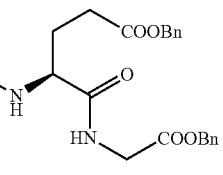

The compound 3.7a (white solid, 81 mg, 0.12 mmol, 70%) was obtained from the compound 3.5a by following the general protocols J then F.

Tm=72-75° C.; $^1$H NMR (400 MHz, CD$_3$OD): δ ppm 0.89 (t, J=6.2 Hz, 3H), 1.20-1.38 (m, 12H), 1.54-1.67 (m, 2H), 1.86-1.99 (m, 1H), 2.10-2.24 (m, 1H), 2.24-2.40 (m, 4H), 3.21 (dd, J=8.9, 8.0 Hz, 1H), 3.25-3.41 (m, 3H), 3.62-3.75 (m, 2H), 3.80 (dd, J=9.6, 5.2 Hz, 1H), 3.87 (dd, J=11.8, 1.3 Hz, 1H), 3.94-4.06 (m, 1H), 4.20-4.29 (m, 1H), 4.32 (d, J=8.0 Hz, 1H), 4.45 (dd, J=8.7, 4.6 Hz, 1H), 4.57-4.71 (m, 5H), 8.14 (s, 1H); $^{13}$C NMR (100 MHz, CD$_3$OD): δ ppm 14.4 (CH$_3$), 23.7 (CH$_2$), 26.8 (CH$_2$), 27.8 (CH$_2$), 30.3, 30.4, 30.4, 30.5 (4×CH$_2$), 30.9 (CH$_2$), 33.0 (CH$_2$), 36.8 (CH$_2$), 51.6 (CH$_2$), 53.0 (CH), 54.5 (CH), 62.6 (CH$_2$), 65.0 (CH$_2$), 69.0 (CH$_2$), 70.8 (CH$_2$), 71.5 (CH), 74.9 (CH), 77.9 (2×CH), 104.4 (CH), 126.2 (CH), 145.2 (C), 172.1 (C), 174.5 (C), 176.4 (2×C); Mass (ESI−) m/z (%) 674 (100) [M−H]$^−$; HRMS (ESI+) m/z calculated for C$_{29}$H$_{50}$N$_5$O$_{13}$ 676.3405, found 676.3409.

Compound 3.7b

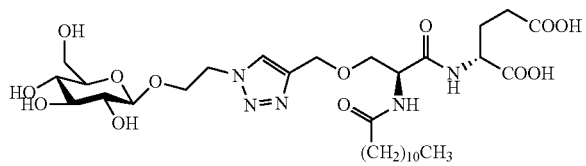

The compound 3.7b (white solid, 108 mg, 0.15 mmol, 93%) was obtained from the compound 3.5b by following the general protocols J then F.

Tm=118-120° C.; $^1$H NMR (400 MHz, CD$_3$OD): δ ppm 0.89 (t, J=5.9 Hz, 3H), 1.16-1.38 (m, 16H), 1.52-1.67 (m, 2H), 1.85-2.00 (m, 1H), 2.10-2.25 (m, 1H), 2.22-2.42 (m, 4H), 3.21 (dd, J=8.4, 7.8 Hz, 1H), 3.23-3.42 (m, 3H), 3.63-3.74 (m, 2H), 3.79 (dd, J=9.6, 5.2 Hz, 1H), 3.87 (dd, J=11.8, 1.3 Hz, 1H), 3.94-4.06 (m, 1H), 4.17-4.28 (m, 1H), 4.32 (d, J=7.8 Hz, 1H), 4.46 (dd, J=8.8, 4.6 Hz, 1H), 4.55-4.70 (m, 5H), 8.10 (s, 1H); $^{13}$C NMR (100 MHz, CD$_3$OD): δ ppm 14.4 (CH$_3$), 23.7 (CH$_2$), 26.8 (CH$_2$), 27.9 (CH$_2$), 30.3-30.7 (6×CH$_2$), 31.0 (CH$_2$), 33.0 (CH$_2$), 36.8 (CH$_2$), 51.6 (CH$_2$), 53.2 (CH), 54.5 (CH), 62.6 (CH$_2$), 65.0 (CH$_2$), 69.0 (CH$_2$), 70.8 (CH$_2$), 71.4 (CH), 74.9 (CH), 77.8 (CH), 77.9 (CH), 104.4 (CH), 126.2 (CH), 145.2 (C), 172.0 (C), 174.8 (C), 176.4 (C), 176.5 (C); Mass (ESI−) m/z (%) 702 (100) [M−H]$^−$; HRMS (ESI+) m/z calculated for C$_{31}$H$_{54}$N$_5$O$_{13}$ 704.3718, found 704.3703.

Compound 3.7c

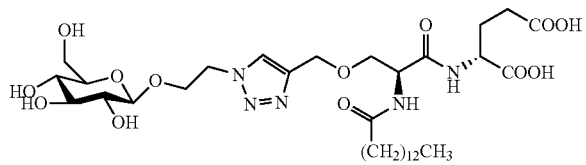

The compound 3.7c (white solid, 358 mg, 0.49 mmol, 75%) was obtained from the compound 3.5c by following the general protocols J then F.

Tm=154-156° C.; $^1$H NMR (400 MHz, CD$_3$OD) δ ppm 0.90 (t, J=6.9 Hz, 3H), 1.21-1.37 (m, 20H), 1.54-1.67 (m, 2H), 1.86-1.99 (m, 1H), 2.13-2.25 (m, 1H), 2.25-2.31 (m, 2H), 2.31-2.38 (m, 2H), 3.19 (dd, J=9.7, 8.0 Hz, 1H), 3.24-3.38 (m, 3H), 3.62-3.68 (m, 1H), 3.71 (dd, J=9.5, 5.4 Hz, 1H), 3.78 (dd, J=9.5, 5.4 Hz, 1H), 3.87 (dd, J=11.8, 1.5 Hz, 1H), 3.96-4.03 (m, 1H), 4.21-4.28 (m, 1H), 4.30 (d, J=7.8 Hz, 1H), 4.47 (dd, J=9.1, 4.7 Hz, 1H), 4.58-4.67 (m, 5H), 8.09 (s, 1H); $^{13}$C NMR (100 MHz, CD$_3$OD) δ ppm 14.4 (CH$_3$), 23.7 (CH$_2$), 26.9 (CH$_2$), 27.9 (CH$_2$), 30.4-30.8 (8×CH$_2$), 31.0 (CH2), 33.1 (CH$_2$), 36.8 (CH$_2$), 51.6 (CH$_2$), 53.1 (CH), 54.5 (CH), 62.7 (CH$_2$), 65.1 (CH$_2$), 69.1 (CH$_2$), 70.8 (CH$_2$), 71.5 (CH), 74.9 (CH), 77.9 (CH), 78.1 (CH), 104.5 (CH), 126.2 (CH), 145.3 (C), 172.1 (2×C), 176.4 (C), 176.5 (C); Mass (ESI−) m/z (%) 365 (30) [M−2H]$^{2−}$, 550 (20), 730 (100) [M−H]$^−$, 752 (20); HRMS (ESI−) m/z calculated for C$_{33}$H$_{56}$N$_5$O$_{13}$ 730.3875, found 730.3886.

Compound 3.7d

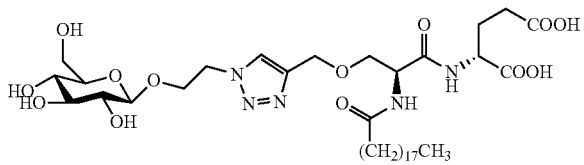

The compound 3.7d (white solid, 74 mg, 0.09 mmol, 77%) was obtained from the compound 3.5d by following the general protocols J then F. (LiOH/Dioxane-H$_2$O).

Tm=175-185° C.; $^1$H NMR (500 MHz, DMSO-d$_6$) δ ppm 0.85 (t, J=6.6 Hz, 3H), 1.11-1.32 (m, 30H), 1.39-1.51 (m, 2H), 1.68-1.83 (m, 1H), 1.90-2.04 (m, 1H), 2.07-2.16 (m, 2H), 2.18-2.29 (m, 2H), 2.96 (dd, J=8.3, 8.3 Hz, 1H), 3.03 (dd, J=8.8, 8.8 Hz, 1H), 3.08-3.17 (m, 2H), 3.34-3.46 (m, 1H), 3.51-3.60 (m, 2H), 3.64-3.70 (m, 1H), 3.85-3.93 (m, 1H), 4.03-4.12 (m, 1H), 4.17-4.28 (m, 2H), 4.44-4.63 (m, 5H), 7.93 (d, J=8.1 Hz, 1H, NH), 8.09 (s, 1H), 8.20 (d, J=7.8 Hz, 1H, NH); $^{13}$C NMR (125 MHz, DMSO-d$_6$) δ ppm 14.0 (CH$_3$), 22.1 (CH$_2$), 25.2 (CH$_2$), 26.5 (CH$_2$), 28.7-29.1 (13×CH$_2$), 29.8 (CH$_2$), 31.3 (CH$_2$), 35.1 (CH$_2$), 49.6 (CH$_2$), 51.1 (CH), 52.2 (CH), 61.1 (CH$_2$), 63.6 (CH$_2$), 67.3 (CH$_2$), 69.9 (CH$_2$), 70.0 (CH), 73.3 (CH), 76.6 (CH), 77.0 (CH), 102.9 (CH), 124.7 (CH), 143.5 (C), 169.6 (C), 172.3 (C), 173.0 (C), 173.8 (C); Mass (ESI−) m/z (%) 399 (95) [M−2H]$^{2−}$, 620 (70), 638 (30), 800 (100) [M−H]$^−$, 822 (85) [M+Na−2H]$^−$; HRMS (ESI−) m/z calculated for C$_{38}$H$_{66}$N$_5$O$_{13}$ 800.4657, found 800.4636.

Compound 3.7e

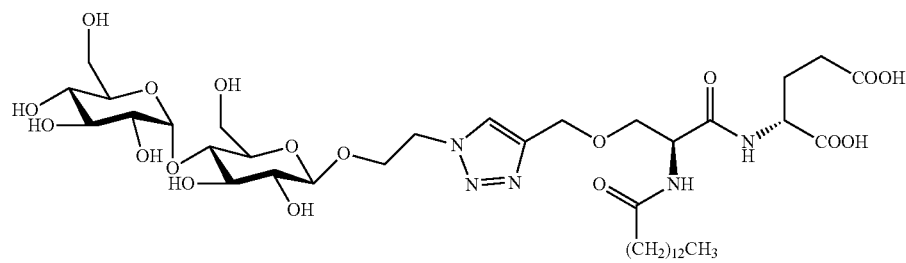

The compound 3.7e (white solid, 163 mg, 0.18 mmol, 79%) was obtained from the compound 3.5d by following the general protocols J then F.

Tm=167-169° C.; $^1$H NMR (400 MHz, CD$_3$OD) δ ppm 0.90 (t, J=6.8 Hz, 3H), 1.22-1.39 (m, 20H), 1.57-1.67 (m, 2H), 1.86-1.98 (m, 1H), 2.13-2.24 (m, 1H), 2.28 (t, J=7.1 Hz, 2H), 2.31-2.40 (m, 2H), 3.22-3.33 (m, 2H), 3.39 (ddd, J=9.2, 4.7, 1.9 Hz, 1H), 3.44 (dd, J=9.7, 3.8 Hz, 1H), 3.53 (dd, J=9.2, 9.2 Hz, 1H), 3.56-3.73 (m, 5H), 3.74-3.92 (m, 4H), 3.95-4.03 (m, 1H), 4.19-4.29 (m, 1H), 4.33 (d, J=7.8 Hz, 1H), 4.46 (dd, J=9.0, 4.6 Hz, 1H), 4.56-4.68 (m, 5H), 5.16 (d, J=3.8 Hz, 1H), 8.09 (s, 1H); $^{13}$C NMR (100 MHz, CD$_3$OD) δ ppm 14.4 (CH$_3$), 23.7 (CH$_2$), 26.8 (CH$_2$), 28.0 (CH$_2$), 30.3-30.8 (8×CH$_2$), 31.0 (CH$_2$), 33.1 (CH$_2$), 36.8 (CH$_2$), 51.6 (CH$_2$), 53.2 (CH), 54.6 (CH), 62.1 (CH$_2$), 62.8 (CH$_2$), 65.1 (CH$_2$), 69.1 (CH$_2$), 70.8 (CH$_2$), 71.5 (CH), 74.1 (CH), 74.5 (CH), 74.8 (CH), 75.0 (CH), 76.7 (CH), 77.7 (CH), 81.1 (CH), 102.9 (CH), 104.5 (CH), 126.2 (CH), 145.3 (C), 172.1 (C), 174.7 (C), 176.4 (C), 176.5 (C); Mass (ESI-) m/z (%) 446 (100) [M-H]$^{2-}$, 892 (100) [M-H]$^-$; HRMS (ESI+) m/z calculated for C$_{39}$H$_{66}$N$_5$O$_{18}$ 892.4403, found 892.4398.

Compound 3.7f

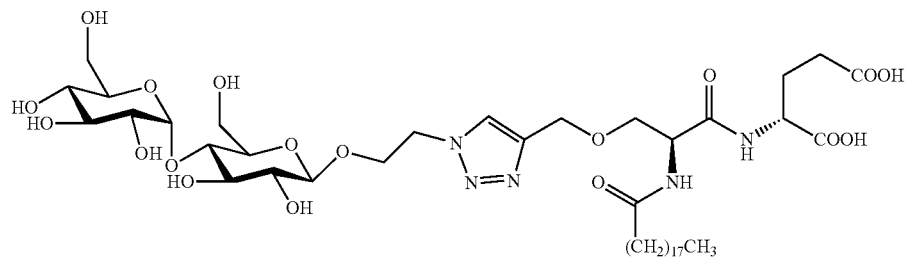

The compound 3.7f (white solid, 101 mg, 0.10 mmol, 92%) was obtained from the compound 3.5e by following the general protocols J then F (LiOH/Dioxane-H$_2$O).

Tm=214-216° C.; $^1$H NMR (500 MHz, CD$_3$OD) δ ppm 0.90 (t, J=7.0 Hz, 3H), 1.23-1.39 (m, 30H), 1.56-1.66 (m, 2H), 1.88-1.97 (m, 1H), 2.15-2.24 (m, 1H), 2.25-2.31 (m, 2H), 2.31-2.39 (m, 2H), 3.22-3.29 (m, 2H), 3.39 (ddd, J=9.4, 4.7, 1.9 Hz, 1H), 3.44 (dd, J=9.7, 3.8 Hz, 1H), 3.53 (dd, J=9.4, 9.2 Hz, 1H), 3.57-3.74 (m, 5H), 3.75-3.85 (m, 3H), 3.89 (dd, J=12.1, 1.9 Hz, 1H), 3.96-4.03 (m, 1H), 4.21-4.27 (m, 1H), 4.33 (d, J=7.8 Hz, 1H), 4.47 (dd, J=9.1, 4.7 Hz, 1H), 4.57-4.69 (m, 5H), 5.16 (d, J=3.8 Hz, 1H), 8.09 (s, 1H); $^{13}$C NMR (125 MHz, CD$_3$OD): δ ppm 14.4 (CH$_3$), 23.7 (CH$_2$), 26.9 (CH$_2$), 27.9 (CH$_2$), 30.4-30.8 (13×CH$_2$), 31.0 (CH$_2$), 33.1 (CH$_2$), 36.8 (CH$_2$), 51.6 (CH$_2$), 53.1 (CH), 54.5 (CH), 62.1 (CH$_2$), 62.8 (CH$_2$), 65.1 (CH$_2$), 69.2 (CH$_2$), 70.9 (CH$_2$), 71.5 (CH), 74.2 (CH), 74.5 (CH), 74.8 (CH), 75.1 (CH), 76.7 (CH), 77.7 (CH), 81.2 (CH), 102.9 (CH), 104.5 (CH), 126.2 (CH), 145.3 (C), 172.2 (C), 174.5 (C), 176.4 (C), 176.5 (C); Mass (ESI-) m/z (%) 481 (55) [M-2H]$^{2-}$, 963 (100) [M-H]$^-$; HRMS (ESI-) m/z calculated for C$_{44}$H$_{76}$N$_5$O$_{18}$ 962.5185, found 962.5211.

Compound 3.7g

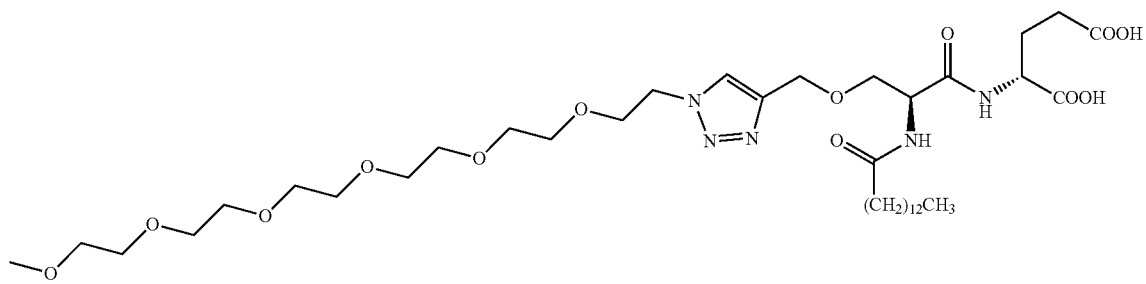

The compound 3.7g (white wax, 41 mg, 0.05 mmol, quantitative) was obtained from the compound 3.5g by following the general protocol D1.

Tm=54-57° C.; $^1$H NMR (500 MHz, CD$_3$OD) δ ppm 0.90 (t, J=7.0 Hz, 3H), 1.23-1.37 (m, 20H), 1.55-1.66 (m, 2H), 1.88-1.98 (m, 1H), 2.13-2.22 (m, 1H), 2.23-2.39 (m, 4H), 3.35 (s, 3H), 3.51-3.55 (m, 2H), 3.56-3.66 (m, 18H), 3.71 (dd, J=9.7, 5.2 Hz, 1H), 3.79 (dd, J=9.7, 5.4 Hz, 1H), 3.90 (t, J=5.1 Hz, 2H), 4.40 (dd, J=8.1, 4.7 Hz, 1H), 4.55-4.67 (m, 5H), 8.03 (s, 1H); $^{13}$C NMR (125 MHz, CD$_3$OD): δ ppm 14.4 (CH$_3$), 23.7 (CH$_2$), 26.8 (CH$_2$), 28.4 (CH$_2$), 30.4-30.8 (8×CH$_2$), 31.2 (CH$_2$), 33.1 (CH$_2$), 36.8 (CH$_2$), 51.4 (CH$_2$), 53.9 (CH), 54.7 (CH), 59.1 (CH$_3$), 65.1 (CH$_2$), 70.3 (CH$_2$), 70.8 (CH$_2$), 71.1-71.3 (9×CH$_2$), 72.8 (CH$_2$), 125.9 (CH), 145.5 (C), 171.7 (2×C), 176.4 (2×C); Mass (ESI+) m/z (%) 827 (100) [M+Na]$^+$, HRMS (ESI+) m/z calculated for C$_{38}$H$_{70}$N$_5$O$_{13}$ 804.4970, found 804.4975.

Compound 3.7h

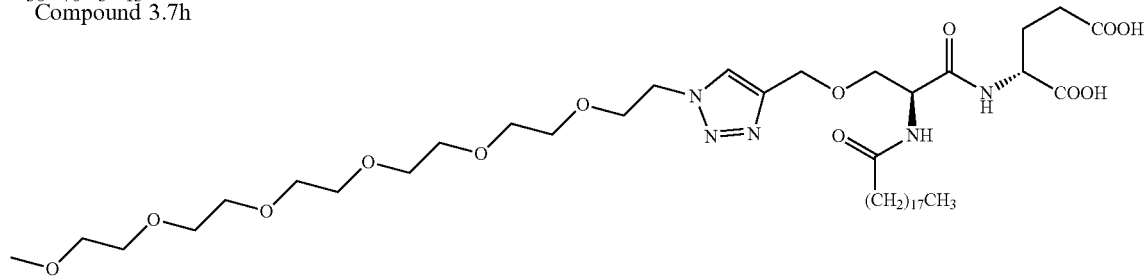

The compound 3.7h (white solid, 58 mg, 0.07 mmol, 89%) was obtained from the compound 3.5h by following the general protocol D1.

Tm=76-79° C.; $^1$H NMR (500 MHz, CD$_3$OD) δ ppm 0.90 (t, J=6.9 Hz, 3H), 1.23-1.38 (m, 30H), 1.56-1.66 (m, 2H), 1.88-1.98 (m, 1H), 2.13-2.22 (m, 1H), 2.23-2.39 (m, 4H), 3.35 (s, 3H), 3.50-3.55 (m, 2H), 3.56-3.67 (m, 18H), 3.71 (dd, J=9.6, 5.3 Hz, 1H), 3.79 (dd, J=9.6, 5.3 Hz, 1H), 3.90 (t, J=5.1 Hz, 2H), 4.42 (dd, J=8.5, 4.8 Hz, 1H), 4.55-4.67 (m, 5H), 8.03 (s, 1H); $^{13}$C NMR (125 MHz, CD$_3$OD): δ ppm 14.5 (CH$_3$), 23.7 (CH$_2$), 26.9 (CH$_2$), 28.2 (CH$_2$), 30.4-30.9 (13×CH$_2$), 31.1 (CH$_2$), 33.1 (CH$_2$), 36.8 (CH$_2$), 51.4 (CH$_2$), 53.6 (CH), 54.6 (CH), 59.1 (CH$_3$), 65.1 (CH$_2$), 70.3 (CH$_2$), 70.9 (CH$_2$), 71.2-71.4 (9×CH$_2$), 72.9 (CH$_2$), 125.9 (CH), 145.4 (C), 171.8 (C), 175.1 (C), 176.4 (C), 176.5 (C); Mass (ESI+) m/z (%) 231 (50), 897 (100) [M+Na]$^+$; HRMS (ESI+) m/z calculated for C$_{43}$H$_{80}$N$_5$O$_{13}$ 874.5753, found 874.5761.

Compound 3.7i

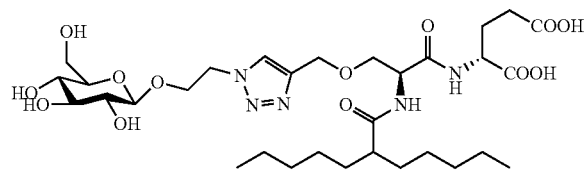

The compound 3.7i (white solid, 31 mg, 0.04 mmol, 46%) was obtained from the compound 3.5i by following the general protocols J then F.

Tm=100-103° C.; $^1$H NMR (400 MHz, CD$_3$OD) δ ppm 0.88 (t, J=6.5 Hz, 6H), 1.18-1.36 (m, 12H), 1.33-1.46 (m, 2H), 1.47-1.68 (m, 2H), 1.86-1.97 (m, 1H), 2.13-2.24 (m, 1H), 2.24-2.40 (m, 3H), 3.20 (dd, J=9.0, 7.9 Hz, 1H), 3.31-3.39 (m, 3H), 3.62-3.73 (m, 2H,), 3.79 (dd, J=9.5, 5.3 Hz, 1H), 3.87 (d, J=11.5, 1.3 Hz, 1H), 3.96-4.04 (m, 1H), 4.21-4.28 (m, 1H), 4.32 (d, J=7.8 Hz, 1H), 4.42 (dd, J=7.8, 4.7 Hz, 1H), 4.59-4.71 (m, 5H), 8.10 (s, 1H); $^{13}$C NMR (100 MHz, CD$_3$OD): δ ppm 14.4 (2×CH$_3$), 23.5 (CH$_2$), 23.6 (CH$_2$), 28.2 (CH$_2$), 28.3 (CH$_2$), 28.5 (CH$_2$), 31.1 (CH$_2$), 32.9 (CH$_2$), 33.1 (CH$_2$), 34.1 (CH$_2$), 48.0 (CH), 51.6 (CH$_2$), 53.5 (CH), 54.4 (CH), 62.7 (CH$_2$), 65.1 (CH$_2$), 69.0 (CH$_2$), 70.9 (CH$_2$), 71.5 (CH), 74.9 (CH), 77.9 (CH), 78.0 (CH), 104.5 (CH), 126.2 (CH), 145.3 (C), 171.7 (C), 175.1 (C), 176.5 (C), 179.2 (C); Mass (ESI−) m/z (%) 351 (25) [M−2H]$^{2-}$, 702 (100) [M−H]$^-$; HRMS (ESI−) m/z calculated for C$_{31}$H$_{52}$N$_5$O$_{13}$ 702.3562, found 702.3550.

Compound 3.7j

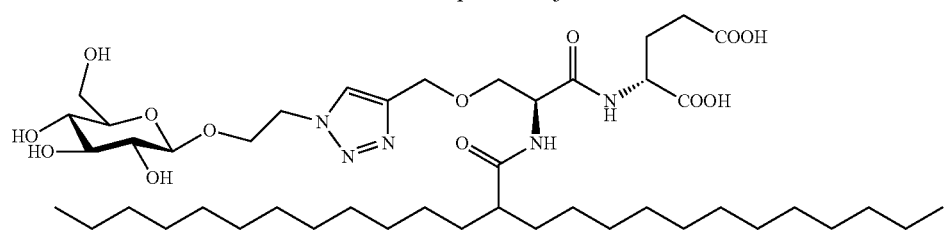

The compound 3.7j (white solid, 40 mg, 0.04 mmol, quantitative) was obtained from the compound 3.5j by following the general protocols J then F (LiOH/Dioxane-H$_2$O).

Tm>160° C. (with decomposition); $^1$H NMR (500 MHz, CD$_3$OD) δ ppm 0.90 (t, J=6.9 Hz, 6H), 1.20-1.36 (m, 40H), 1.36-1.47 (m, 2H), 1.49-1.65 (m, 2H), 1.86-1.97 (m, 1H), 2.14-2.23 (m, 1H), 2.26-2.38 (m, 3H), 3.20 (dd, J=9.1, 7.8 Hz, 1H), 3.26-3.39 (m, 3H), 3.64-3.69 (m, 1H), 3.70 (dd, J=9.7, 5.7 Hz, 1H), 3.78 (dd, J=9.7, 5.3 Hz, 1H), 3.87 (dd, J=11.5, 1.3 Hz, 1H), 3.97-4.03 (m, 1H), 4.21-4.28 (m, 1H), 4.32 (d, J=7.8 Hz, 1H), 4.44 (dd, J=8.3, 4.9 Hz, 1H), 4.61-4.70 (m, 5H), 8.10 (s, 1H); $^{13}$C NMR (100 MHz, CD$_3$OD): δ ppm 14.5 (2×CH$_3$), 23.7 (2×CH$_2$), 28.5 (2×CH$_2$), 28.6 (CH$_2$), 30.5-30.8 (14×CH$_2$), 31.1 (CH$_2$), 33.1 (2×-CH$_2$), 34.0 (2×CH$_2$), 47.9 (CH), 51.6 (CH$_2$), 53.5 (CH), 54.4 (CH), 62.7 (CH$_2$), 65.1 (CH$_2$), 69.0 (CH$_2$), 70.9 (CH$_2$), 71.5 (CH), 74.9 (CH), 77.9 (CH), 78.0 (CH), 104.5 (CH), 126.1 (CH), 145.3 (C), 171.7 (C), 175.0 (C), 176.5 (C), 179.2 (C); Mass (ESI−) m/z (%) 449 (40) [M-2H]$^{2-}$, 899 (100) [M−H]$^−$; HRMS (ESI−) m/z calculated for C$_{45}$H$_{80}$N$_5$O$_{13}$ 898.5753, found 898.5754.

Compound 3.7k

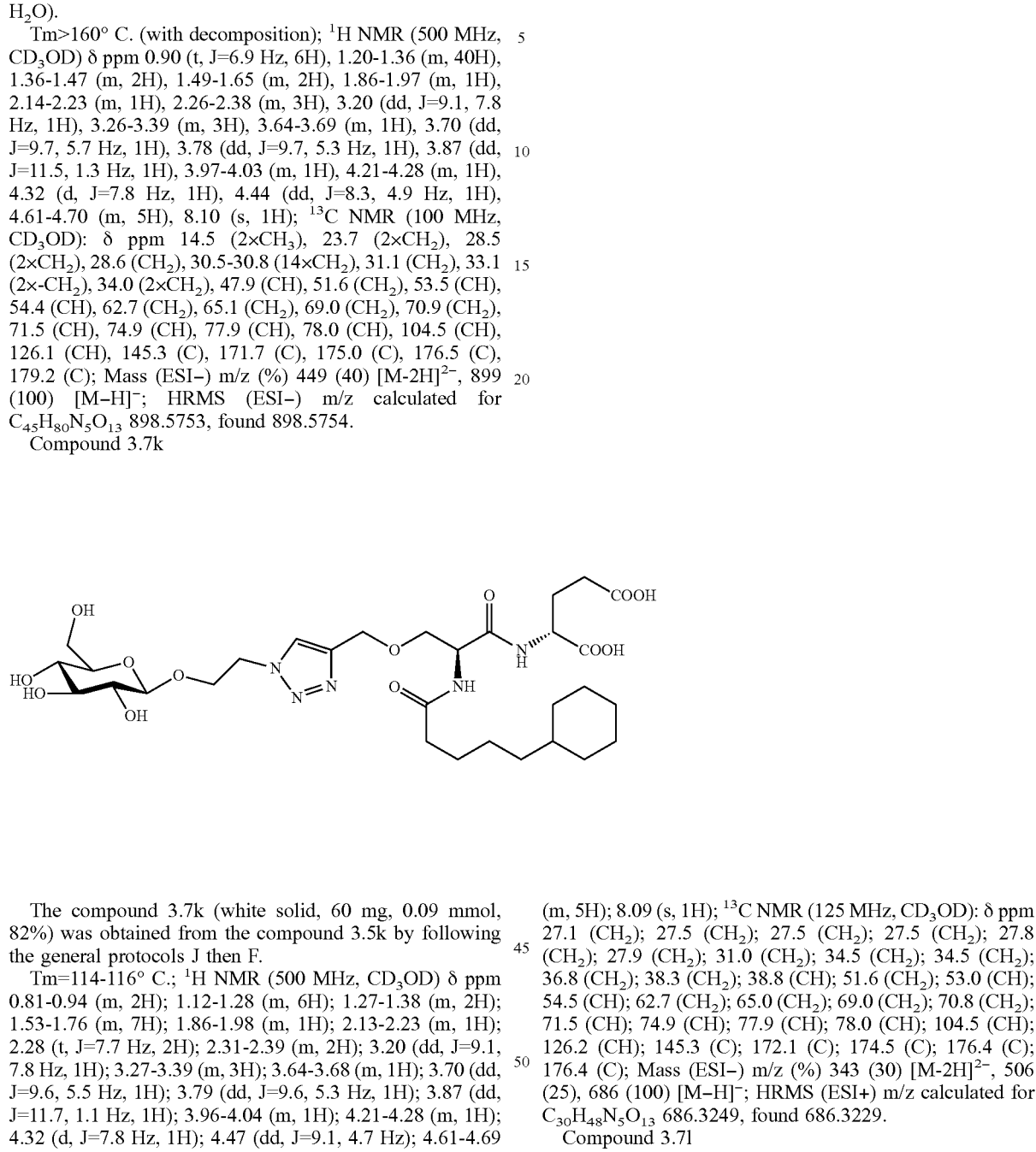

The compound 3.7k (white solid, 60 mg, 0.09 mmol, 82%) was obtained from the compound 3.5k by following the general protocols J then F.

Tm=114-116° C.; $^1$H NMR (500 MHz, CD$_3$OD) δ ppm 0.81-0.94 (m, 2H); 1.12-1.28 (m, 6H); 1.27-1.38 (m, 2H); 1.53-1.76 (m, 7H); 1.86-1.98 (m, 1H); 2.13-2.23 (m, 1H); 2.28 (t, J=7.7 Hz, 2H); 2.31-2.39 (m, 2H); 3.20 (dd, J=9.1, 7.8 Hz, 1H); 3.27-3.39 (m, 3H); 3.64-3.68 (m, 1H); 3.70 (dd, J=9.6, 5.5 Hz, 1H); 3.79 (dd, J=9.6, 5.3 Hz, 1H); 3.87 (dd, J=11.7, 1.1 Hz, 1H); 3.96-4.04 (m, 1H); 4.21-4.28 (m, 1H); 4.32 (d, J=7.8 Hz, 1H); 4.47 (dd, J=9.1, 4.7 Hz); 4.61-4.69 (m, 5H); 8.09 (s, 1H); $^{13}$C NMR (125 MHz, CD$_3$OD): δ ppm 27.1 (CH$_2$); 27.5 (CH$_2$); 27.5 (CH$_2$); 27.5 (CH$_2$); 27.8 (CH$_2$); 27.9 (CH$_2$); 31.0 (CH$_2$); 34.5 (CH$_2$); 34.5 (CH$_2$); 36.8 (CH$_2$); 38.3 (CH$_2$); 38.8 (CH); 51.6 (CH$_2$); 53.0 (CH); 54.5 (CH); 62.7 (CH$_2$); 65.0 (CH$_2$); 69.0 (CH$_2$); 70.8 (CH$_2$); 71.5 (CH); 74.9 (CH); 77.9 (CH); 78.0 (CH); 104.5 (CH); 126.2 (CH); 145.3 (C); 172.1 (C); 174.5 (C); 176.4 (C); 176.4 (C); Mass (ESI−) m/z (%) 343 (30) [M-2H]$^{2-}$, 506 (25), 686 (100) [M−H]$^−$; HRMS (ESI+) m/z calculated for C$_{30}$H$_{48}$N$_5$O$_{13}$ 686.3249, found 686.3229.

Compound 3.7l

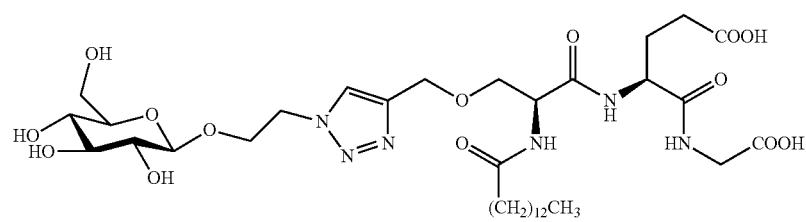

The compound 3.7l (white solid, 70 mg, 0.09 mmol, 94%) was obtained from the compound 3.5l by following the general protocols J then F.

Tm>170° C. (with decomposition); $^1$H NMR (400 MHz, CD$_3$OD) δ ppm 0.90 (t, J=6.8 Hz, 3H), 1.23-1.38 (m, 20H), 1.54-1.67 (m, 2H), 1.86-2.03 (m, 1H), 2.13-2.43 (m, 5H), 3.19 (dd, J=8.9, 7.9 Hz, 1H), 3.25-3.38 (m, 3H), 3.62-3.69 (m, 1H), 3.72 (dd, J=9.7, 4.8 Hz, 1H), 3.82 (dd, J=9.7, 5.3 Hz, 1H), 3.84-3.94 (m, 3H), 3.95-4.05 (m, 1H), 4.20-4.28 (m, 1H), 4.31 (d, J=7.9 Hz, 1H), 4.40-4.70 (m, 6H), 8.11 (s, 1H); $^{13}$C NMR (100 MHz, CD$_3$OD) δ ppm 14.4 (CH$_3$), 23.7 (CH$_2$), 26.8 (CH$_2$), 28.6 (CH$_2$), 30.4-30.8 (8×CH$_2$), 32.8 (CH$_2$), 33.1 (CH$_2$), 36.8 (CH$_2$), 41.9 (CH$_2$), 51.6 (CH$_2$), 53.2 (CH), 54.9 (CH), 62.7 (CH$_2$), 65.1 (CH$_2$), 69.0 (CH$_2$), 70.8 (CH$_2$), 71.5 (CH), 74.9 (CH), 78.0 (CH), 78.0 (CH), 104.5 (CH), 126.3 (CH), 145.3 (C), 172.2 (C), 173.1 (C), 174.5 (C), 175.4 (C), 176.6 (C); Mass (ESI−) m/z (%) 393 (100) [M−H]$^{2-}$, 787 (80) [M−H]$^-$; HRMS (ESI+) m/z calculated for C$_{35}$H$_{61}$N$_6$O$_{14}$ 789.4246, found 789.4238.

Compound 3.8a

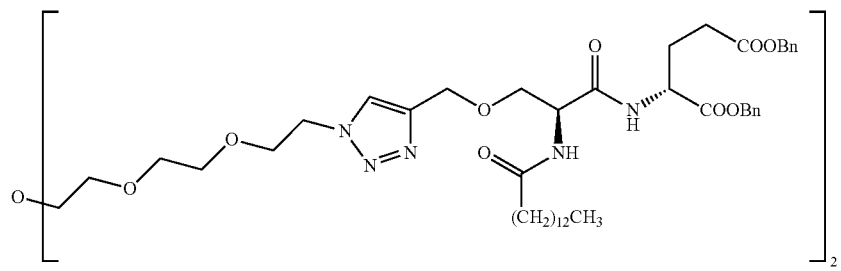

The compound 3.8a (white wax, 162 mg, 0.10 mmol, 43%) was obtained from the compound 3.3f and 1,17-diazido-3,6,9,12,15-pentaoxaheptadecane (not described) by following the general protocol I.

Rf=0.15 (CH$_2$Cl$_2$/MeOH 96:4); $^1$H NMR (500 MHz, CDCl$_3$) δ ppm 0.87 (t, J=6.9 Hz, 6H), 1.18-1.34 (m, 40H), 1.53-1.67 (m, 4H), 1.94-2.08 (m, 2H), 2.13-2.29 (m, 6H), 2.29-2.51 (m, 4H), 3.49-3.66 (m, 18H), 3.79-3.89 (m, 4H), 3.87-4.06 (m, 2H), 4.39-4.53 (m, 4H), 4.53-4.79 (m, 8H), 5.07 (s, 4H), 5.12 (d, J=12.5 Hz, 2H), 5.15 (d, J=12.5 Hz, 2H), 6.67 (bs, 2H, NH), 7.24-7.39 (m, 20H), 7.45 (s, 2H), 7.73 (bs, 2H, NH); $^{13}$C NMR (125 MHz, CDCl$_3$) δ ppm 14.2 (2×CH$_3$), 22.8 (2×CH$_2$), 25.7 (2×CH$_2$), 27.1 (2×CH$_2$), 29.4-29.8 (16×CH$_2$), 30.1 (2×CH$_2$), 32.0 (2×CH$_2$), 36.6 (2×CH$_2$), 50.5 (2×CH$_2$), 52.0 (2×CH), 52.6 (2×CH), 64.5 (2×CH$_2$), 66.6 (2×CH$_2$), 67.3 (2×CH$_2$), 69.4 (2×CH$_2$), 69.6 (2×CH$_2$), 70.6 (8×CH$_2$), 123.9 (2×CH), 128.3-128.7 (20×CH), 135.4 (2×C), 135.9 (2×C), 144.2 (2×C), 170.2 (2×C), 171.3 (2×C), 172.6 (2×C), 173.7 (2×C); Mass (ESI+) m/z (%) 721 (30), 1072 (100), 1680 (75) [M+Na]$^+$, HRMS (ESI+) m/z calculated for C$_{90}$H$_{133}$N$_{10}$O$_{19}$ 1657.9748, found 1657.9785.

Compound 3.9a

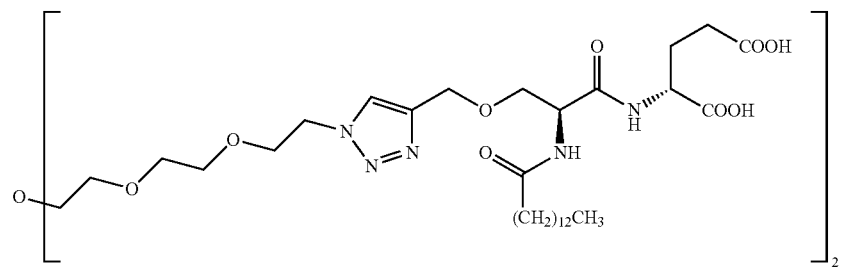

The compound 3.9a (white solid, 107 mg, 0.08 mmol, 95%) was obtained from the compound 3.8a by following the general protocol D1.

Tm=74-76° C.; $^1$H NMR (500 MHz, CD$_3$OD) δ ppm 0.90 (t, J=6.9 Hz, 6H), 1.22-1.37 (m, 40H), 1.56-1.66 (m, 4H), 1.85-2.00 (m, 2H), 2.13-2.25 (m, 2H), 2.24-2.32 (m, 4H), 2.29-2.42 (m, 4H), 3.53-3.66 (m, 16H), 3.68-3.75 (m, 2H), 3.75-3.83 (m, 2H), 3.89 (t, J=4.9 Hz, 4H), 4.37-4.51 (m, 2H), 4.57 (t, J=4.9 Hz, 4H), 4.59-4.69 (m, 6H), 8.04 (s, 2H); $^{13}$C NMR (125 MHz, CD$_3$OD) δ ppm 14.5 (2×CH$_3$), 23.7 (2×CH$_2$), 26.8 (2×CH$_2$), 28.1 (2×CH$_2$), 29.3-29.7 (16×CH$_2$), 31.1 (2×CH$_2$), 33.1 (2×CH$_2$), 36.8 (2×CH$_2$), 51.4 (2×CH$_2$), 52.2 (2×CH), 54.6 (2×CH), 65.1 (2×CH$_2$), 70.3 (2×CH$_2$), 70.9 (2×CH$_2$), 71.4-71.5 (8×CH$_2$), 126.0 (2×CH), 145.4 (2×C), 171.9 (2×C), 174.9 (2×C), 176.4 (2×C), 176.4 (2×C); Mass (ESI−) m/z (%) 647 (100) [M−2H]$^{2-}$; HRMS (ESI+) m/z calculated for C$_{62}$H$_{109}$N$_{10}$O$_{19}$ 1297.7870, found 1297.7860.

Example 5: Compounds 4.1 to 4.6

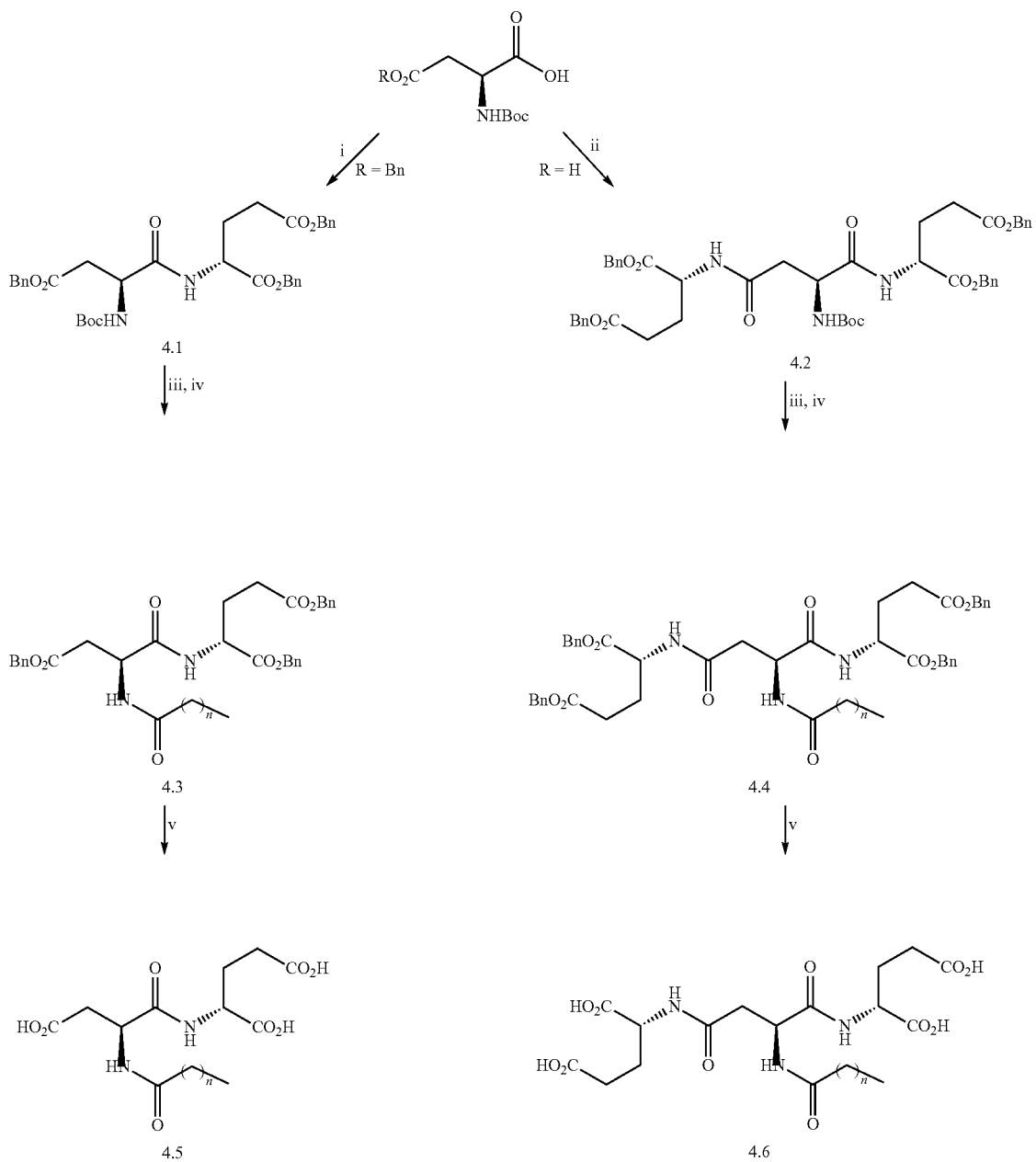

i. H-D-Glu(OBn)-OBn.p-tosylate (2 equiv.), TBTU (1.2 equiv.), DIEA (5 equiv.) DMF;
ii. H-D-Glu(OBn)-OBn.p-tosylate (3 equiv.), TBTU (1.2 equiv.), DIEA (10 equiv.), DMF;
iii. TFA, CH$_2$Cl$_2$;
iv. CH$_3$(CH$_2$)$_n$COCl, DMAP, pyridine, CH$_2$Cl$_2$;
v. Pd/C 5%, THF.

Compound 4.1

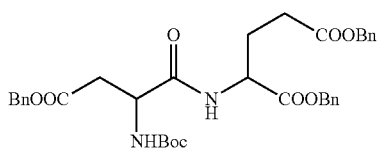

All the reagents, N-Boc-L-aspartic acid 4-benzyl ester (2.00 g, 6.19 mmol), H-D-Glu(OBn)-OBn.p-tosylate (6.18 g, 12.37 mmol, 2 equiv.), TBTU (2.39 g, 7.43 mmol, 1.2 equiv.) and DIEA (4.0 g, 30.9 mmol, 5 equiv.), are solubilized in DMF (80 ml). After 16 h of stirring at RT, the reaction medium is diluted with water and extracted with EtOAc. The combined organic phases are washed with a saturated solution of NaHCO$_3$, in water, with a saturated aqueous solution of NaCl, then dried over MgSO$_4$ and concentrated under vacuum. The residue is dissolved in a minimal amount of CH$_2$Cl$_2$ and the product is precipitated with ether under cold conditions. The precipitate is recovered by filtration on a Büchner funnel using a filter paper, to give 2.07 g of a white solid with 53% yield.

Rf=0.44 (cyclohexane/EtOAc 7:3); Tm=102° C.; $^1$H NMR (400 MHz, CDCl$_3$) δ ppm 1.44 (s, 9H), 1.95-2.06 (m, 1H), 2.18-2.47 (m, 3H), 2.72 (dd, J=17.0, 5.9 Hz, 1H), 3.01 (dd, J=17.1, 4.0 Hz, 1H), 4.50-4.59 (m, 1H), 4.59-4.66 (m, 1H), 5.05-5.20 (m, 6H), 5.63 (d, J=8.1 Hz, NH), 7.16 (d, J=7.3 Hz, NH), 7.28-7.41 (m, 15H); $^{13}$C NMR (100 MHz, CDCl$_3$) δ ppm 27.2 (CH$_2$), 28.2 (3×CH$_3$), 30.0 (CH$_2$), 35.8 (CH$_2$), 50.6 (CH), 51.8 (CH), 66.5 (CH$_2$), 66.8 (CH$_2$), 67.3 (CH$_2$), 80.7 (C), 128.1-128.7 (15×CH), 135.1 (C), 135.4 (C), 135.7 (C), 155.6 (C), 170.7 (C), 171.1 (C), 171.5 (C), 172.4 (C); Mass (ESI+) m/z (%) 655 (100) [M+Na]$^+$; HRMS (ESI+) m/z calculated for C$_{35}$H$_{40}$N$_2$O$_9$Na 655.2632 [M+Na]$^+$, found 655.2624.

Compound 4.2

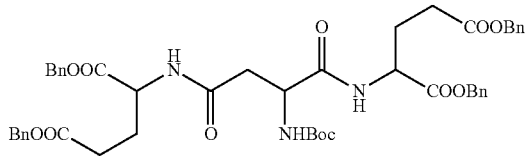

All the reagents, N-Boc-L-aspartic acid (1.00 g, 4.28 mmol), H-D-Glu(OBn)-OBn.p-tosylate (6.22 g, 12.84 mmol, 3 equiv.), TBTU (3.3 g, 10.27 mmol, 1.2 equiv.) and DIPEA (5.54 g, 42.8 mmol, 10 equiv.), are solubilized in DMF (60 ml). After 16 h of stirring at RT, the reaction medium is diluted with water and extracted with EtOAc. The combined organic phases are washed with a saturated solution of NaHCO$_3$, in water, with a saturated aqueous solution of NaCl, then dried over MgSO$_4$ and concentrated under vacuum. The residue is dissolved in a minimal amount of CH$_2$Cl$_2$ and the product is precipitated with ether under cold conditions. The precipitate is recovered by filtration on a Büchner funnel using a filter paper, to give 3.13 g of a white solid with 86% yield.

Rf=0.56 (CH$_2$Cl$_2$/EtOAc 8:2); Tm=89° C.; $^1$H NMR (400 MHz, CDCl$_3$) δ ppm 1.43 (s, 9H), 1.93-2.05 (m, 2H), 2.15-2.28 (m, 2H), 2.29-2.45 (m, 4H), 2.47-2.56 (m, 1H), 2.79-2.89 (m, 1H), 4.47 (m, 1H), 4.54-4.62 (m, 2H), 5.07 (s, 4H), 5.11 (s, 4H), 5.96 (d, J=5.5 Hz, NH), 6.78 (d, J=7.4 Hz, NH), 7.38-7.27 (m, 20H), 7.41 (d, J=7.0 Hz, NH); $^{13}$C NMR (100 MHz, CDCl$_3$) δ ppm 26.8 (CH$_2$), 27.0 (CH$_2$), 28.4 (3×CH$_3$), 30.2 (CH$_2$), 30.3 (CH$_2$), 37.5 (CH$_2$), 51.5 (CH), 52.0 (CH), 52.1 (CH), 66.6 (CH$_2$), 66.7 (CH$_2$), 67.4 (CH$_2$), 67.6 (CH$_2$), 80.6 (C), 128.3-128.8 (20×CH), 135.2 (C), 135.3 (C), 135.8 (C), 135.9 (C), 155.9 (C), 170.8 (2×C), 171.4 (C), 171.7 (C), 172.5 (C), 172.6 (C); Mass (ESI−) m/z (%) 850.4 [M−H]$^-$, 886.4 (100) [M+Cl]$^-$; HRMS (ESI−) m/z calculated for C$_{47}$H$_{52}$N$_3$O$_{12}$ 850.3551 [M−H]$^-$, found 850.3510.

Compound 4.3a

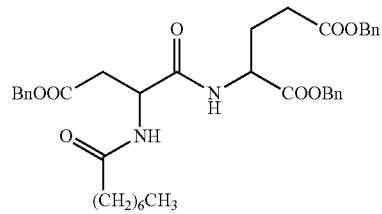

The compound 4.3a (white solid, 431 mg, 0.63 mmol, 79%) was obtained from the compound 4.1 by following the general protocols G then C.

Rf=0.30 (cyclohexane/EtOAc 7:3); Tm=87° C.; $^1$H NMR (400 MHz, CDCl$_3$) δ ppm 0.88 (t, J=6.9 Hz, 3H), 1.15-1.36 (m, 12H), 1.50-1.64 (m, 2H), 1.94-2.05 (m, 1H), 2.14 (t, J=7.4 Hz, 2H), 2.14-2.45 (m, 3H), 2.76-2.92 (m, 2H, H3'), 4.59-4.67 (m, 1H), 4.96-5.02 (m, 1H), 5.03-5.16 (m, 6H), 7.13 (d, J=7.7 Hz, NH), 7.20-7.36 (m, 15H), 7.60 (d, J=7.5 Hz, NH); $^{13}$C NMR (100 MHz, CDCl$_3$) δ ppm 13.9 (CH$_3$), 22.5 (CH$_2$), 25.3 (CH$_2$), 26.7 (CH$_2$), 29.8 (CH$_2$), 29.0-29.3 (4×CH$_2$), 31.7 (CH$_2$), 35.8 (CH$_2$), 36.0 (CH$_2$), 49.0 (CH), 51.7 (CH), 66.2 (CH$_2$), 66.4 (CH$_2$), 66.9 (CH$_2$), 127.9-128.4 (15×CH), 135.1 (C), 135.4 (C), 135.6 (C), 170.6 (C), 170.8 (C), 170.9 (C), 172.2 (C), 173.5 (C); Mass (ESI+) m/z (%) 687 [M+H]$^+$, 709 (100) [M+Na]$^+$, HRMS (ESI+) m/z calculated for C$_{40}$H$_{51}$N$_2$O$_8$Na 709.3465 [M+Na]$^+$, found 709.3461.

Compound 4.3b

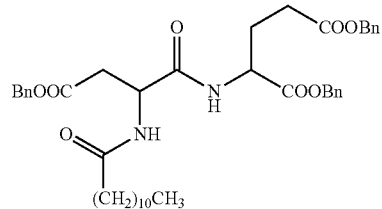

The compound 4.3b (white solid, 424 mg, 0.59 mmol, 75%) was obtained from the compound 4.1 by following the general protocols G then C.

Rf=0.31 (cyclohexane/EtOAc7:3); Tm=75° C.; $^1$H NMR (400 MHz, CDCl$_3$) δ ppm 0.88 (t, J=6.8 Hz, 3H), 1.15-1.36 (m, 16H), 1.50-1.64 (m, 2H), 1.93-2.04 (m, 1H), 2.13 (t, J=7.6 Hz, 2H), 2.14-2.45 (m, 3H), 2.73-2.93 (m, 2H), 4.57-4.66 (m, 1H), 4.91-5.00 (m, 1H), 5.01-5.16 (m, 6H), 7.01 (bs, NH), 7.22-7.36 (m, 15H), 7.50 (bs, NH); $^{13}$C NMR (100 MHz, CDCl$_3$) δ ppm 14.0 (CH$_3$), 22.5 (CH$_2$), 25.4 (CH$_2$), 26.8 (CH$_2$), 29.0-29.6 (6×CH$_2$), 29.9 (CH$_2$), 31.8 (CH$_2$), 35.7 (CH$_2$), 36.1 (CH$_2$), 49.1 (CH), 51.7 (CH), 66.3 (CH$_2$), 66.6 (CH$_2$), 67.0 (CH$_2$), 127.9-128.5 (15×CH), 135.2 (C), 135.4 (C), 135.7 (C), 170.5 (C), 171.0 (2×C), 172.3 (C), 173.6 (C); Mass (ESI+) m/z (%) 715 [M+H]+, 737 (100) [M+Na]+; HRMS (ESI+) m/z calculated for $C_{42}H_{54}N_2O_8Na$ 737.3778 [M+Na]+, found 737.3781.

Compound 4.3c

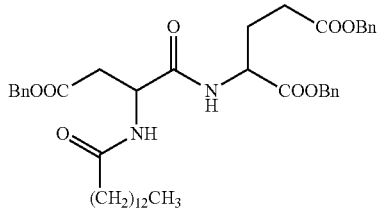

The compound 4.3c (white solid, 523 mg, 0.71 mmol, 86%) was obtained from the compound 4.1 by following the general protocols G then C.

Rf=0.34 (cyclohexane/EtOAc 7:3); Tm=75° C.; $^1$H NMR (400 MHz, CDCl$_3$) δ ppm 0.88 (t, J=6.9 Hz, 3H), 1.16-1.36 (m, 20H), 1.49-1.65 (m, 2H), 1.93-2.04 (m, 1H), 2.13 (t, J=7.7 Hz, 2H), 2.16-2.45 (m, 3H), 2.74-2.91 (m, 2H), 4.57-4.65 (m, 1H), 4.95-5.02 (m, 1H), 5.02-5.14 (m, 6H), 7.17 (d, J=8.4 Hz, NH), 7.20-7.34 (m, 15H), 7.61 (d, J=8.0 Hz, NH); $^{13}$C NMR (100 MHz, CDCl$_3$) δ ppm 14.0 (CH$_3$), 22.6 (CH$_2$), 25.4 (CH$_2$), 26.7 (CH$_2$), 29.0-29.6 (8×CH$_2$), 29.9 (CH$_2$), 31.8 (CH$_2$), 35.8 (CH$_2$), 36.1 (CH$_2$), 49.1 (CH), 51.8 (CH), 66.3 (CH$_2$), 66.5 (CH$_2$), 67.0 (CH$_2$), 127.9-128.5 (15×CH), 135.2 (C), 135.4 (C), 135.7 (C), 170.7 (C), 170.9 (2×C), 172.3 (C), 173.7 (C); Mass (ESI+) m/z (%) 743 [M+H]+, 765 (100) [M+Na]+; HRMS (ESI+) m/z calculated for $C_{44}H_{58}N_2O_8Na$ 765.4091 [M+Na]+, found 765.4079.

Compound 4.3d

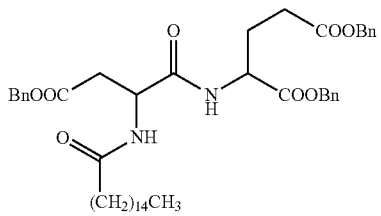

The compound 4.3d (white solid, 523 mg, 0.68 mmol, 89%) was obtained from the compound 4.1 by following the general protocols G then C.

Rf=0.37 (cyclohexane/EtOAc 7:3); Tm=85-86° C.; $^1$H NMR (400 MHz, CDCl$_3$) δ ppm 0.88 (t, J=6.8 Hz, 3H), 1.15-1.35 (m, 24H), 1.49-1.63 (m, 2H), 1.92-2.04 (m, 1H), 2.12 (t, J=7.6 Hz, 2H), 2.13-2.45 (m, 3H), 2.73-2.93 (m, 2H), 4.57-4.65 (m, 1H), 4.92-5.01 (m, 1H), 5.01-5.14 (m, 6H), 7.17 (bs, NH), 7.19-7.36 (m, 15H), 7.61 (bs, NH); $^{13}$C NMR (100 MHz, CDCl$_3$) δ ppm 14.0 (CH$_3$), 22.5 (CH$_2$), 25.4 (CH$_2$), 26.7 (CH$_2$), 29.0-29.6 (11×CH$_2$), 29.9 (CH$_2$), 31.8 (CH$_2$), 35.7 (CH$_2$), 36.1 (CH$_2$), 49.1 (CH), 51.7 (CH), 66.1 (CH$_2$), 66.5 (CH$_2$), 67.0 (CH$_2$), 127.9-128.5 (15×CH), 135.2 (C), 135.4 (C), 135.7 (C), 170.6 (C), 171.0 (2×C), 172.2 (C), 173.5 (C); Mass (ESI+) m/z (%) 793 (100) [M+Na]+; HRMS (ESI+) m/z calculated for $C_{46}H_{62}N_2O_8Na$ 793.4404 [M+Na]+, found 793.4420.

Compound 4.4a

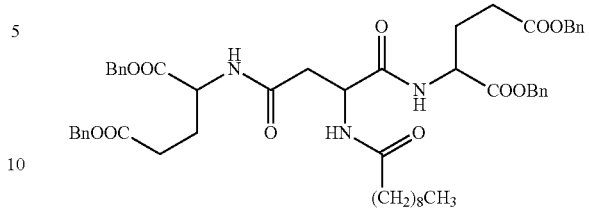

The compound 4.4a (white solid, 437 mg, 0.48 mmol, 82%) was obtained from the compound 4.2 by following the general protocols G then C.

Rf=0.27 (CH$_2$Cl$_2$/EtOAc 8:2); Tm=130-133° C.; $^1$H NMR (400 MHz, CDCl$_3$) δ ppm 0.88 (t, J=6.8 Hz, 3H), 1.18-1.38 (m, 12H), 1.56-1.67 (m, 2H), 1.94-2.06 (m, 2H), 2.16-2.28 (m, 4H), 2.30-2.48 (m, 5H), 2.88 (dd, J=14.9, 3.2 Hz, 1H), 4.52-4.63 (m, 2H), 4.73-4.80 (m, 1H), 5.04-5.17 (m, 8H), 6.93 (d, J=7.5 Hz, NH), 7.13 (d, J=7.5 Hz, NH), 7.27-7.38 (m, 10H), 7.51 (d, J=7.6 Hz, NH); $^{13}$C NMR (100 MHz, CDCl$_3$) δ ppm 14.1 (CH$_3$), 22.7 (CH$_2$), 25.5 (CH$_2$), 26.6 (CH$_2$), 26.8 (CH$_2$), 29.2-29.5 (3×CH$_2$), 30.1 (CH$_2$), 30.2 (CH$_2$), 31.9 (2×CH$_2$), 36.4 (CH$_2$), 37.1 (CH$_2$), 49.9 (CH), 51.9 (CH), 52.1 (CH), 66.5 (2×CH$_2$), 67.2 (CH$_2$), 67.4 (CH$_2$), 128.1-128.7 (20×CH), 135.2 (C), 135.3 (C), 135.8 (2×C), 170.0 (C), 171.1 (C), 171.3 (C), 171.8 (C), 172.3 (C), 172.5 (C), 174.1 (C); Mass (ESI+) m/z (%) 907 [M+H]+, 929 (100) [M+Na]+; HRMS (ESI+) m/z calculated for $C_{52}H_{63}N_3O_{11}Na$ 928.4360 [M+Na]+, found 928.4380.

Compound 4.4b

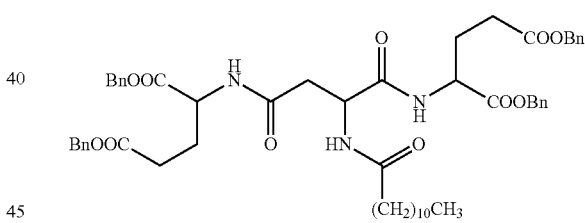

The compound 4.4b (white solid, 430 mg, 0.46 mmol, 78%) was obtained from the compound 4.2 by following the general protocols G then C.

Rf=0.33 (CH$_2$Cl$_2$/EtOAc 8:2); Tm=112-114° C.; $^1$H NMR (400 MHz, CDCl$_3$) δ ppm 0.87 (t, J=6.9 Hz, 3H), 1.17-1.37 (m, 16H), 1.56-1.67 (m, 2H), 1.94-2.07 (m, 2H), 2.16-2.28 (m, 4H), 2.30-2.47 (m, 5H), 2.87 (dd, J=14.9, 3.3 Hz, 1H), 4.52-4.63 (m, 2H), 4.74-4.80 (m, 1H), 5.04-5.17 (m, 8H), 6.96 (d, J=7.5 Hz, NH), 7.14 (d, J=7.5 Hz, NH), 7.27-7.38 (m, 10H), 7.52 (d, J=7.6 Hz, NH); $^{13}$C NMR (100 MHz, CDCl$_3$) δ ppm 14.1 (CH$_3$), 22.6 (CH$_2$), 25.5 (CH$_2$), 26.7 (2×CH$_2$), 29.2-29.7 (5×CH$_2$), 30.0 (CH$_2$), 30.2 (CH$_2$), 31.8 (2×CH$_2$), 36.3 (CH$_2$), 37.1 (CH$_2$), 49.9 (CH), 51.8 (CH), 52.0 (CH), 66.4 (2×CH$_2$), 67.1 (CH$_2$), 67.2 (CH$_2$), 128.0-128.6 (20×CH), 135.1 (C), 135.2 (C), 135.7 (C), 135.8 (C), 170.9 (C), 171.0 (C), 171.3 (C), 171.7 (C), 172.3 (C), 172.4 (C), 174.0 (C); Mass (ESI+) m/z (%) 935 [M+H]+, 957 (100) [M+Na]+; HRMS (ESI+) m/z calculated for $C_{54}H_{67}N_3O_{11}Na$ 956.4673 [M+Na]+, found 956.4682.

Compound 4.4c

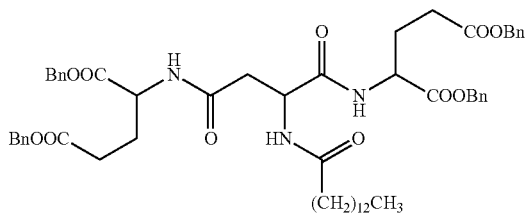

The compound 4.4c (white solid, 437 mg, 0.45 mmol, 77%) was obtained from the compound 4.2 by following the general protocols G then C.

Rf=0.39 (CH$_2$Cl$_2$/EtOAc 8:2); Tm=112-116° C.; $^1$H NMR (400 MHz, CDCl$_3$) δ ppm 0.88 (t, J=7.0 Hz, 3H), 1.16-1.35 (m, 20H), 1.56-1.65 (m, 2H), 1.93-2.06 (m, 2H), 2.15-2.28 (m, 4H), 2.30-2.47 (m, 5H), 2.87 (dd, J=14.9, 3.0 Hz, 1H), 4.51-4.63 (m, 2H), 4.72-4.80 (m, 1H), 5.05-5.14 (m, 8H), 6.94 (d, J=7.4 Hz, NH), 7.11 (d, J=7.5 Hz, NH), 7.27-7.38 (m, 10H), 7.50 (d, J=7.7 Hz, NH); $^{13}$C NMR (100 MHz, CDCl$_3$) δ ppm 14.3 (CH$_3$), 22.8 (CH$_2$), 25.6 (CH$_2$), 26.7 (CH$_2$), 26.9 (CH$_2$), 29.3-29.9 (7×CH$_2$), 30.3 (CH$_2$), 30.4 (CH$_2$), 32.1 (2×CH$_2$), 36.6 (CH$_2$), 37.2 (CH$_2$), 49.9 (CH), 52.2 (CH), 52.3 (CH), 66.7 (2×CH$_2$), 67.4 (CH$_2$), 67.6 (CH$_2$), 128.3-128.9 (20×CH), 135.2 (C), 135.3 (C), 135.9 (2×C), 171.2 (2×C), 171.3 (C), 171.9 (C), 172.5 (C), 172.6 (C), 174.1 (C); Mass (ESI+) m/z (%) 963 (100) [M+H]$^+$, 985 [M+Na]$^+$; HRMS (ESI+) m/z calculated for C$_{56}$H$_{71}$N$_3$O$_{11}$Na 984.4986 [M+Na]$^+$, found 984.4996.

Compound 4.4d

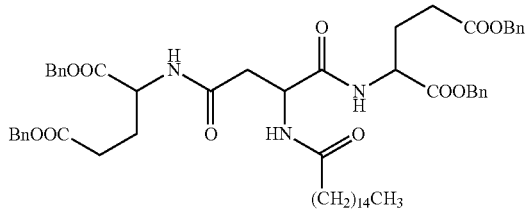

The compound 4.4d (white solid, 436 mg, 0.44 mmol, 75%) was obtained from the compound 4.2 by following the general protocols G then C.

Rf=0.42 (CH$_2$Cl$_2$/EtOAc 8:2); Tm=120-124° C.; $^1$H NMR (400 MHz, CDCl$_3$) δ ppm 0.88 (t, J=7.0 Hz, 3H), 1.19-1.35 (m, 24H), 1.55-1.66 (m, 2H), 1.94-2.07 (m, 2H), 2.16-2.28 (m, 4H), 2.29-2.50 (m, 5H), 2.88 (dd, J=14.9, 3.3 Hz, 1H), 4.52-4.64 (m, 2H), 4.73-4.81 (m, 1H), 5.04-5.17 (m, 8H), 6.99 (d, J=7.5 Hz, NH), 7.16 (d, J=7.5 Hz, NH), 7.27-7.38 (m, 20H), 7.53 (d, J=7.6 Hz, NH); $^{13}$C NMR (100 MHz, CDCl$_3$) δ ppm 14.3 (CH$_3$), 22.8 (CH$_2$), 25.6 (CH$_2$), 26.7 (CH$_2$), 26.9 (CH$_2$), 29.3-29.9 (11×CH$_2$), 30.3 (CH$_2$), 30.4 (CH$_2$), 32.1 (2×CH$_2$), 36.6 (CH$_2$), 37.2 (CH$_2$), 49.9 (CH), 52.2 (2×CH), 66.6 (CH$_2$), 66.7 (CH$_2$), 67.4 (CH$_2$), 67.6 (CH$_2$), 128.3-128.8 (20×CH), 135.2 (C), 135.3 (C), 135.8 (C), 135.9 (C), 171.2 (2×C), 171.3 (C), 171.9 (C), 172.5 (C), 172.6 (C), 174.2 (C); Mass (ESI+) m/z (%) 991 (100) [M+H]$^+$, 1013 [M+Na]$^+$; HRMS (ESI+) m/z calculated for C$_{58}$H$_{75}$N$_3$O$_{11}$Na 1012.5299 [M+Na]$^+$, found 1012.5296.

Compound 4.5a

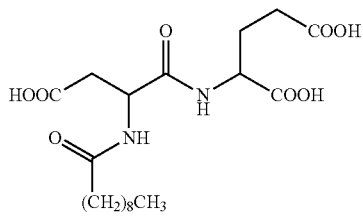

The compound 4.5a (white solid, 175 mg, 0.42 mmol, 72%) was obtained from the compound 4.3a by following the general protocol D2.

Tm=160-162° C.; $^1$H NMR (400 MHz, MeOD) δ ppm 0.90 (t, J=6.8 Hz, 3H), 1.22-1.39 (m, 12H), 1.55-1.68 (m, 2H), 1.90-2.02 (m, 1H), 2.14-2.24 (m, 1H), 2.25 (t, J=7.5 Hz, 2H), 2.36-2.42 (m, 2H), 2.66 (dd, J=16.7, 7.3 Hz, 1H), 2.85 (dd, J=16.7, 6.4 Hz, 1H), 4.43 (dd, J=8.8, 4.8 Hz, 1H), 4.79 (dd, J=7.3, 6.4 Hz, 1H); $^{13}$C NMR (100 MHz, MeOD) δ ppm 14.4 (CH$_3$), 23.7 (CH$_2$), 26.8 (CH$_2$), 27.9 (CH$_2$), 33.0 (CH$_2$), 30.2-31.1 (4×CH$_2$), 36.7 (CH$_2$), 36.9 (CH$_2$), 51.1 (CH), 53.2 (CH), 173.0 (C), 173.8 (C), 174.5 (C), 176.4 (C), 176.5 (C); Mass (ESI−) m/z (%) 397 (100) [M-F]$^-$, 415 [M−H]$^-$, 437 [M+Na-2H]$^-$; HRMS (ESI−) m/z calculated for C$_{19}$H$_{31}$N$_2$O$_3$ 415.2080 [M−H]$^-$, found 415.2093.

Compound 4.5b

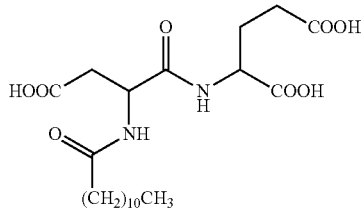

The compound 4.5b (white solid, 190 mg, 0.43 mmol, 77%) was obtained from the compound 4.3b by following the general protocol D2.

Tm=151° C.; $^1$H NMR (400 MHz, MeOD) δ ppm 0.90 (t, J=6.7 Hz, 3H), 1.20-1.41 (m, 16H), 1.55-1.68 (m, 2H), 1.90-2.02 (m, 1H), 2.14-2.24 (m, 1H), 2.25 (t, J=7.5 Hz, 2H), 2.36-2.42 (m, 2H), 2.66 (dd, J=16.7, 7.2 Hz, 1H), 2.85 (dd, J=16.7, 6.5 Hz, 1H), 4.43 (dd, J=8.7, 4.8 Hz, 1H), 4.79 (dd, J=7.2, 6.5 Hz, 1H); $^{13}$C NMR (100 MHz, MeOD) δ ppm 14.4 (CH$_3$), 23.7 (CH$_2$), 26.8 (CH$_2$), 27.9 (CH$_2$), 30.2-31.1 (6×CH$_2$), 33.06 (CH$_2$), 36.7 (CH$_2$), 36.9 (CH$_2$), 51.1 (CH), 53.2 (CH), 173.0 (C), 173.8 (C), 174.5 (C), 176.5 (2×C); Mass (ESI−) m/z (%) 425 [M-F]$^-$, 443 (100) [M−H]$^-$, 465 [M+Na-2H]$^-$; HRMS (ESI−) m/z calculated for C$_{21}$H$_{35}$N$_2$O$_8$ 443.2393 [M−H]$^-$, found 443.2396.

Compound 4.5c

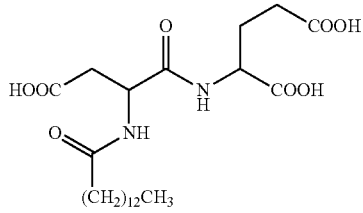

The compound 4.5c (white solid, 194 mg, 0.41 mmol, 76%) was obtained from the compound 4.3c by following the general protocol D2.

Tm=145-148° C.; $^1$H NMR (400 MHz, MeOD) δ ppm 0.90 (t, J=6.8 Hz, 3H), 1.20-1.40 (m, 20H), 1.56-1.67 (m, 2H), 1.91-2.02 (m, 1H), 2.14-2.24 (m, 1H), 2.25 (t, J=7.5 Hz, 2H), 2.36-2.43 (m, 2H), 2.66 (dd, J=16.7, 7.2 Hz, 1H), 2.85 (dd, J=16.7, 6.4 Hz, 1H), 4.43 (dd, J=8.8, 4.8 Hz, 1H), 4.79 (dd, J=7.2, 6.4 Hz, 1H); $^{13}$C NMR (100 MHz, MeOD) δ ppm 14.4 (CH$_3$), 23.7 (CH$_2$), 26.8 (CH$_2$), 27.9 (CH$_2$), 30.2-31.1 (10×CH$_2$), 33.1 (CH$_2$), 36.7 (CH$_2$), 36.9 (CH$_2$), 51.1 (CH), 53.2 (CH), 173.0 (C), 173.8 (C), 174.5 (C), 176.5 (2×C); Mass (ESI-) m/z (%) 453 [M-F]$^-$, 471 (100) [M-H]$^-$, 493 [M+Na-2H]$^-$; HRMS (ESI-) m/z calculated for C$_{23}$H$_{39}$N$_2$O$_8$ 471.2706 [M-H]$^-$, found 471.2686.

Compound 4.5d

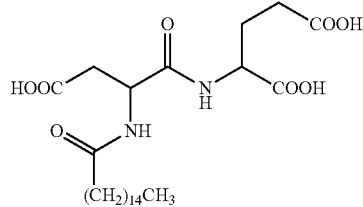

The compound 4.5d (white solid, 243 mg, 0.49 mmol, 93%) was obtained from the compound 4.3d by following the general protocol D2.

Tm=138-141° C.; $^1$H NMR (400 MHz, MeOD) δ ppm 0.90 (t, J=6.9 Hz, 3H), 1.23-1.38 (m, 24H), 1.56-1.67 (m, 2H), 1.91-2.02 (m, 1H), 2.15-2.24 (m, 1H), 2.25 (t, J=7.5 Hz, 2H), 2.36-2.43 (m, 2H), 2.66 (dd, J=16.6, 7.2 Hz, 1H), 2.86 (dd, J=16.6, 6.3, 1H), 4.43 (dd, J=8.8, 4.8, Hz, 1H), 4.79 (dd, J=7.2, 6.3 Hz, 1H); $^{13}$C NMR (100 MHz, MeOD) δ ppm 14.4 (CH$_3$), 23.7 (CH$_2$), 26.8 (CH$_2$), 27.9 (CH$_2$), 30.2-31.1 (12×CH$_2$), 33.1 (CH$_2$), 36.7 (CH$_2$), 36.9 (CH$_2$), 51.1 (CH), 53.2 (CH), 173.0 (C), 173.9 (C), 174.5 (C), 176.5 (2×C); Mass (ESI-) m/z (%) 481 [M-F]$^-$, 499 (100) [M-H]$^-$, 521 [M+Na-2H], HRMS (ESI-) m/z calculated for C$_{25}$H$_{43}$N$_2$O$_8$ 499.3019 [M-H]$^-$, found 499.3027.

Compound 4.6a

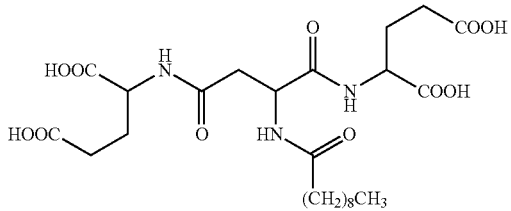

The compound 4.6a (white solid, 221 mg, 0.40 mmol, 93%) was obtained from the compound 4.4a by following the general protocol D2.

Tm=170-175° C.; $^1$H NMR (400 MHz, MeOD) δ ppm 0.90 (t, J=6.8 Hz, 3H), 1.21-1.37 (m, 12H), 1.54-1.66 (m, 2H), 1.87-2.02 (m, 2H), 2.13-2.28 (m, 4H), 2.35-2.44 (m, 4H), 2.63 (dd, J=15.1, 8.0 Hz, 1H), 2.80 (dd, J=15.1, 6.1 Hz, 1H), 4.40-4.48 (m, 2H), 4.80 (dd, J=8.0 6.1 1H); $^{13}$C NMR (100 MHz, MeOD) δ ppm 14.4 (CH$_3$), 23.7 (CH$_2$), 26.8 (CH$_2$), 27.9 (CH$_2$), 28.0 (CH$_2$), 30.4 (2×CH$_2$), 30.5 (CH$_2$), 30.6 (CH$_2$), 31.1 (CH$_2$), 31.2 (CH$_2$), 33.0 (CH$_2$), 36.9 (CH$_2$), 38.4 (CH$_2$), 51.6 (CH), 53.0 (CH), 53.2 (CH), 172.1 (C), 173.1 (C), 174.6 (C), 175.0 (C), 176.4 (C), 176.5 (2×C); Mass (ESI-) m/z (%) 544 (100) [M-H]$^-$, 566 [M+Na-2H]$^-$; HRMS (ESI-) m/z calculated for C$_{24}$H$_{38}$N$_3$O$_{11}$ 544.2506 [M-H]$^-$, found 544.2514.

Compound 4.6b

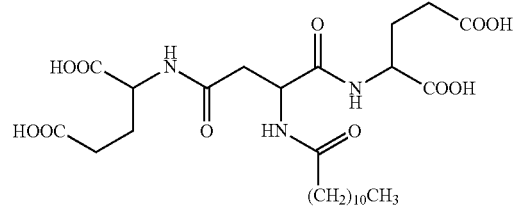

The compound 4.6b (white solid, 247 mg, 0.43 mmol, 98%) was obtained from the compound 4.4b by following the general protocol D2.

Tm=165-170° C.; $^1$H NMR (400 MHz, MeOD) δ ppm 0.90 (t, J=6.8 Hz, 3H) 1.20-1.38 (m, 16H), 1.54-1.66 (m, 2H), 1.88-2.02 (m, 2H), 2.13-2.28 (m, 4H), 2.35-2.44 (m, 4H), 2.63 (dd, J=15.1 8.1 Hz, 1H), 2.80 (dd, J=15.1, 6.1 Hz, 1H), 4.39-4.48 (m, 2H), 4.79 (dd, J=8.1, 6.1 1H); $^{13}$C NMR (100 MHz, MeOD) δ ppm 14.4 (CH$_3$), 23.7 (CH$_2$), 26.8 (CH$_2$), 28.0 (CH$_2$), 28.1 (CH$_2$), 30.3-31.3 (8×CH$_2$), 33.1 (CH$_2$), 36.9 (CH$_2$), 38.4 (CH$_2$), 51.7 (CH), 53.2 (CH), 53.3 (CH), 172.1 (C), 173.1 (C), 174.7 (C), 175.2 (C), 176.5 (C), 176.6 (C); Mass (ESI-) m/z (%) 572 [M-H]$^-$, 594 (100) [M+Na-2H]; HRMS (ESI-) m/z calculated for C$_{26}$H$_{42}$N$_3$O$_{11}$ 572.2819 [M-H]$^-$, found 572.2817.

Compound 4.6c

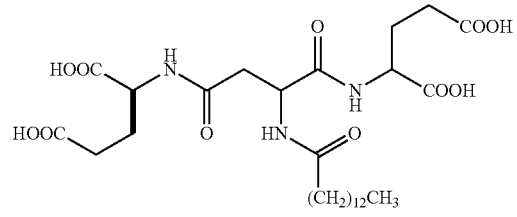

The compound 4.6c (white solid, 208 mg, 0.35 mmol, 80%) was obtained from the compound 4.4c by following the general protocol D2.

Tm=155-160° C.; $^1$H NMR (400 MHz, MeOD) δ ppm 0.90 (t, J=6.8 Hz, 3H), 1.22-1.38 (m, 20H), 1.54-1.67 (m, 2H), 1.87-2.02 (m, 2H), 2.13-2.29 (m, 4H), 2.36-2.44 (m, 4H), 2.63 (dd, J=15.0, 8.0 Hz, 1H), 2.81 (dd, J=15.0, 6.1 Hz, 1H), 4.40-4.48 (m, 2H), 4.77-4.83 (dd, J=8.0, 6.1, 1H); $^{13}$C NMR (100 MHz, MeOD) δ ppm 14.4 (CH$_3$), 23.7 (CH$_2$), 26.8 (CH$_2$), 27.9 (CH$_2$), 28.0 (CH$_2$), 31.3-30.3 (10×CH$_2$), 33.1 (CH$_2$), 36.9 (CH$_2$), 38.4 (CH$_2$), 51.6 (CH), 53.0 (CH), 53.2 (CH), 172.1 (C), 173.1 (C), 174.6 (C), 175.0 (C), 176.4 (C), 176.5 (2×C); Mass (ESI-) m/z (%) 600 (100) [M-H]$^-$, 622 [M+Na-2H]; HRMS (ESI-) m/z calculated for C$_{28}$H$_{46}$N$_3$O$_{11}$ 600.3132 [M-H]$^-$; found 600.3108.

Compound 4.6d

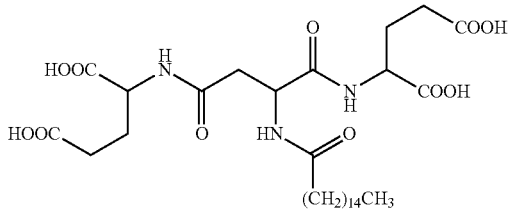

The compound 4.6d (white solid, 208 mg, 0.33 mmol, 75%) was obtained from the compound 4.4d by following the general protocol D2.

Tm=158-160° C.; $^1$H NMR (400 MHz, MeOD) δ ppm 0.90 (t, J=6.8 Hz, 3H), 1.22-1.37 (m, 24H), 1.54-1.66 (m, 2H), 1.85-2.02 (m, 2H), 2.13-2.28 (m, 4H), 2.35-2.44 (m, 4H), 2.63 (dd, J=15.1, 8.0 Hz, 1H), 2.80 (dd, J=15.1, 6.1 Hz, 1H), 4.42-4.48 (m, 2H), 4.79 (dd, J=8.0, 6.1 1H); $^{13}$C NMR (100 MHz, MeOD) δ ppm 14.4 (CH$_3$), 23.7 (CH$_2$), 26.8 (CH$_2$), 27.9 (CH$_2$), 28.0 (CH$_2$), 30.3-31.3 (12×CH$_2$), 33.1 (CH$_2$), 36.9 (CH$_2$), 38.4 (CH$_2$), 51.7 (CH), 53.1 (CH), 53.2 (CH), 172.1 (C), 173.1 (C), 174.6 (C), 175.0 (C), 176.4 (C), 176.5 (2×C); Mass (ESI−) m/z (%) 628 (100) [M−H]$^-$, 650 [M+Na−2H]$^-$; HRMS (ESI−) m/z calculated for C$_{30}$H$_{50}$N$_3$O$_{11}$ 628.3445 [M−H]$^-$; found 628.3448.

Example 6: Compounds 5.1 to 5.3

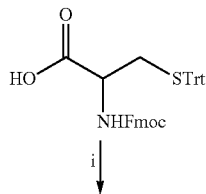

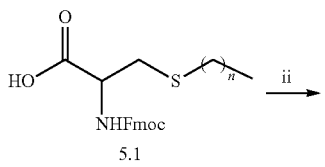
5.1

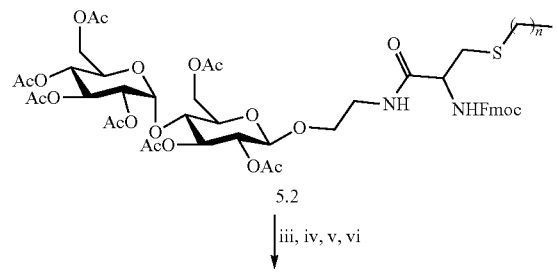
5.2

↓ iii, iv, v, vi

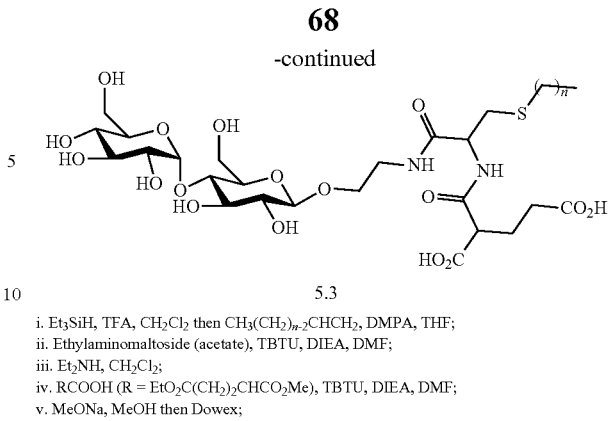
5.3 i. Et$_3$SiH, TFA, CH$_2$Cl$_2$ then CH$_3$(CH$_2$)$_{n-2}$CHCH$_2$, DMPA, THF;
ii. Ethylaminomaltoside (acetate), TBTU, DIEA, DMF;
iii. Et$_2$NH, CH$_2$Cl$_2$;
iv. RCOOH (R = EtO$_2$C(CH$_2$)$_2$CHCO$_2$Me), TBTU, DIEA, DMF;
v. MeONa, MeOH then Dowex;
vi. LiOH, THF/H$_2$O.

Compound 5.1a

The compound 5.1a (white solid, 1.051 g, 2.06 mmol, 60%) was obtained from L-Fmoc-Cys(Trt)-OH and dodecene by following the general protocol L.

Rf=0.16 (CH$_2$Cl$_2$/MeOH/AcOH 99:0.5:0.5); Tm=66-68° C.; $^1$H NMR (400 MHz, CDCl$_3$) δ ppm 0.88 (t, J=6.8 Hz, 3H), 1.17-1.40 (m, 18H), 1.57 (m, 2H), 2.56 (t, J=7.0 Hz, 2H), 3.03 (d, J=4.7 Hz, 2H), 4.24 (t, J=7.0 Hz, 1H), 4.41 (d, J=6.9 Hz, 2H), 4.63 (m, 1H), 5.65 (d, J=7.8 Hz, NHFmoc), 7.32 (m, 2H), 7.40 (t, J=7.5 Hz, 2H), 7.60 (d, J=6.6 Hz, 2H), 7.76 (d, J=7.5 Hz, 2H); $^{13}$C NMR (100 MHz, CDCl$_3$) δ ppm 14.3 (CH$_3$), 22.8 (CH$_2$), 28.8-32.1 (9×CH$_2$), 33.1 (CH$_2$), 34.2 (CH$_2$), 47.2 (CH), 53.6 (CH), 67.6 (CH$_2$), 120.2 (2×CH), 125.3 (2×CH), 127.3 (2×CH), 127.9 (2×CH), 141.5 (2×C). 143.8 (C), 143.9 (C), 156.1 (C), 175.0 (C); Mass (ESI+) m/z (%) 512 (100) [M+H]$^+$; HRMS (ESI+) m/z calculated for C$_{30}$H$_{42}$NO$_4$S 512.2829, found 512.2823.

Compound 5.1b

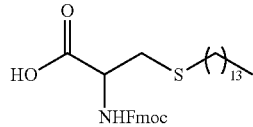

The compound 5.1b (white solid, 1.050 g, 1.95 mmol, 57%) was obtained from L-Fmoc-Cys(Trt)-OH and tetradecene by following the general protocol L.

Rf=0.16 (CH$_2$Cl$_2$/MeOH/AcOH 99:0.5:0.5); Tm=71-72° C.; $^1$H NMR (400 MHz, CDCl$_3$) δ ppm 0.88 (t, J=6.8 Hz, 3H), 1.17-1.40 (m, 22H), 1.57 (m, 2H), 2.55 (t, J=7.0 Hz, 2H), 3.03 (d, J=4.3 Hz, 2H), 4.24 (t, J=7.0 Hz, 1H), 4.41 (d, J=6.8 Hz, 2H), 4.63 (m, 1H), 5.65 (d, J=7.8 Hz, NHFmoc), 7.31 (m, 2H), 7.40 (t, J=7.4 Hz, 2H), 7.60 (d, J=6.7 Hz, 2H), 7.76 (d, J=7.5 Hz, 2H); $^{13}$C NMR (100 MHz, CDCl$_3$) δ ppm 14.2 (CH$_3$), 22.8 (CH$_2$), 28.8-32.1 (11×CH$_2$), 33.1 (CH$_2$), 34.3 (CH$_2$), 47.2 (CH), 53.6 (CH), 67.6 (CH$_2$), 120.1 (2×CH), 125.2 (2×CH), 127.2 (2×CH), 127.9 (2×CH), 141.4 (2×C), 143.8 (C), 143.9 (C), 156.1 (C), 175.5 (C); Mass (ESI−) m/z (%) 316 (100), 538 (40) [M+H]$^-$; HRMS (ESI−) m/z calculated for C$_{32}$H$_{44}$NO$_4$S 538.2991 [M−H]$^-$, found 538.2970.

Compound 5.1c

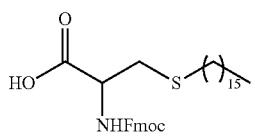

The compound 5.1c (white solid, 1.248 g, 2.20 mmol, 64%) was obtained from L-Fmoc-Cys(Trt)-OH and hexadecene by following the general protocol L.

Rf=0.16 (CH$_2$Cl$_2$/MeOH/AcOH 99:0.5:0.5); Tm=70° C.; $^1$H NMR (400 MHz, CDCl$_3$) δ ppm 0.88 (t, J=6.8 Hz, 3H), 1.14-1.40 (m, 26H), 1.57 (m, 2H), 2.56 (t, J=7.0 Hz, 2H), 3.03 (d, J=4.5 Hz, 2H), 4.24 (t, J=7.0 Hz, 1H), 4.41 (d, J=6.6 Hz, 2H), 4.62 (m, 1H), 5.65 (d, J=7.7 Hz, NHFmoc), 7.31 (m, 2H,), 7.40 (t, J=7.4 Hz, 2H), 7.60 (d, J=6.8 Hz, 2H), 7.76 (d, J=7.5 Hz, 2H); $^{13}$C NMR (100 MHz, CDCl$_3$) δ ppm 14.3 (CH$_3$), 22.8 (CH$_2$), 28.8-32.1 (13×CH$_2$), 33.1 (CH$_2$), 34.2 (CH$_2$), 47.3 (CH), 53.6 (CH), 67.6 (CH$_2$), 120.2 (2×CH), 125.3 (2×CH), 127.3 (2×CH), 127.9 (2×CH), 141.5 (2×C), 143.8 (C), 143.9 (C), 156.1 (C), 174.9 (C); Mass (ESI+) m/z (%) 568 (100) [M+H]$^+$; HRMS (ESI+) m/z calculated for C$_{34}$H$_{50}$NO$_4$S 568.3455 [M+H]$^+$, found 568.3451.

Compound 5.1d

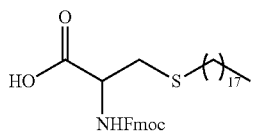

The compound 5.1d (white solid, 1.230 g. 2.07 mmol, 60%) was obtained from L-Fmoc-Cys(Trt)-OH and octadecene by following the general protocol L.

Rf=0.16 (CH$_2$Cl$_2$/MeOH/AcOH 99:0.5:0.5); Tm=74° C.; $^1$H NMR (400 MHz, CDCl$_3$) δ ppm 0.88 (t, J=6.8 Hz, 3H), 1.13-1.40 (m, 30H), 1.57 (m, 2H), 2.56 (t, J=6.7 Hz, 2H), 3.03 (d, J=4.4 Hz, 2H), 4.24 (t, J=7.0 Hz, 1H), 4.42 (d, J=6.7 Hz, 2H), 4.62 (d, J=6.0 Hz, 1H), 5.64 (d, J=7.6 Hz, NHFmoc), 7.32 (m, 2H), 7.40 (t, J=7.5 Hz, 2H), 7.60 (d, J=7.2 Hz, 2H), 7.77 (d, J=7.5 Hz, 2H); $^{13}$C NMR (100 MHz, CDCl$_3$) δ ppm 14.3 (CH$_3$), 22.8 (CH$_2$), 28.9-32.1 (15×CH$_2$), 33.1 (CH$_2$), 34.2 (CH$_2$), 47.2 (CH), 53.6 (CH), 67.6 (CH$_2$), 120.2 (2×CH), 125.3 (2×CH), 127.3 (2×CH), 127.9 (2×CH), 141.5 (2×C), 143.8 (C), 143.9 (C), 156.1 (C), 174.8 (C); Mass (ESI+) m/z (%) 596 (100) [M+H]$^+$; HRMS (ESI+) m/z calculated for C$_{36}$H$_{54}$NO$_4$S 596.3768 [M+H]$^+$, found 596.3762.

Compound 5.2a

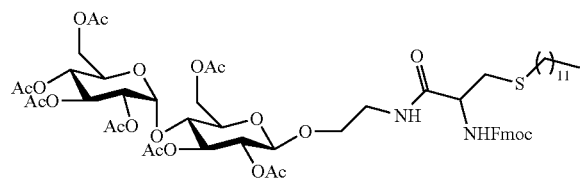

The compound 5.2a (colorless solid, 1.036 g, 0.87 mmol, 60%) was obtained from the compound 5.1a and 2'-aminoethyl-4-O-(2,3,4,6-tetra-O-acetyl-α-D-glucopyranosyl)-2,3, 6-tri-O-acetyl-β-D-glucopyranoside (not described) by following the general protocol A.

Rf=0.29 (Cyclohexane/EtOAc 5:5); Tm=84-85° C.; $^1$H NMR (400 MHz, CDCl$_3$) δ ppm 0.86 (t, J=7.0 Hz, 3H), 1.16-1.38 (m, 18H), 1.50-1.62 (m, 2H), 1.99, 1.99, 2.01, 2.01, 2.03, 2.08, 2.11 (s, 21H), 2.45-2.60 (m, 2H), 2.76-2.96 (m, 2H), 3.32-3.44 (m, 1H), 3.46-3.56 (m, 1H), 3.61-3.71 (m, 2H), 3.75-3.84 (m, 1H), 3.90-3.98 (m, 2H), 4.03 (dd, J=12.4, 2.2 Hz, 1H), 4.15 (dd, J=12.2, 4.4 Hz, 1H), 4.18-4.28 (m, 3H), 4.34-4.47 (m, 2H), 4.51 (d, J=7.8 Hz, 1H), 4.52 (dd, J=12.2, 2.5 Hz, 1H), 4.79 (dd, J=9.3, 7.8 Hz, 1H), 4.84 (dd, J=10.4, 4.0 Hz, 1H), 5.05 (t, J=9.7 Hz, 1H), 5.23 (t, J=9.3 Hz, 1H), 5.35 (dd, J=10.4, 9.7 Hz, 1H), 5.39 (d, J=4.0 Hz, 1H), 5.77 (s, NH), 6.66 (s, NH), 7.27-7.33 (m, 2H), 7.41-7.47 (m, 2H), 7.59 (d, J=7.4 Hz, 2H), 7.75 (d, J=7.4 Hz, 2H); $^{13}$C NMR (100 MHz, CDCl$_3$) δ ppm 14.3 (CH$_3$), 20.6-21.1 (7×CH$_3$), 22.8 (CH$_2$), 28.9-32.1 (9×CH$_2$), 32.8 (CH$_2$), 34.8 (CH$_2$), 39.7 (CH$_2$), 47.3 (CH), 54.5 (CH), 61.6 (CH$_2$), 62.7 (CH$_2$), 67.3 (CH$_2$), 68.2 (CH), 68.6 (CH$_2$), 68.7 (CH), 69.5 (CH), 70.2 (CH), 72.3 (CH). 72.6 (2×CH), 75.3 (CH), 95.7 (CH), 100.5 (CH), 120.2 (2×CH), 125.2 (CH), 125.3 (CH), 127.2 (2×CH), 127.9 (2×CH), 141.5 (2×C), 143.9 (2×C), 156.0 (C), 169.6 (C), 170.0 (C), 170.1 (C), 170.3 (C), 170.5 (C), 170.7 (3×C); Mass (ESI+) m/z (%) 1196 (100) [M+Na]$^+$, HRMS (ESI+) m/z calculated for C$_{58}$H$_{81}$N$_2$O$_{21}$S 1195.4872 [M+Na]$^+$, found 1195.4875.

Compound 5.2b

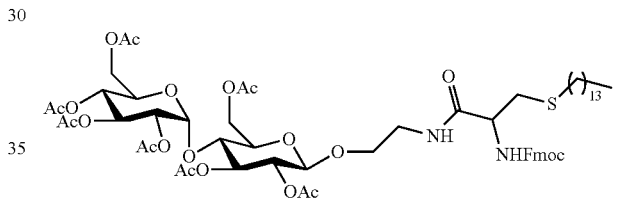

The compound 5.2b (colorless solid, 708 mg, 0.60 mmol, 63%) was obtained from the compound 5.1b and 2'-aminoethyl-4-O-(2,3,4,6-tetra-O-acetyl-α-D-glucopyranosyl)-2,3, 6-tri-O-acetyl-β-D-glucopyranoside (not described) by following the general protocol A.

Rf=0.29 (Cyclohexane/EtOAc 5:5); Tm=90-91° C.; $^1$H NMR (400 MHz, CDCl$_3$) δ ppm 0.87 (t, J=7.0 Hz, 3H), 1.18-1.39 (m, 22H), 1.52-1.62 (m, 2H), 2.00, 2.00, 2.02, 2.02, 2.04, 2.09, 2.12 (s, 21H), 2.48-2.60 (m, 2H), 2.77-2.97 (m, 2H), 3.31-3.45 (m, 1H), 3.49-3.58 (m, 1H), 3.62-3.73 (m, 2H), 3.77-3.85 (m, 1H), 3.91-3.99 (m, 2H), 4.04 (dd, J=12.4, 2.2 Hz, 1H), 4.16 (dd, J=12.1, 4.4 Hz, 1H), 4.20-4.28 (m, 3H), 4.35-4.48 (m, 2H), 4.53 (d, J=7.8 Hz, 1H), 4.54 (dd, J=12.1, 2.5 Hz, 1H), 4.80 (dd, J=9.3, 7.8 Hz, 1H), 4.85 (dd, J=10.4, 4.0 Hz, 1H), 5.05 (t, J=9.7 Hz, 1H), 5.25 (t, J=9.3 Hz, 1H), 5.35 (dd, J=10.4, 9.7 Hz, 1H), 5.39 (d, J=4.0 Hz, 1H), 5.75 (s, NH), 6.66 (s, NH), 7.28-7.34 (m, 2H), 7.3-7.43 (m, 2H), 7.60 (d, J=7.5 Hz, 2H), 7.77 (d, J=7.5 Hz, 2H); $^{13}$C NMR (100 MHz, CDCl$_3$) δ ppm 14.3 (CH$_3$), 20.6-21.1 (7×CH$_3$), 22.8 (CH$_2$), 28.9-32.1 (11×CH$_2$), 32.8 (CH$_2$), 34.7 (CH$_2$), 39.7 (CH$_2$), 47.3 (CH), 54.5 (CH), 61.6 (CH$_2$), 62.7 (CH$_2$), 67.3 (CH$_2$), 68.1 (CH), 68.6 (CH$_2$), 68.7 (CH), 69.5 (CH), 70.2 (CH), 72.3 (CH), 72.6 (2×CH), 75.3 (CH), 95.7 (CH), 100.5 (CH), 120.2 (2×CH), 125.2 (2×CH), 127.2 (2×CH), 127.9 (2×CH), 141.5 (2×C), 143.9 (2×C), 156.0 (C), 169.6 (C), 170.0 (C), 170.1 (C), 170.3 (C), 170.5 (C), 170.7 (3×C); Mass (ESI+) m/z (%) 1201 (100) [M+H]$^+$; HRMS (ESI+) m/z calculated for C$_{60}$H$_{85}$N$_2$O$_{21}$S 1201.5360 [M+H]$^+$, found 1201.5359.

Compound 5.2c

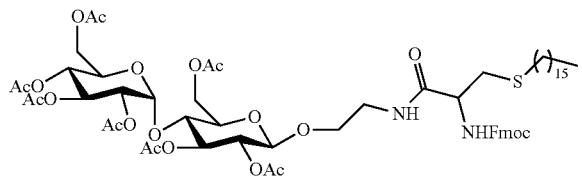

The compound 5.2c (colorless solid, 331 mg. 0.27 mmol, 31%) was obtained from the compound 5.1c and 2'-aminoethyl-4-O-(2,3,4,6-tetra-O-acetyl-α-D-glucopyranosyl)-2,3,6-tri-O-acetyl-β-D-glucopyranoside (not described) by following the general protocol A.

Rf=0.29 (Cyclohexane/EtOAc 5:5); Tm=98-99° C.; $^1$H NMR (400 MHz, CDCl$_3$) δ ppm 0.87 (t, J=6.8 Hz, 3H), 1.16-1.40 (m, 26H), 1.52-1.62 (m, 2H), 2.00, 2.00, 2.02, 2.02, 2.04, 2.09, 2.12 (s, 21H), 2.49-2.59 (m, 2H), 2.77-2.97 (m, 2H), 3.34-3.45 (m, 1H), 3.47-3.58 (m, 1H), 3.62-3.73 (m, 2H), 3.77-3.85 (m, 1H), 3.91-3.99 (m, 2H), 4.04 (dd, J=12.4, 2.2 Hz, 1H), 4.15 (dd, J=12.1, 4.4 Hz, 1H), 4.20-4.28 (m, 3H), 4.35-4.47 (m, 2H), 4.53 (d, J=7.9 Hz, 1H), 4.54 (dd, J=12.1, 2.5 Hz, 1H), 4.80 (dd, J=9.3, 7.9 Hz, 1H), 4.85 (dd, J=10.4, 4.0 Hz, 1H), 5.05 (t, J=9.6 Hz, 1H), 5.24 (t, J=9.3 Hz, 1H), 5.35 (dd, J=10.4, 9.6 Hz, 1H), 5.39 (d, J=4.0 Hz, 1H), 5.75 (s, NH), 6.66 (s, NH), 7.28-7.34 (m, 2H), 7.37-7.43 (m, 2H), 7.60 (d, J=7.4 Hz, 2H), 7.76 (d, J=7.4 Hz, 2H); $^{13}$C NMR (100 MHz, CDCl$_3$) δ ppm 14.3 (CH$_3$), 20.6-21.1 (7×CH$_3$), 22.8 (CH$_2$), 28.9-32.1 (13×CH$_2$), 32.8 (CH$_2$), 34.7 (CH$_2$), 39.6 (CH$_2$), 47.3 (CH), 54.6 (CH), 61.6 (CH$_2$), 62.6 (CH$_2$), 67.3 (CH$_2$), 68.1 (CH), 68.6 (CH$_2$), 68.7 (CH), 69.5 (CH), 70.2 (CH), 72.3 (CH), 72.6 (2×CH), 75.3 (CH), 95.7 (CH), 100.5 (CH), 120.2 (2×CH), 125.2 (2×CH), 127.2 (2×CH), 127.9 (2×CH), 141.5 (2×C), 143.9 (2×C), 156.0 (C), 169.6 (C), 170.0 (C), 170.1 (C), 170.3 (C), 170.5 (C), 170.7 (3×C); Mass (ESI+) m/z (%) 1230 (100) [M+Na]$^+$; HRMS (ESI+) m/z calculated for C$_{62}$H$_{89}$N$_2$O$_{21}$S 1229.5673 [M+H]$^+$, found 1229.5680.

Compound 5.2d

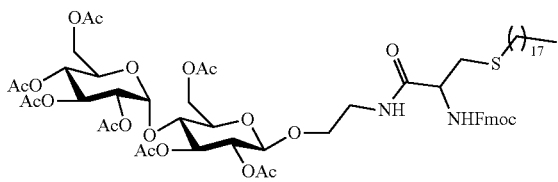

The compound 5.2d (colorless solid, 679 mg, 0.54 mmol, 63%) was obtained from the compound 5.1d and 2'-aminoethyl-4-O-(2,3,4,6-tetra-O-acetyl-α-D-glucopyranosyl)-2,3,6-tri-O-acetyl-β-D-glucopyranoside (not described) by following the general protocol A.

Rf=0.29 (Cyclohexane/EtOAc 5:5); Tm=100° C.; $^1$H NMR (400 MHz, CDCl$_3$) δ ppm 0.88 (t, J=6.8 Hz, 3H), 1.17-1.40 (m, 30H), 1.52-1.63 (m, 2H), 2.00, 2.00, 2.02, 2.02, 2.04, 2.09, 2.13 (s, 21H), 2.48-2.60 (m, 2H), 2.77-2.97 (m, 2H), 3.34-3.46 (m, 1H), 3.47-3.58 (m, 1H), 3.63-3.73 (m, 2H), 3.77-3.85 (m, 1H), 3.91-3.99 (m, 2H), 4.04 (dd, J=12.4, 2.2 Hz, 1H), 4.16 (dd, J=12.2, 4.4 Hz, 1H), 4.20-4.29 (m, 3H), 4.36-4.48 (m, 2H), 4.52 (d, J=7.8 Hz, 1H), 4.54 (dd, J=12.2, 2.6 Hz, 1H), 4.80 (dd, J=9.3, 7.8 Hz, 1H), 4.85 (dd, J=10.5, 4.0 Hz, 1H), 5.06 (t, J=9.7 Hz, 1H), 5.25 (t, J=9.3 Hz, 1H), 5.36 (dd, J=10.5, 9.7 Hz, 1H), 5.39 (d, J=4.0 Hz, 1H), 5.75 (s, NH), 6.64 (s, NH), 7.29-7.34 (m, 2H), 7.40 (m, 2H), 7.60 (d, J=7.5 Hz, 2H), 7.77 (d, J=7.5 Hz, 2H); $^{13}$C NMR (100 MHz, CDCl$_3$) δ ppm 14.3 (CH$_3$), 20.5-21.1 (7×CH$_3$), 22.8 (CH$_2$), 28.9-32.1 (15×CH$_2$), 32.8 (CH$_2$), 34.7 (CH$_2$), 39.6 (CH$_2$), 47.3 (CH), 54.6 (CH), 61.6 (CH$_2$), 62.7 (CH$_2$), 67.3 (CH$_2$), 68.1 (CH), 68.6 (CH$_2$), 68.7 (CH), 69.5 (CH), 70.2 (CH), 72.3 (CH), 72.6 (2×CH), 75.3 (CH), 95.7 (CH), 100.5 (CH), 120.2 (2×CH), 125.2 (2×CH), 127.2 (2×CH), 127.9 (2×CH), 141.5 (2×C), 143.9 (2×C), 156.0 (C), 169.6 (C), 170.0 (C), 170.1 (C), 170.3 (C), 170.5 (C), 170.7 (3×C); Mass (ESI+) m/z (%) 1258 (100) [M+H]$^+$; HRMS (ESI+) m/z calculated for C$_{64}$H$_{93}$N$_2$O$_{21}$S 1257.5986 [M+H]$^+$, found 1257.5984.

Compound 5.3a

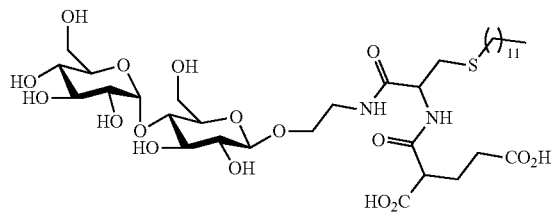

The compound 5.3a (white solid, 50 mg, 0.06 mmol, 35%) was obtained in the form of a mixture of diastereomers from the compound 5.2a and 5-ethoxy-2-(methoxycarbonyl)-5-oxopentanoic acid (not described) by following the general protocols B, then A, J and finally F.

Tm=96-98° C.; $^1$H NMR (400 MHz, CD$_3$OD) δ ppm 0.90 (t, J=6.8 Hz, 3H), 1.21-1.44 (m, 18H), 1.53-1.63 (m, 2H), 1.70-1.82 (m, 1H), 1.84-1.98 (m, 1H), 2.08-2.22 (m, 2H), 2.34-2.43 (m, 2H), 2.52-2.60 (m, 2H), 2.70-2.89 (m, 1H), 2.90-3.07 (m, 1H), 3.22-3.31 (m, 2H), 3.33-3.43 (m, 2H), 3.46 (dd, J=9.8, 3.8 Hz, 1H), 3.48-3.58 (m, 2H), 3.58-3.73 (m, 5H), 3.77-3.95 (m, 4H), 4.29-4.35 (m, 1H), 4.46-4.58 (m, 1H), 5.16 (d, J=3.7 Hz, 1H); $^{13}$C NMR (100 MHz, CD$_3$OD) δ ppm 14.4 (CH$_3$), 23.7 (2×CH$_2$), 24.7-25.6 (CH$_2$), 29.8-30.8 (9×CH$_2$), 32.1-32.3 (CH$_2$), 33.0 (CH$_2$), 33.0-33.2 (CH$_2$), 34.3-34.8 (CH$_2$), 40.6-40.8 (CH$_2$). 52.0-52.5 (CH), 54.4-55.0 (CH), 62.0-62.2 (CH$_2$), 62.7 (CH$_2$), 69.1-69.4 (CH$_2$), 71.4 (CH), 74.1 (CH), 74.6-74.7 (CH), 74.7 (CH), 75.0 (CH), 76.4-76.6 (CH), 77.5-77.7 (CH), 81.0-81.3 (CH), 102.8 (CH), 104.1-104.4 (CH), 171.3-171.6 (C), 172.6-172.8 (C), 172.9-173.2 (C), 176.3-176.5 (C); Mass (ESI-) m/z (%) 384 (25) [M-CO$_2$H]$^{2-}$, 813 (100) [M-H]$^-$, HRMS (ESI-) m/z calculated for C$_{35}$H$_{61}$N$_2$O$_{17}$S 813.3686 [M-H]$^-$, found 813.3651.

Compound 5.3b

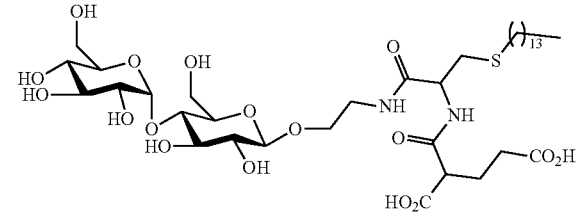

The compound 5.3b (white solid, 52 mg, 0.06 mmol, 26%) was obtained in the form of a mixture of diastereomers from the compound 5.2b and 5-ethoxy-2-(methoxycarbonyl)-5-oxopentanoic acid (not described) by following the general protocols B, then A, J and finally F.

Tm>130° C. (decomposition); $^1$H NMR (400 MHz, CD$_3$OD) δ ppm 0.90 (t, J=6.8 Hz, 3H), 1.21-1.44 (m, 22H), 1.53-1.63 (m, 2H), 1.72-1.83 (m, 1H), 1.82-2.00 (m, 1H), 2.07-2.23 (m, 2H), 2.35-2.45 (m, 2H), 2.52-2.61 (m, 2H), 2.70-2.90 (m, 1H), 2.90-3.07 (m, 1H), 3.22-3.30 (m, 2H), 3.33-3.43 (m, 2H), 3.43-3.48 (m, 1H), 3.48-3.58 (m, 2H), 3.58-3.73 (m, 5H), 3.77-3.95 (m, 4H), 4.29-4.35 (m, 1H), 4.46-4.58 (m, 1H), 5.16 (d, J=3.7 Hz, 1H). $^{13}$C NMR (100 MHz, CD$_3$OD) δ ppm 14.4 (CH$_3$), 23.7 (2×CH$_2$), 24.7-25.6 (CH$_2$), 29.8-30.8 (11×CH$_2$), 32.1-32.3 (CH$_2$), 33.0 (CH$_2$), 33.0-33.2 (CH$_2$), 34.3-34.8 (CH$_2$), 40.6-40.8 (CH$_2$), 52.0-52.5 (CH), 54.4-55.0 (CH), 62.0-62.2 (CH$_2$), 62.7 (CH$_2$), 69.1-69.4 (CH$_2$), 71.5 (CH), 74.1 (CH), 74.6 (CH), 74.7 (CH), 75.0 (CH), 76.4-76.6 (CH), 77.6-77.7 (CH), 81.0-81.1 (CH), 102.9 (CH), 104.2-104.4 (CH), 171.0-171.7 (C), 172.6-172.8 (C), 172.9-173.2 (C), 176.3-176.5 (C); Mass (ESI-) m/z (%) 841 (100) [M−H]$^−$; HRMS (ESI-) m/z calculated for C$_{37}$H$_{65}$N$_2$O$_{17}$S 841.4004 [M−H]$^−$, found 841.4025.

Compound 5.3c

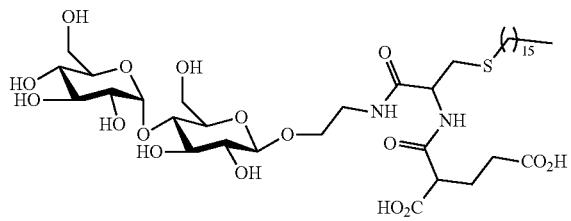

The compound 5.3c (white solid, 82 mg, 0.09 mmol, 41%) was obtained in the form of a mixture of diastereomers from the compound 5.2c and 5-ethoxy-2-(methoxycarbonyl)-5-oxopentanoic acid (not described) by following the general protocols B, then A, J and finally F.

Tm>145° C. (decomposition); $^1$H NMR (400 MHz, CD$_3$OD) δ ppm 0.90 (t, J=6.8 Hz, 3H), 1.21-1.44 (m, 26H), 1.53-1.63 (m, 2H), 1.72-1.82 (m, 1H), 1.82-2.00 (m, 1H), 2.08-2.23 (m, 2H), 2.32-2.45 (m, 2H), 2.52-2.61 (m, 2H), 2.70-2.90 (m, 1H), 2.90-3.07 (m, 1H), 3.22-3.31 (m, 2H), 3.33-3.43 (m, 2H), 3.46 (dd, J=9.7, 3.7 Hz, 1H), 3.48-3.58 (m, 2H), 3.58-3.74 (m, 5H), 3.78-3.95 (m, 4H), 4.30-4.35 (m, 1H), 4.46-4.57 (m, 1H), 5.16 (d, J=3.7 Hz, 1H). $^{13}$C NMR (100 MHz, CD$_3$OD) δ ppm 14.5 (CH$_3$), 23.7 (2×CH$_2$), 24.7-25.6 (CH$_2$), 29.8-30.9 (13×CH$_2$), 32.1-32.3 (CH$_2$), 33.0 (CH$_2$), 33.0-33.2 (CH$_2$), 34.2-34.7 (CH$_2$), 40.6-40.9 (CH$_2$), 52.0-52.5 (CH), 54.3-54.9 (CH), 61.9-62.1 (CH$_2$), 62.7 (CH$_2$), 69.0-69.4 (CH$_2$), 71.4 (CH), 74.1 (CH), 74.6 (CH), 74.7 (CH), 75.0 (CH), 76.4-76.5 (CH), 77.6 (CH), 81.0-81.2 (CH), 102.8 (CH), 104.1-104.3 (CH), 171.0-171.7 (C), 172.6-172.8 (C), 172.9-173.2 (C), 176.3-176.5 (C); Mass (ESI-) m/z (%) 412 (25) [M−CO$_2$H]$^{2−}$, 869 (100) [M−H]$^−$; HRMS (ESI-) m/z calculated for C$_{39}$H$_{69}$N$_2$O$_{17}$S 869.4317 [M−H]$^−$, found 869.4340.

Compound 5.3d

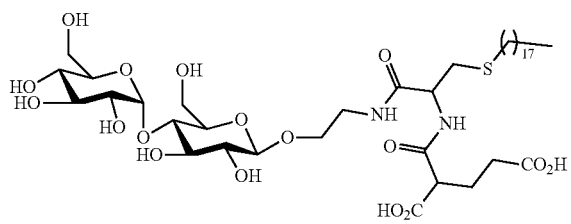

The compound 5.3d (white solid, 81 mg, 0.09 mmol, 30%) was obtained in the form of a mixture of diastereomers from the compound 5.2d and 5-ethoxy-2-(methoxycarbonyl)-5-oxopentanoic acid (not described) by following the general protocols B, then A, J and finally F.

Tm>155° C. (decomposition); $^1$H NMR (400 MHz, CD$_3$OD) δ ppm 0.90 (t, J=6.8 Hz, 3H), 1.21-1.43 (m, 30H), 1.53-1.63 (m, 2H), 1.71-1.82 (m, 1H), 1.86-1.98 (m, 1H), 2.07-2.22 (m, 2H), 2.32-2.43 (m, 2H), 2.52-2.60 (m, 2H), 2.69-2.90 (m, 1H), 2.90-3.07 (m, 1H), 3.22-3.30 (m, 2H), 3.33-3.43 (m, 2H), 3.45 (dd, J=9.7, 3.7 Hz, 1H), 3.48-3.58 (m, 2H), 3.58-3.74 (m, 5H), 3.77-3.95 (m, 4H), 4.29-4.35 (m, 1H), 4.46-4.57 (m, 1H), 5.17 (d, J=3.5 Hz, 1H). $^{13}$C NMR (100 MHz, CD$_3$OD) δ ppm 14.5 (CH$_3$), 23.7 (2×CH$_2$), 24.7-25.6 (CH$_2$), 29.8-30.9 (15×CH$_2$), 32.1-32.3 (CH$_2$), 33.0 (CH$_2$), 33.0-33.2 (CH$_2$), 34.3-34.7 (CH$_2$), 40.6-40.9 (CH$_2$), 52.0-52.5 (CH), 54.4-54.9 (CH), 61.9-62.2 (CH$_2$), 62.7 (CH$_2$), 69.0-69.4 (CH$_2$), 71.5 (CH), 74.1 (CH), 74.6 (CH), 74.7 (CH), 75.0 (CH), 76.4-76.6 (CH), 77.6 (CH), 81.0-81.2 (CH), 102.7-102.9 (CH), 104.1-104.4 (CH), 171.1-171.7 (C), 172.6-172.8 (C), 172.9-173.2 (C), 176.3-176.5 (C); Mass (ESI-) m/z (%) 426 (40) [M−CO$_2$H]$^{2−}$, 898 (100) [M−H]$^−$; HRMS (ESI-) m/z calculated for C$_{41}$H$_{73}$N$_2$O$_{17}$S 897.4630 [M−H]$^−$, found 897.4646.

Example 7: Tests of Absorbance at 280 nm of the Molecules of the Invention

The molecules of the invention were tested and compared using BmrA and AcrB, 2 bacterial polytopic membrane proteins. BmrA is characterized by a functional topology that is sensitive to extraction with detergents. BmrA is a polytopic membrane protein organized into 3 domains: cytosolic, membrane and extracellular (FIG. 1).

The cytosolic domain is formed of 2 parts referred to as nucleotide-binding domains, NBD, which, when they are brought together, bind then hydrolyze ATP. The membrane domain is also formed of 2 parts referred to as transmembrane domains, TMD, each connected to an NBD. The TMDs adopt different conformations oriented towards the inside or the outside of the cell depending on the catalytic cycle. This enables BmrA to capture substrates (S in FIG. 1) present in the intracellular space (or in the plasma membrane) and to evacuate them to the outside. This type of efflux pump is ubiquitous. They belong to the family of ABC transporters which cells overexpress in the event of chemical stress caused by antibiotic, anticancer, antifungal or antiviral treatments. This transport is effected via a conformation change which changes the internal or external orientation of the drug binding sites located in the membrane region of the protein (FIG. 1). After transport, the protein returns to its initial conformation using the energy originating from the hydrolysis of ATP (Ward, A. B. et al. Structures of P-glycoprotein reveal its conformational flexibility and an epitope on the nucleotide-binding domain. Proceedings of the National Academy of Sciences of the United States of America 110, 13386-13391 (2013) ([19]); Martinez, L. et al. Understanding polyspecificity within the substrate-binding cavity of the human multidrug resistance P-glycoprotein. FEBS Journal 281, 673-682 (2014) ([20])). The hydrolysis of ATP is only possible with a functional protein, the topology of which, especially at the membrane region, is native. Extraction by detergents is generally deleterious, for example with dodecyl maltoside (Matar-Merheb, R. et al. ([11])).

Some tests were also performed with the protein AcrB, a prokaryotic trimer of 3×100 kDa embedded in the inner membrane of Gram-bacteria, the 3D structure of which has been resolved (Seeger, M. A. et al. Structural asymmetry of AcrB trimer suggests a peristaltic pump mechanism. Science 313, 1295-1298 (2006) ([21])).

Procedure. The molecules of the invention and also C4C7 (Matar-Merheb, R. et al. ([11])) (provided by CALIXAR) were prepared at the concentrations indicated in FIG. 2 in 50 mM tris-HCl, pH 8.0 and neutralized at this pH. Their absorption spectrum was recorded as indicated using a Xenius SAFAS spectrophotometer.

Results. The concept of the clips is derived from that of aliphatic calix[4]arenes, C4Cn, developed in document WO2009144419 ([28]) and the document by Matar-Merheb, R. et al. ([11]). Despite their benefits, demonstrated in their ability to stabilize membrane proteins, these detergents absorb strongly in the short wavelengths, especially from 220 to 330 nm. This is illustrated with C4 C7 in the 1st panel of FIG. 2. Their molar attenuation coefficient at 280 nm is very high, 15 000 mol/l/cm. Since all the C4Cn detergents were built on the same calix[4]arene support, they all have this characteristic. Thus, they shield the absorption of proteins which are also detected at 280 nm and thus prevent them being monitored or quantified by this means which is very commonly used in biochemistry, especially in a purification protocol.

Figure 2:
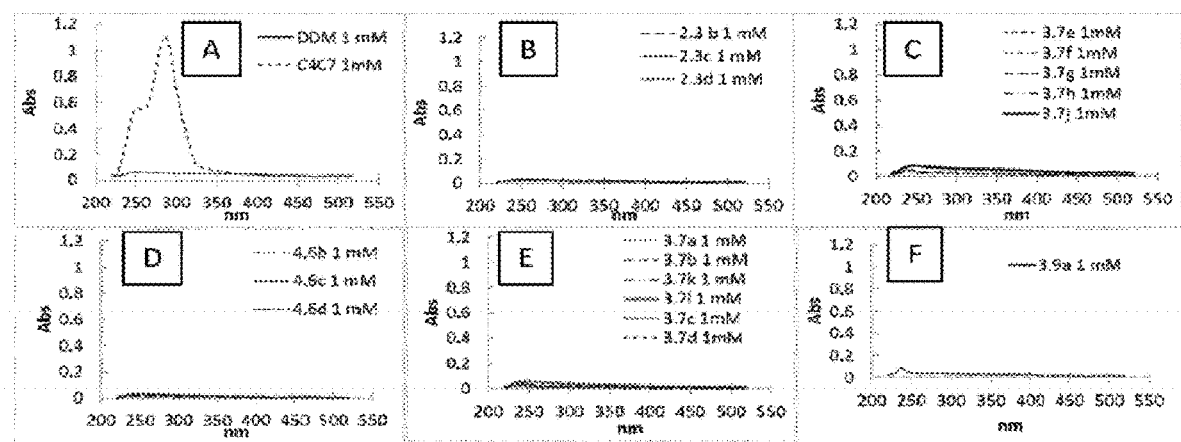
FIG. 2 depicts the absorption spectra of calix[4]arene detergents (exemplified with C4C7) compared to those of the molecules-clips of the invention. The wavelengths are expressed in nm. Panel A: the absorption spectrum of DDM (1 mM) is represented by the continuous line; that of C4C7 (1 mM) is represented by the dashed line. Panel B: the absorption spectrum of the compound 2.3b (1 mM) is represented by ---; that of the compound 2.3c (1 mM) is represented by a continuous line; that of the compound 2.3d (1 mM) is represented by ---. Panel C: the absorption spectrum of the compound 3.7e (1 mM) is represented by ---; that of the compound 3.7f (1 mM) is represented by ---; that of the compound 3.7g (1 mM) is represented by ---; that of the compound 3.7h (1 mM) is represented by ---; that of the compound 3.7j (1 mM) is represented by a continuous line. Panel D: the absorption spectrum of the compound 4.6b (1 mM) is represented by ---; that of the compound 4.6c (1 mM) is represented by a continuous line; that of the compound 4.6d (1 mM) is represented by ---; Panel F: the absorption spectrum of the compound 3.9a (1 mM) is represented by a continuous line. Panel G: the absorption spectrum of the compound 3.7a (1 mM) is represented by ---; that of the compound 3.7b (1 mM) is represented by ---; that of the compound 3.7k (1 mM) is represented by ---; that of the compound 3.7l (1 mM) is represented by a continuous line; that of the compound 3.7c (1 mM) is represented by ---; that of the compound 3.7d (1 mM) is represented by ---.

On the other hand, the molecules of the present invention do not absorb, or only negligibly absorb, from 220 to 500 nm (and beyond), as demonstrated in FIG. 2. Therefore, they do not prevent the detection of proteins at 280 nm.

Example 8: Test of Chelation of Divalent Metals by the Molecules of the Invention The calix[4]arene structure associated with 3 acid functions means that the corresponding detergents chelate divalent metals very effectively. The novel design of the molecules of the invention does away with this effect.

Procedure. The molecules of the invention and also C4C12 (Matar-Merheb, R. et al. ([11])) were prepared at the concentrations indicated in FIG. 3 in 50 mM tris-HCl, pH 8.0 and neutralized at this pH. A concentrated solution of $MgCl_2$ was subsequently added up to 0, 5 and 10 mM. The turbidity of the resulting solution was recorded at 600 nm.

Figure 3:
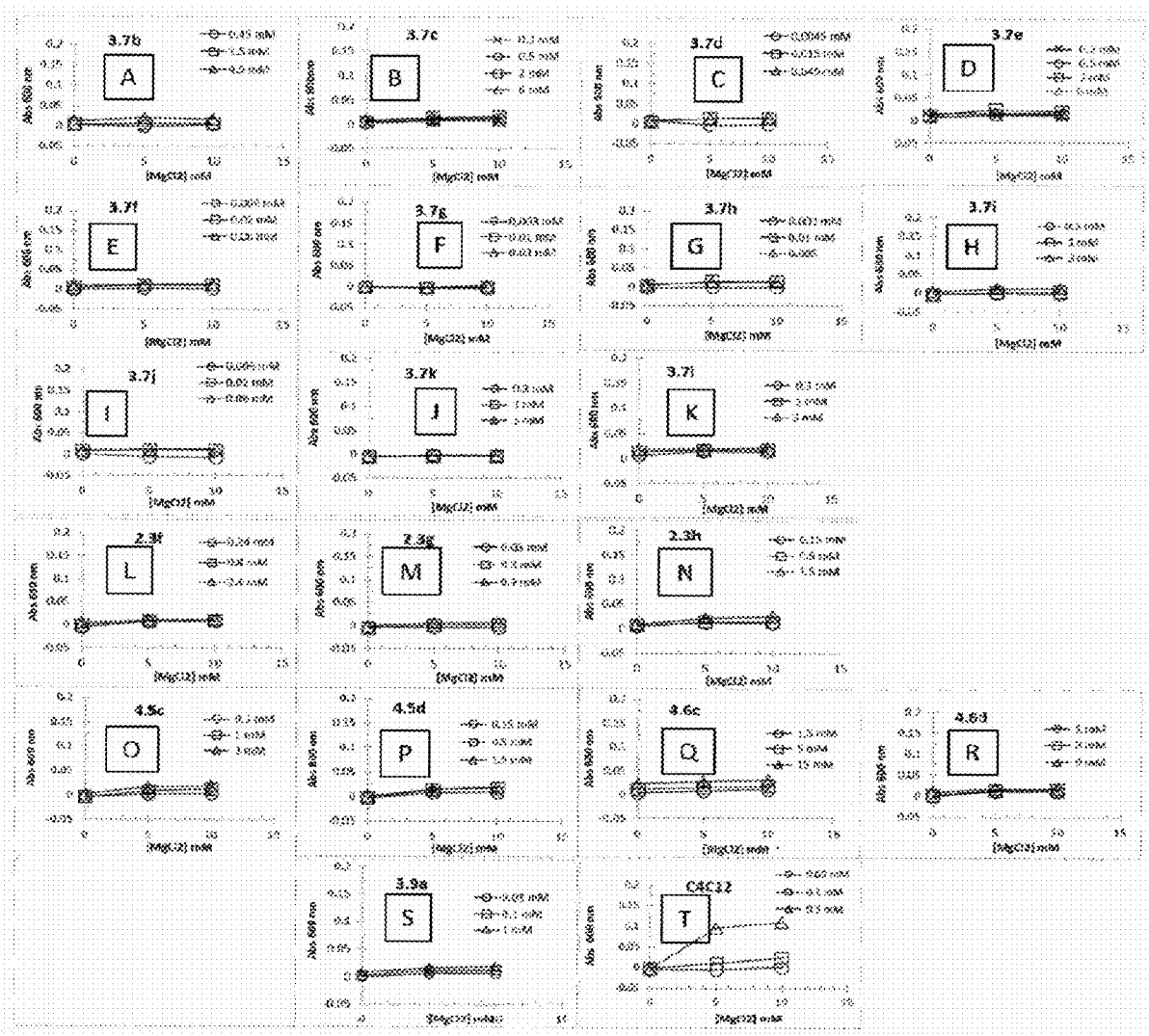
FIG. 3 (A and B) represents the interaction of divalent cations with the molecules of the invention as opposed to the calix[4]arene detergents, here exemplified with C4C12, and shows the absence of interaction of divalent cations with the molecules of the invention as opposed to the calix[4]arene detergents. The absorbance is measured at 600 nm for different concentrations of $MgCl_2$ (mM). Panel A: absorption of the compound 3.7b at the concentrations 0.45 mM (circles), 1.5 mM (squares) and 4.5 mM (triangles). Panel B: absorption of the compound 3.7c at the concentrations 0.2 mM (crosses), 0.5 mM (circles), 2 mM (squares) and 6 mM (triangles). Panel C: absorption of the compound 3.7d at the concentrations 0.0045 mM (circles), 0.0015 mM (squares) and 0.045 mM (triangles). Panel D: absorption of the compound 3.7e at the concentrations 0.2 mM (crosses), 0.5 mM (circles), 2 mM (squares) and 6 mM (triangles). Panel E: absorption of the compound 3.7f at the concentrations 0.006 mM (circles), 0.02 mM (squares) and 0.06 mM (triangles). Panel F: absorption of the compound 3.7g at the concentrations 0.003 mM (circles), 0.01 mM (squares) and 0.03 mM (triangles). Panel G: absorption of the compound 3.7h at the concentrations 0.003 mM (circles), 0.01 mM (squares) and 0.05 mM (triangles). Panel H: absorption of the compound 3.7i at the concentrations 0.3 mM (circles), 1 mM (squares) and 3 mM (triangles). Panel I: absorption of the compound 3.7j at the concentrations 0.006 mM (circles), 0.02 mM (squares) and 0.06 mM (triangles). Panel J: absorption of the compound 3.7k at the concentrations 0.3 mM (circles), 1 mM (squares) and 3 mM (triangles). Panel K: absorption of the compound 3.7l at the concentrations 0.3 mM (circles), 1 mM (squares) and 3 mM (triangles). Panel L: absorption of the compound 2.3f at the concentrations 0.24 mM (circles), 0.8 mM (squares) and 2.4 mM (triangles). Panel M: absorption of the compound 2.3g at the concentrations 0.03 mM (circles), 0.1 mM (squares) and 0.3 mM (triangles). Panel N: absorption of the compound 2.3h at the concentrations 0.15 mM (circles), 0.5 mM (squares) and 1.5 mM (triangles). Panel O: absorption of the compound 4.5c at the concentrations 0.3 mM (circles), 1 mM (squares) and 3 mM (triangles). Panel P: absorption of the compound 4.5d at the concentrations 0.15 mM (circles), 0.5 mM (squares) and 1.5 mM (triangles). Panel Q: absorption of the compound 4.6c at the concentrations 1.5 mM (circles), 5 mM (squares) and 15 mM (triangles). Panel R: absorption of the compound 4.6d at the concentrations 1 mM (circles), 3 mM (squares) and 9 mM (triangles). Panel S: absorption of the compound 3.9a at the concentrations 0.01 mM (circles), 0.1 mM (squares) and 1 mM (triangles). Panel T: absorption of the compound C4C12 at the concentrations 0.03 mM (circles), 0.1 mM (squares) and 0.3 mM (triangles).

Results. The capacity for chelation of divalent cations of the calix[4]arene detergents previously developed is illustrated in FIG. 3 below. It shows that the addition of increasing concentrations of $MgCl_2$ in the presence of C4C12 leads to an increase in the turbidity of the solution, which reflects a precipitation of the C4C12-magnesium complex. The precipitation is complete from 5 mM of $MgCl_2$. This interaction may be a disadvantage for enzymatic reactions which require the presence of metals, calcium, magnesium, for instance the measurement of ATPase activity of ATPases such as BmrA which requires more than 7 mM of $MgCl_2$. The molecules of the present invention, despite the fact that they have from 2 to 4 carboxylic functions, overcome this technical problem. Indeed, as illustrated in FIG. 3, tested under the same conditions as C4C12, they do not form an insoluble complex with magnesium when the latter is added, even up to 10 mM.

This absence of interaction with metals is also very useful during steps of metal affinity-type chromatography, which use nickel or cobalt and which cannot be implemented with high concentrations of C4Cn, unlike the molecules of the invention.

Example 9: Measurement of the Critical Micelle Concentration (CMC) Of the Molecules of the Invention Procedure. The molecules of the invention were prepared in a range of concentrations extending from 0.1 µM to 10 mM in 50 mM tris-HCl, pH 8.0 and neutralized at this pH. To 80 µl of each solution (triplicate), the same volume of 10 µM of 1,6-diphenyl-1,3,5-hexatriene (DPH, Sigma, D208000) is added, prepared at 100 µM in tetrahydrofuran then diluted 10-fold in $H_2O$. The increase in the fluorescence of the DPH occurs when the latter find micelles of clips into which it can insert itself (Chattopadhyay, A. & London, E. Fluorimetric determination of critical micelle concentration avoiding interference from detergent charge. Anal Biochem 139, 408-412 (1984) ([22])). The fluorescence is read with a Xenius SAFAS fluorimeter by exciting at 358 nm and recording the fluorescence emission at 430 nm, with slits of 9 to 10 nm for the excitation and the emission and a gain of 100 to 150, depending on the cases.

Figure 4:
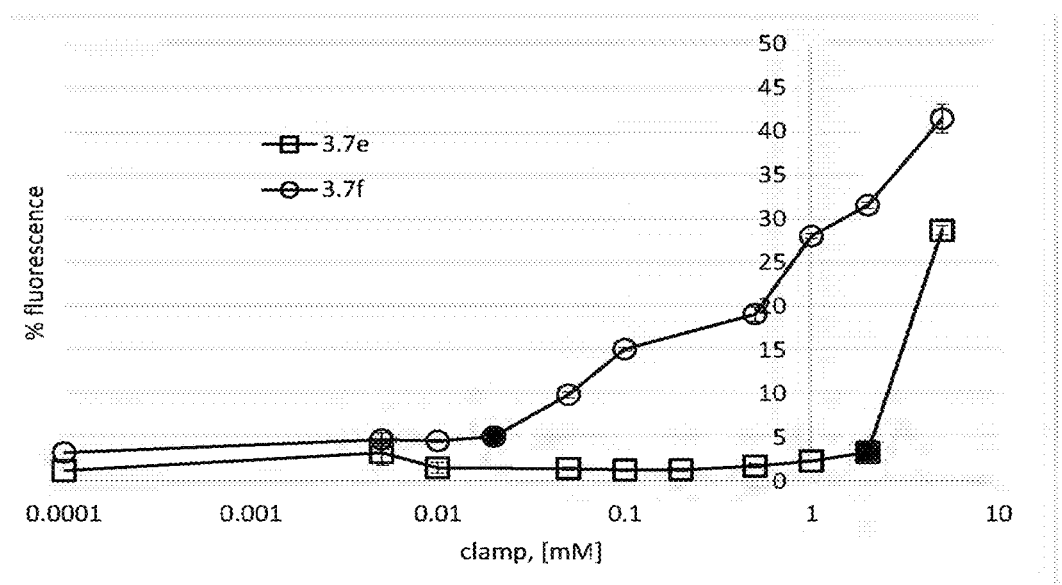
FIG. 4 represents the fluorescence (%) of DPH (1,6-diphenyl-1,3,5-hexatriene) in the presence of increasing concentrations (0.0001 mM, 0.001 mM, 0.01 mM, 0.1 mM, 1 mM and 10 mM) of clips (compounds of the invention), exemplified with the compounds #3.7e (C13, points represented by squares) and 3.7f (C18, points represented by circles). The experiment is carried out in triplicates. In accordance with Chattopadhyay, A. & London, E ([22]), the CMC corresponds to the concentration at which the breakage in the slope is observed, here at 20 µM for 3.7f and 2 mM for 3.7e (black symbols).

Results. The CMC of the detergents is the concentration starting from which they associate with one another to form micelles, in which, in aqueous solution, the hydrophobic portions are grouped together at the center and the hydrophilic regions are exposed to the solvent. This CMC was measured here by following the increase in fluorescence of a compound, DPH, the fluorescence of which increases significantly when it inserts itself into micelles (Chattopadhyay, A. & London, E. ([22])). A typical result obtained with a compound 3.7 provided with a C13 (3.7e) or C18 (3.7h) aliphatic chain is illustrated in FIG. 4. Table 1 below summarizes the values obtained for the molecules of the invention

TABLE 1

| Clip | $(CH_2)_n$ | CMC, mM | Ø, nm |
|---|---|---|---|
| 1.5 | C11 | 2.5 | |
| 2.3a | C13 | 2 | |
| 2.3b | C7 | 5 | — |
| 2.3c | C8 | 3.5 | — |
| 2.3d | C9 | 2 | — |
| 2.3e | C11 | 1 | — |
| 2.3f | C12 | 0.8 | — |
| 2.3g $Na_2$ | C13 | 1 | — |
| 2.3g $K_2$ | C13 | 1 | — |
| 2.3h | C15 | 0.5 | — |
| 3.7a | C9 | 2 | — |
| 3.7b | C11 | 1.5 | — |
| 3.7c | C13 | 1 | 3.8 |
| 3.7d | C18 | 0.02 | 5.5 |
| 3.7e | C13 | 2 | 3.5 |
| 3.7f | C18 | 0.02 | 4.0 |
| 3.7g | C13 | 1 | — |
| 3.7h | C18 | 0.01 | 3-4 |
| 3.7i | C(C5)$_2$ | 1 | — |
| 3.7j | C(C12)$_2$ | 0.02 | 60 |
| 3.7k | C4Hex | 1 | — |
| 3.7l | C13 | 1 | — |
| 3.9a | (C13)$_2$ | 0.01 | 3 |
| 4.5a | C9 | 3 | — |
| 4.5b | C11 | 2 | — |
| 4.5c | C13 | 1.5 | — |
| 4.5d | C15 | 1 | — |
| 4.6a | C9 | 1 | — |
| 4.6b | C11 | 1 | — |
| 4.6c | C13 | 1 | — |
| 4.6d | C15 | 1 | — |

TABLE 1-continued

| Clip | (CH$_2$)$_n$ | CMC, mM | Ø, nm |
|------|--------------|---------|-------|
| 5.3a | C12 | 0.1 | — |
| 5.3b | C14 | 0.05 | — |
| 5.3c | C16 | 0.01 | — |
| 5.3d | C18 | 0.005 | — |

It is observed, conventionally, that the CMC decreases with the length of the aliphatic chain for the compounds 2.3b-g, and 3.7a-d. This applies less for the compounds of series 4, the CMC of which is high and changes little (#4.5-4.6), suggesting that their polar head contributes too much to the hydrophilicity of the assembly. Indeed, these compounds bear 3 to 4 carboxylic functions. Given the large size of the polar heads, these CMCs are relatively high. Thus, the user will be able to vary the length of the chain as a function of the desired goal, for example easy elimination by dialysis or ultrafiltration of a detergent with a high CMC or else retaining the latter by using compounds with a lower CMC.

Example 10: Diameter of the Molecules of the Invention

Another physicochemical parameter of the micelles of detergents is their diameter, assuming that they are spherical. This dimension is obtained by the light scattering (DLS) technique.

Procedure. The molecules of the invention tested were prepared in a range of concentrations extending from 0.1 to 1000×CMC in 30 mM tris-HCl, pH 8.0 and neutralized at this pH. The solutions are filtered on 0.22 µm. The measurement is carried out on 100 µl, in triplicate on a Zetasizer Nano-S from Malvern Instruments.

Figure 5:
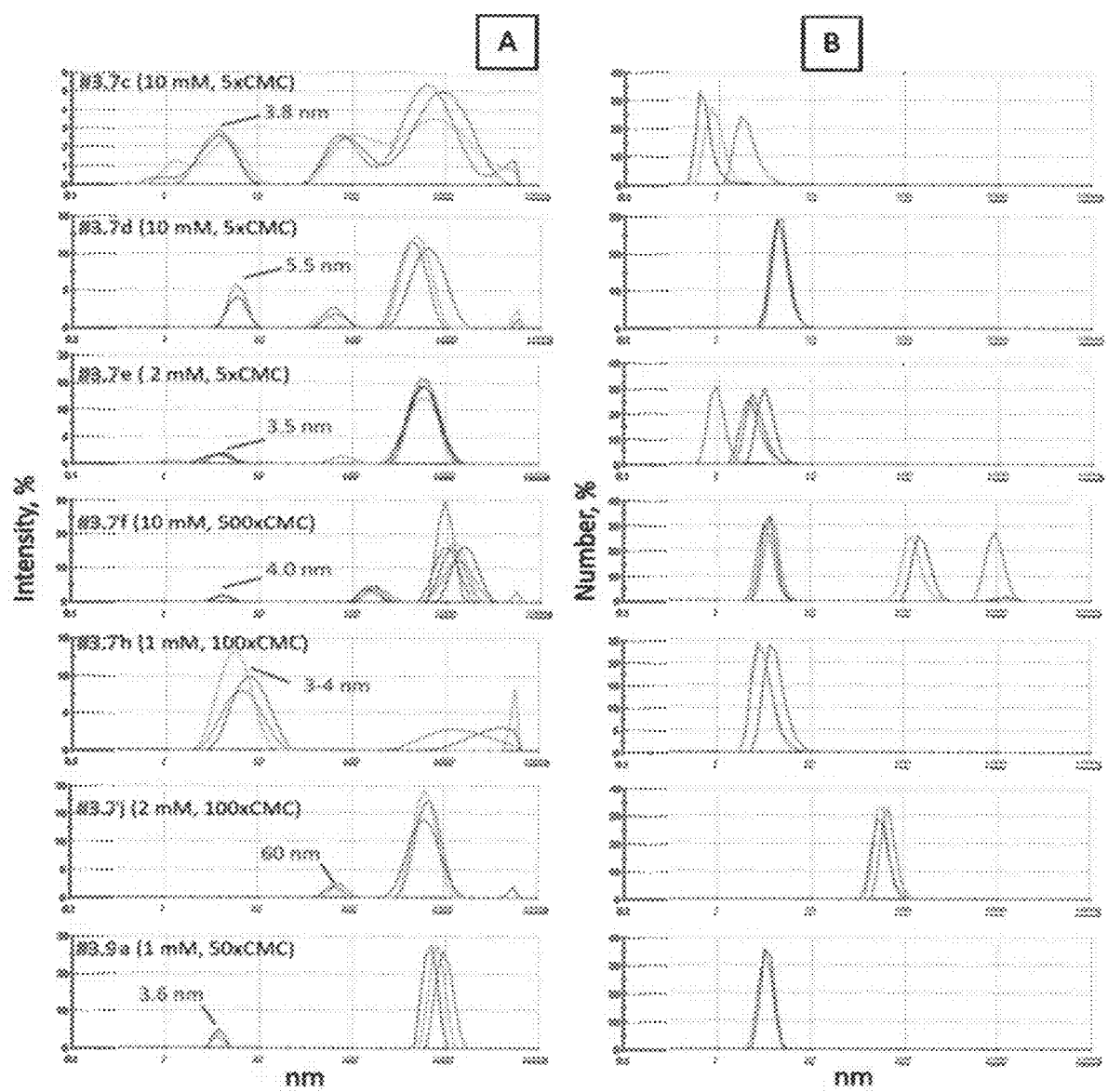
FIG. 5 depicts the dynamic light scattering (DLS) of clips, in intensity (%, column A on the left) and in number (%, column B on the right), as a function of the wavelength (nm). The estimated diameters are indicated on each panel (column A). Columns A and B, from top to bottom: compound 3.7c (10 mM, 5×CMC), compound 3.7d (10 mM, 5×CMC), compound 3.7e (2 mM, 5×CMC), compound 3.7f (10 mM, 500×CMC), compound 3.7h (1 mM, 100×CMC), compound 3.7j (2 mM, 100×CMC), compound 3.9a (1 mM, 50×CMC).

Results. The estimated diameters of the clips tested are, with the exception of the compound 3.7j, of the order of 3 to 5 nm, i.e. relatively small-sized objects for detergents. The micelles therefore are small in size, independent of their CMC, which varies for the compounds tested, from 20 µM to 2 mM. The compound 3.7j is an exception, forming very large objects of the order of 60 nm. It is probable that it behaves like lauryl maltose neopentyl glycols (Chae, P. S. et al. ([6]); Chaptal, V. et al. Quantification of detergents complexed with membrane proteins. Scientific Reports in press (2017) ([23])). Results are illustrated in FIG. 5.

Example 11: Extraction of BmrA and AcrB with the Molecules of the Invention

The extraction capacity of the detergents of the series is tested on membranes in which BmrA or AcrB are strongly expressed. The extraction with the clips (molecules of the invention) is compared to that obtained with commercial detergents, used as reference.

Procedure. BmrA represents 25% of the proteins present in the overexpression system used (E. coli, C41DE3). These membranes are prepared as described previously (Matar-Merheb, R. et al. ([11])). The membranes containing AcrB (approximately 20% of the membrane proteins, same expression system as BmrA) were prepared as described previously (Seeger, M. A. et al. ([21])). The detergents are used at 10 g/l unless indicated otherwise, and the proteins diluted at 2 g/l in a 20 mM Tris-HCl buffer, pH 8.0, 100 mM NaCl, 15% glycerol, with protease inhibitors (Roche) added thereto at an amount of one tablet/100 ml. The mixture (T) is incubated for 2 h at 4° C. then centrifuged for 1 h at 4° C. at 100 000×g in order to separate the extracted fraction (supernatant, S) from that which is not extracted (pellet). The supernatants are deposited on 10% SDS-PAGE and stained with Coomassie blue after migration. The foscholine 12, DDM and LMNG originate from Anatrace, the SDS and Triton X100 originate from Sigma-Aldrich.

Figure 6:
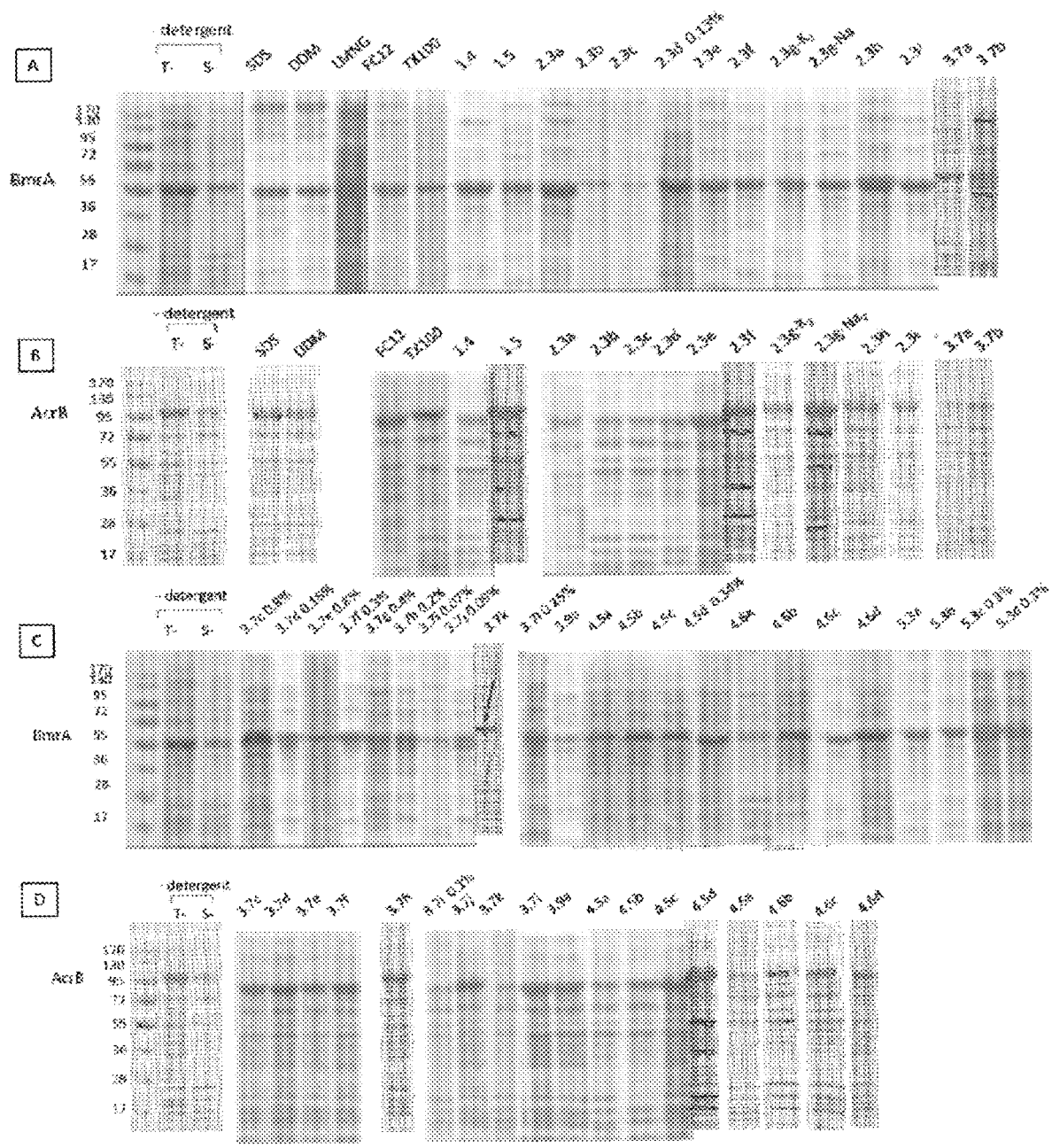
FIG. 6 depicts the extraction of the membrane proteins BmrA (panels A and C) and AcrB (panels B and D) using commercial detergents and the molecules of the invention (panels A and B, from left to right): SDS, DDM, FC12, TX100, compounds of the invention 1.4, 1.5, 2.3a, 2.3b, 2.3c, 2.3d, 2.3e, 2.3f, 2.3g, 2.3h, 2.3i, 3.7a, 3.7b; panel C: compounds of the invention 3.7c 0.8%, 3.7d 0.16%, 3.7e 0.8%, 3.7f 0.3%, 3.7g 0.4%, 3.7h 0.2%, 3.7i 0.07%, 3.7j 0.09%, 3.7k, 3.7l, 0.25%, 3.9a, 4.5a, 4.5b, 4.5c, 4.5d 0.34%, 4.6a, 4.6b, 4.6c, 4.6d, 5.3a, 5.3b, 5.3c 0.3%, 5.3d 0.3%; panel D: 3.7c, 3.7d, 3.7e, 3.7f, 3.7h, 3.7i 0.1%, 3.7j, 3.7k, 3.7l, 3.9a, 4.5a, 4.5b, 4.5c, 4.5d, 4.6a, 4.6b, 4.6c, 4.6d. The detergents are added at 10 g/l (1%), unless indicated otherwise. The equivalent of 20 μg of proteins of the extracted fraction after centrifugation at 100 000×g for 30 min is deposited on 10% SDS-PAGE, stained with Coomassie blue after migration. BmrA migrates in its monomeric form to the level of the 55 kDa band; AcrB migrates in its monomeric form to the level of the 100 kDa band. SDS=sodium dodecyl sulfate; DDM=β-D-dodecyl maltoside; FC12=foscholine-12; TX100=triton X-100.

Results. In the absence of detergent, BmrA and AcrB sediment when they are centrifuged at high speed ("T-" lane vs "S-"); nevertheless, a small fraction resists this treatment and remains in suspension; it corresponds to the negative test ("S-" lane). In the presence of SDS or FC12, the reference detergents used to extract all the membrane proteins, BmrA and AcrB are effectively extracted and are found in the corresponding supernatants, "SDS" or "FC12", used here as extraction positive control. DDM, TX100 and FC12, used here as commercial references, make it possible to solubilize the 2 proteins (FIG. 6). Among the molecules of the invention, some extract the 2 proteins, others partially extract the 2 proteins and finally others do not extract the 2 proteins at all, as summarized in table 2. For BmrA, the extracting compounds are 1.4, 2.3[a, d, f, g, h, i], 3.7[c, f, g, h, l], 4.5[d], 4.6d, 5.3[a-d]. In the group of partially extracting compounds, there are 1.5, 3.7[d, j], 4.5[b, c], and in the group of non-extracting compounds there are 2.3[b, c], 3.7[a, b, e, i, k], 3.9a, 4.5a and 4.6a. For AcrB, the extracting compounds are 1.5, 2.3[a, b, c, d, e, f, g, h, i], 3.7[c, d, e, f, h, j, l], 4.5[b, c, d], 4.6[c, d], those which partially extract are 4.5a, 4.6d, and those which do not extract are 3.7[a, b, i, k] and 4.6a.

TABLE 2

| # | BmrA | AcrB |
|---|------|------|
| 1.4 | +++ | +++ |
| 1.5 | + | +++ |
| 2.3a | +++ | ++ |
| 2.3b | − | ++ |
| 2.3c | − | ++ |
| 2.3d | +++ | ++ |
| 2.3e | +++ | +++ |
| 2.3f | +++ | +++ |
| 2.3g | +++ | +++ |
| 2.3h | +++ | +++ |
| 2.3i | +++ | +++ |
| 3.7a | − | − |
| 3.7b | ++ | − |
| 3.7c | +++ | +++ |
| 3.7d | ++ | +++ |
| 3.7e | + | ++ |
| 3.7f | +++ | +++ |
| 3.7g | +++ | / |
| 3.7h | +++ | +++ |
| 3.7i | − | − |
| 3.7j | ++ | +++ |
| 3.7k | − | − |
| 3.7l | +++ | +++ |
| 3.9a | − | +++ |
| 4.5a | − | + |
| 4.5b | ++ | ++ |
| 4.5c | ++ | +++ |
| 4.5d | +++ | +++ |
| 4.6a | − | − |
| 4.6b | +++ | + |
| 4.6c | +++ | +++ |
| 4.6d | +++ | + |
| 5.3a | +++ | / |
| 5.3b | +++ | / |
| 5.3c | +++ | / |
| 5.3d | +++ | / |

Selective extraction. AcrB is a crystallization contaminant well known in the field of membrane proteins. When co-purified, it crystallizes in trace amounts, leading to numerous artefacts (Psakis, G., Polaczek, J. & Essen, L.-O. AcrB et al.: Obstinate contaminants in a picogram scale. One more bottleneck in the membrane protein structure pipeline. Journal of Structural Biology 166, 107-111 (2009) ([24])). Developing a detergent which limits this contamination by not extracting this protein, or only extracting it very slightly, is therefore highly useful, all the more so since the detergents available on the market are not selective. In this context, the compounds 4.6b and 4.6d are noteworthy for their capacity to not extract, or only very slightly extract, AcrB, unlike BmrA. Conversely, the compounds 1.5 and 3.9a more effectively extract AcrB.

Example 12: Functional Stabilization of the Membrane Proteins after Extraction with Detergents The molecules of the invention which extract BmrA in the previous example were tested at different sub-solubilizing and solubilizing concentrations, to evaluate their impact on the native and functional state of the protein. The latter is monitored by the hydrolysis of ATP which is carried out by the protein during the transport cycle, coupled with translocation of the solute. As reported previously (Matar-Merheb, R. et al. ([11])), the ATPase activity of BmrA is a highly sensitive marker of the state of the protein, the latter being particularly sensitive to the detergents used during the extraction step, where said detergents replace the lipids on contact with the membrane protein.

Figure 7:
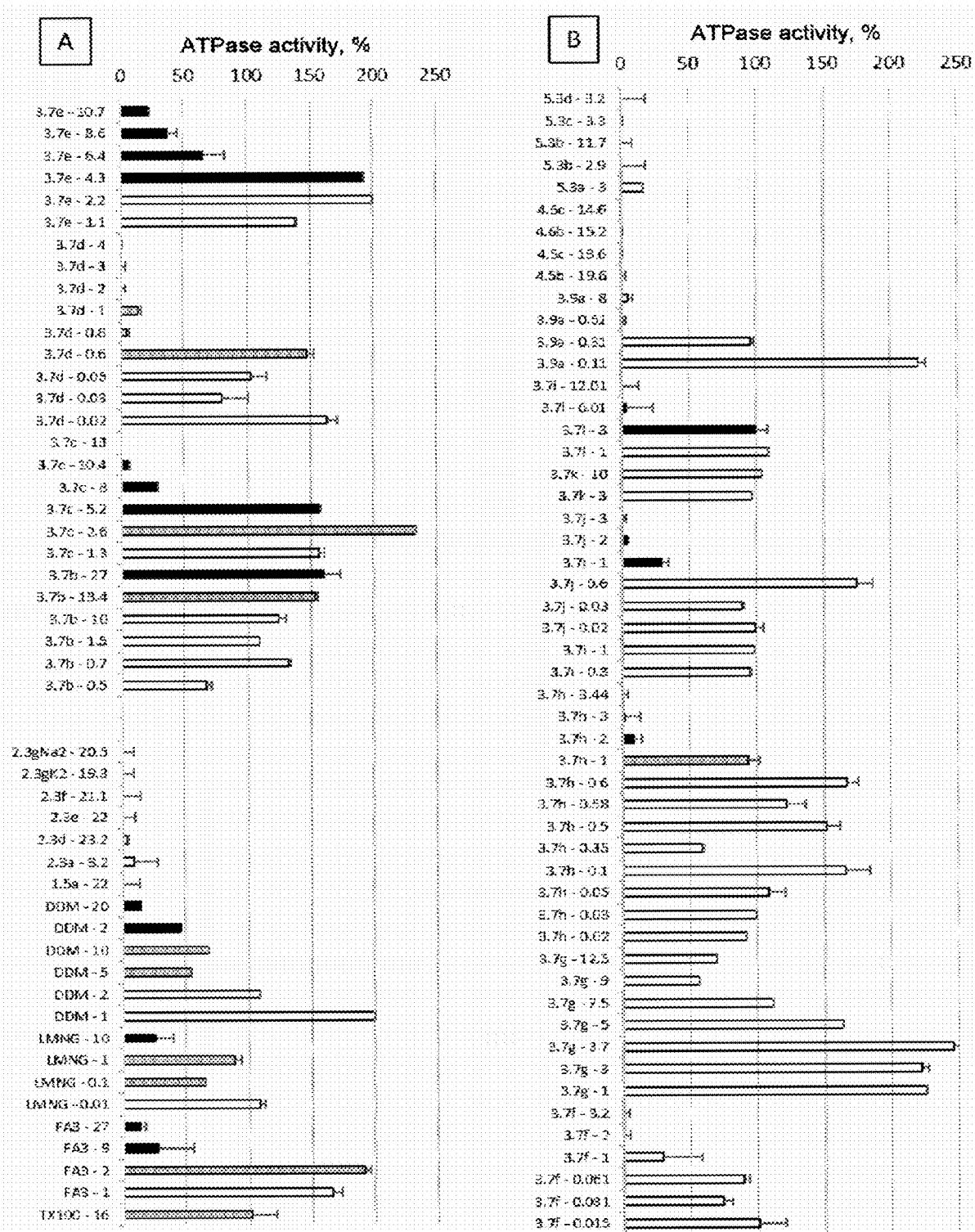
FIG. 7 depicts the effect of the detergents of the invention on the functionality of BmrA (ATPase activity, %). The membrane fraction enriched in BmrA (~25%) diluted to 2 g/l has the compounds added to it at the concentrations (mM) indicated (panel A, from top to bottom: 3.7e 10.7 mM, 3.7e 8.6 mM, 3.7e 6.4 mM, 3.7e 4.3 mM, 3.7e 2.2 mM, 3.7e 1.1 mM, 3.7d 4 mM, 3.7d 3 mM, 3.7d 2 mM, 3.7d 1 mM, 3.7d 0.8 mM, 3.7d 0.6 mM, 3.7d 0.05 mM, 3.7d 0.03 mM, 3.7d 0.02 mM, 3.7c 13 mM, 3.7c 10.4 mM, 3.7c 10 mM, 3.7b 1.5 mM, 3.7b 0.7 mM, 3.7b 0.5 mM, 2.3gNa2 20.5 mM, 2.3gK2 19.3 mM, 2.3f 21.1 mM, 2.3e 22 mM, 2.3d 23.2 mM, 2.3a 3.2 mM, 1.5a 22 mM, DDM 20 mM, DDM 2 mM, DDM 10 mM, DOM 2 mM, DDM 1 mM, LMNG 10 mM, LMNG 1 mM, LMNG 0.1 mM, LMNG 0.01 mM, FA3 27 mM, FA3 9 mM, FA3 2 mM, FA3 1 mM, TX100 16 mM; panel B from top to bottom: compounds of the invention 5.3d 3.2 mM, 5.3c 3.3 mM, 5.3b 11.7 mM, 5.3b 2.9 mM, 5.3a 3 mM, 4.6c 14.6 mM, 4.6b 15.2 mM, 4.5c 18.6 mM, 4.5b 19.6 mM, 3.9a 8 mM, 3.9a 0.51 mM, 3.9a 0.31 mM, 3.9a 0.11 mM, 3.7l 12.01 mM, 3.7l 6.01 mM, 3.7l 3 mM, 3.7l 1 mM, 3.7k 10 mM, 3.7k 3 mM, 3.7j 3 mM, 3.7j 2 mM, 3.7j 1 mM, 3.7j 0.6 mM, 3.7j 0.03 mM, 3.7j 0.02 mM, 3.7j 1 mM, 3.7i 0.3 mM, 3.7h 3 mM, 3.7h 2 mM, 3.7h 1 mM, 3.7h 0.6 mM, 3.7h 0.58 mM, 3.7h 0.5 mM, 3.7h 0.35 mM, 3.7h 0.1 mM, 3.7h 0.5 mM, 3.7h 0.35 mM, 3.7h 0.1 mM, 3.7h 0.05 mM, 3.7h 0.03 mM, 3.7h 0.02 mM, 3.7g 12.5 mM, 3.7g 9 mM, 3.7g 7.5 mM, 3.7g 5 mM, 3.7g 3 mM, 3.7g 1 mM, 3.7f 3.2 mM, 3.7f 2 mM, 3.7f 1 mM, 3.7f 0.061 mM, 3.7f 0.031 mM, 3.7f 0.015 mM). After incubation for 2 h at 4° C., the ATPase activity is measured. The solutions are subsequently centrifuged for 1 h at 4° C., 100 000×g, and the supernatants deposited on 10% SDS-PAGE (cf.
Figure 8:
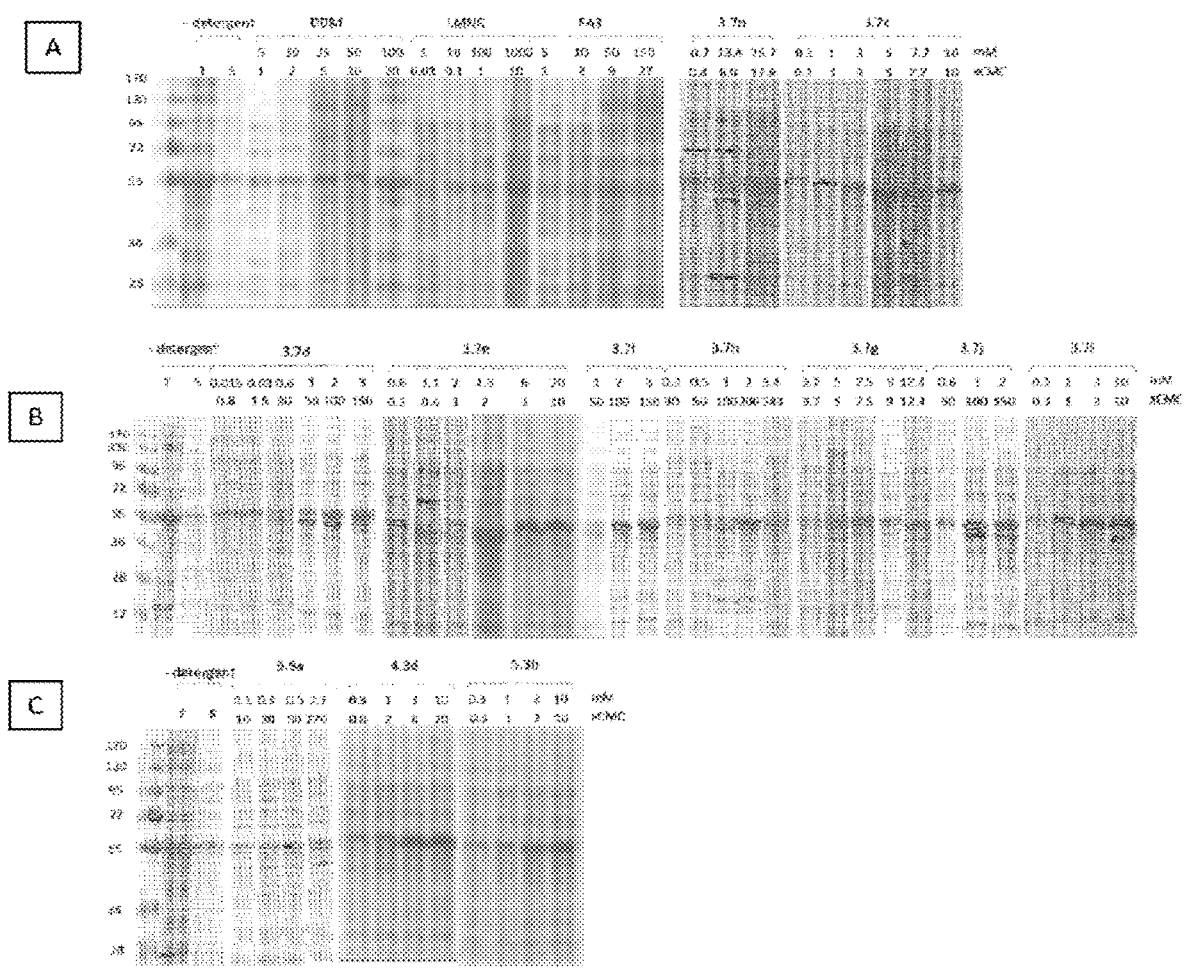
FIG. 8). The gray and black histograms correspond to the concentrations at which BmrA is partially (gray) or entirely (black) extracted, according to these SDS-PAGE. The ATPase activity is in % relative to that of the protein without compound, 0.7 μmol ATP hydrolyzed/min/mg of proteins.

Procedure. BmrA produced and enriched in the plasma membrane of *E. coli* C41 DE3 is prepared as described previously (Matar-Merheb, R. et al. ([11])). The membranes are diluted at 2 g/l in a 20 mM Tris-HCl buffer, pH 8.0, 100 mM NaCl, 15% glycerol, with protease inhibitors (Roche) added thereto at an amount of one tablet/100 ml. The detergents are added at the concentrations indicated in FIG. 7. The mixture (T) is incubated for 2 h at 4° C. and the ATPase activity is measured using the coupled-enzyme system, separating off the vanadate-insensitive activity from the total activity, Centeno, F. et al. Expression of the sarcoplasmic reticulum $Ca^{2+}$-ATPase in yeast. FEBS Lett 354, 117-122 (1994) ([25])). The solutions are subsequently centrifuged for 1 h at 4° C. at 100 000×g in order to separate the extracted fraction (supernatant, S) from that which is not extracted (pellet). The supernatants are deposited on 10% SDS-PAGE and stained with Coomassie blue after migration (FIG. 8). DDM, LMNG (Chae, P. S. et al. ([6])), TritonX100 and FA3 (Lee, S. C. et al. (2013) ([9])) are tested as reference detergents. The DDM and LMNG originate from Anatrace, the Triton X100 originates from Sigma-Aldrich and the FA3 from Avanti-Polars.

Results. As illustrated in FIG. 7, the addition of detergent at a sub-solubilizing or solubilizing concentration induces structural changes in BmrA which impacts on the functionality thereof. Thus, among the reference detergents, LMNG, recently successfully developed for resolving the structure of a G protein receptor (Rasmussen, S. G. et al. Crystal structure of the beta2 adrenergic receptor-Gs protein complex. *Nature* 477, 549-555 (2011) ([26])), has a relatively low impact on the activity of BmrA up to 1 mM but reduces it to 25% at 10 mM, a concentration required to solubilize the protein. DDM, very widely used in the field, induces the same effects, reducing the ATPase activity of BmrA from 50 to 15% at the concentrations which enable the extraction thereof, beyond 5 mM. FA3, corresponding to 1 dimaltoside coupled to a steroid, which has recently been developed (Lee, S. C. et al. (2013) ([9])), produces the same effect, inactivating 75% and 80% of the ATPase activity of BmrA at the concentrations which extract the protein.

The most effective compounds are grouped together in series 3.7, the best of which are 3.7[b,c,e,g,j,l]. These extract BmrA while maintaining (3.7j,l), or increasing by 1.5× (3.7b,c,g) or 2× (3.7e), the ATPase activity of the protein. It should be noted that this increase in activity is a characteristic of ABC transporters, the basal activity of which can be multiplied up to 2.5 times in the presence of solutes; it reflects a perfect functional state. The compounds 3.7b and 3.7c share the same design, including a saccharide coupled to the molecule via a triazole, 2 carboxylic functions and a C11 and C13 aliphatic chain. The compounds 3.7e and 3.7g are a variant of 3.7c with either a maltoside or a PEGylated chain in the place of the saccharide.

Figure 9:
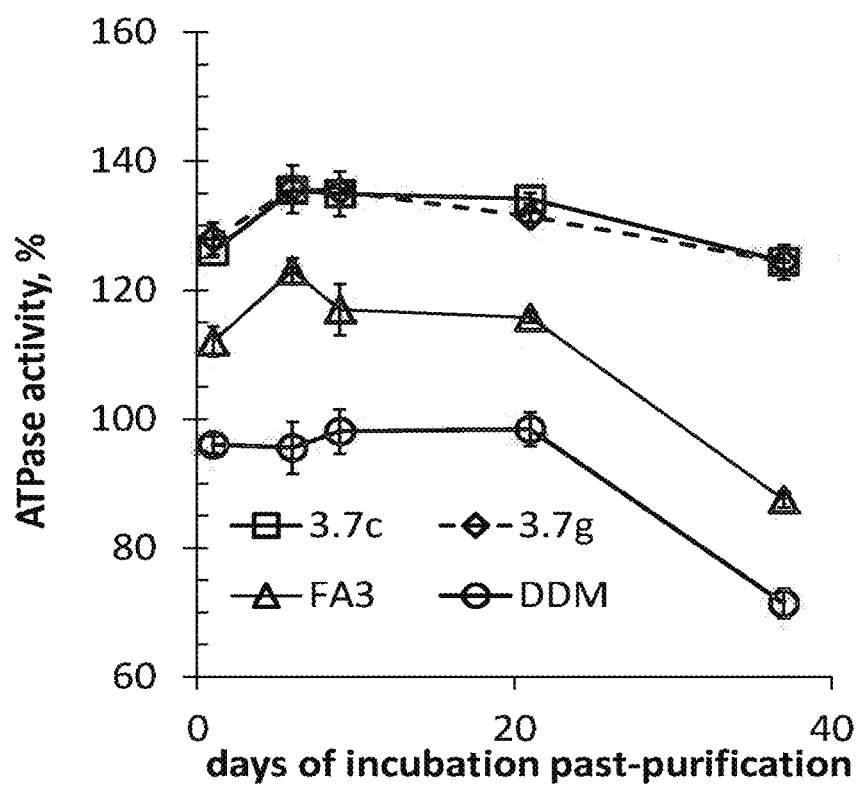
FIG. 9 depicts the stability over time of BmrA purified in DDM (points represented by circles) and with compounds of the invention added thereto (3.7c, points represented by squares, and 3.7g, points represented by diamonds) or FA3 (points represented by triangles) added thereto. The ATPase activity (%) is measured as a function of the number of days of incubation post-purification, as explained in example 13.

Example 13: Study of the Stability Over Time of the Membrane Proteins in the Presence of the Compounds of the Invention Two of the best compounds of the invention originating from the previous test, 3.7c and 3.7g, were evaluated for their ability to stabilize an active form of BmrA over a very long period of time, after purification and storage at 4° C. These 2 detergents were compared to DDM, which is very widely used for these purification steps, and also FA3, which was recently developed and is highly promising in terms of functional stability (Lee, S. C. et al. (2013) ([9])). In order to enable their comparison, the detergents were added to a solution of BmrA purified in DDM, subsequently stored at 4° C. for 40 days. The ATPase activity of BmrA was measured over time, as illustrated in FIG. 9.

Procedure. BmrA produced and enriched in the plasma membrane of *E. coli* C41 DE3 is prepared as described previously (Matar-Merheb, R. et al. ([11])). Twenty milligrams of this membrane fraction are diluted at 4° C. to 1 g/l in 100 mM NaPi pH 8.0, 15% glycerol, 100 mM NaCl, 10 mM imidazole, 1 mM DTT. The suspension has protease inhibitors (Roche, 1 tablet/50 ml) and benzonase (Sigma, 30 U/ml) added to it. The membrane proteins are subsequently extracted by adding 1% DDM (20 mM), for 1 h at 4° C. The solution is centrifuged for 1 h at 100 000×g, 4° C. (Optima XPN-80, 50.2Ti). The supernatant is loaded at 2 ml/min on a 5 ml Ni-NTA resin (GE healthcare, HiTrap chelating HP) equilibrated in buffer A, 100 mM NaPi pH 8.0, 10% glycerol, 100 mM NaCl, 10 mM imidazole, 0.05% DDM (1 mM, 5×CMC). The resin is washed a first time with 25 ml of buffer A, then a second time with 25 ml of buffer B (=A with 500 mM NaCl and 15 mM imidazole) and finally a third time with 20 ml of buffer A. BmrA is eluted with a gradient of buffer A and buffer C (100 mM NaPi, 10% glycerol, 100 mM NaCl, 250 mM imidazole, 0.05% DDM (1 mM, 5×CMC)) spread over 10 ml and collected by 1 ml fractions at 3 ml/min. The fractions of the peak are combined (3 ml) and the mixture is dialyzed in tubing with a cut-off of 12-14000 daltons against 400 ml of cold buffer D (50 mM Hepes-HCl, pH 8.0), 10% glycerol, 100 mM NaCl, 0.05% DDM (1 mM, 5×CMC) for 2 h 30 min at 4° C., then against 600 ml under the same conditions overnight. The protein content (0.8 g/L) of the dialysate is quantified by assaying with bicinchoninic acid, Smith, P. K. et al. Measurement of protein using bicinchoninic acid. *Analytical Biochemistry* 150, 76-85 (1985) ([27])). The solution is separated into 4 fractions diluted to 0.2 g/l of proteins with buffer A without imidazole and DDM. The final [DDM] is 0.25 mM. Each aliquot has 0.087 mM of DDM, FA3, 3.7c or 3.7g added to it and is stored at 4° C. for 40 days. The vanadate-sensitive ATPase activity, Centeno, F. et al. ([25]) is measured at the times indicated in FIG. 9 in duplicate.

Results. As shown in FIG. 9, once purified and in the presence of a low concentration of detergent, BmrA is stable for at least 20 days at 4° C. Beyond this, it loses activity when it is only in the presence of DDM or has FA3 added. These 2 detergents are therefore not able to stabilize a membrane protein such as BmrA in the long term. On the other hand, the addition of 3.7c or 3.7g under identical conditions makes it possible to go beyond 20 days, stabilizing BmrA for at least twice as long, 40 days. These 2 compounds therefore demonstrate a noteworthy property of long-term stabilization, the best reported to date for a membrane protein.

Figure 10:
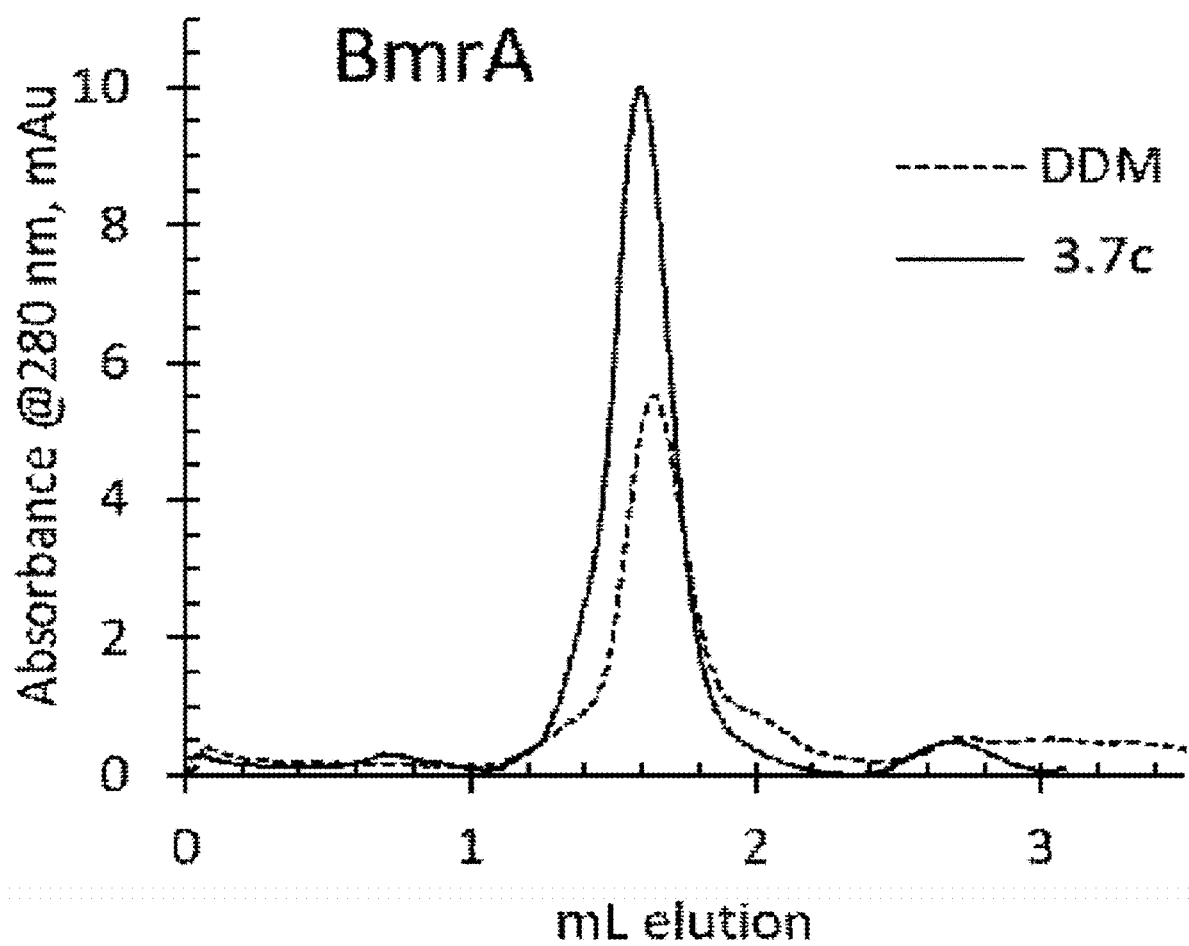
FIG. 10 shows the separation by exclusion chromatography, on Superdex S200 5/150 column, of the ABC membrane protein BmrA, either in the presence of DDM (dashed line) or of the compound of the invention 3.7c (solid line). The membrane fraction was extracted and purified in DDM by Ni-NTA metal affinity and Superdex 200 size exclusion, before being reloaded on Ni-NTA in order to exchange the DDM either with itself or with the compound 3.7c. Each pool was subsequently loaded onto a 3 ml Superdex S200 5/150 size exclusion column and eluted in the presence of 2 CMC of the same detergent, as indicated. The proteins are detected by absorbance at 280 nm.

Example 14: Behavior in Solution of the Membrane Proteins in the Presence of the Compounds of the Invention The capacity of the compounds of the invention to maintain the membrane proteins in a native state was exemplified with the compound 3.7c of the invention, monitored by size exclusion chromatography and compared to the reference detergent DDM. The results are shown in FIG. 10.

Procedure: BmrA was extracted in DDM and purified by Ni-NTA affinity chromatography as described in example 13, then loaded onto a Superdex 200 10/300 size exclusion column and eluted with 50 mM Hepes-HCl pH 8.0, 100 mM NaCl, 0.4 mM DDM (2×CMC). The fractions containing BmrA were pooled and separated into several aliquots (~100 µg) kept at 4° C. One aliquot was subsequently reloaded onto an affinity column containing 1 ml of resin. The DDM was then exchanged against 10 volumes of Hepes-NaCl buffer containing either 2 CMC of DDM (control experiment) or 2 CMC of compound 3.7c (2 mM). BmrA was subsequently eluted in the respective buffers with 100 mM of imidazole added. The fractions containing the proteins were combined and concentrated on 50 kDa amicon (regenerated cellulose) to 50 µl, and were then deposited on a 3 ml Superdex 200 5/150 size exclusion column, equilibrated in 50 mM Hepes-HCl pH 8.0, 100 mM NaCl, and 2 CMC of DDM (0.4 mM) or 3.7c (2 mM). The elution was subsequently carried out at 0.3 ml/min in the respective buffers and the BmrA detected at 280 nm.

Results. As shown in FIG. 10, once the initial detergent (DDM) has been exchanged either with itself or with the compound 3.7c, BmrA has an equivalent behavior in solution, eluting at ~1.6 ml. The exchange of DDM with 3.7c has therefore not modified its dimeric state in solution and does not lead either to its aggregation, which would be reflected by a peak with a maximum at around 1.2 ml (octamer) or 1.4 ml (tetramer), or to its dissociation, visible by a peak at 1.8 ml (monomer). Consequently, the compound of the invention 3.7c conserves the native oligomerization state of the membrane protein.

Example 15: Gain in Thermal Stability of the Membrane Proteins in the Presence of the Compounds of the Invention We studied the stability of membrane proteins in relation to temperature in the presence or in the absence of compounds of the invention (FIG. 12B-E), an experiment which makes it possible to evaluate the capacity of the detergents to maintain the molecular cohesion of a protein despite the agitation caused by the temperature. We tested them on BmrA (panels A, B) according to the procedure of Ashok et al. (Y. Ashok, R. Nanekar, V.-P. Jaakola, Protein Eng. Des. Sel. 2015, 28, 539-542 ([34]). We compared the compounds of the invention with DDM as standard and two recently designed detergents, LMNG (Chae et al., ([6])) and FA3 (Lee et al., ([9])), which exhibit properties of stabilization under these conditions.

Procedure. Based on Y. Ashok et al. ([34]). The membranes of BmrA (2g proteins/l) were solubilized with 0.5% (~10 mM) of DDM and with or without 1 mM of 3.7d, 3.7c, 3.7b, 3.7a, 3.7i, 3.7k, 3.7f, 3.7e, DDM, LMNG or FA3 in a final volume of 2 ml, for 2 h at 4° C. The solubilized fractions were subsequently clarified by centrifugation at 100 000×g for 1 h at 4° C. The supernatants were subsequently aliquoted per 50 µl, each subjected to 30 min at a temperature of 25 to 90° C., using a PCR apparatus (PeqSTAR 2× gradient; Peqlab). The tests were subsequently centrifuged for 40 min at 20 000×g and the supernatants were analyzed by SDS-PAGE and Western blot using an anti-His antibody. The relative intensity of the band for BmrA at each temperature was subsequently quantified using the Bio-Rad Image Lab software 4.1. Each test was duplicated. The intensity was subsequently plotted as a function of the temperature then fit by a 3-parameter sigmoidal equation; Sigmaplot v12.

Figure 11:
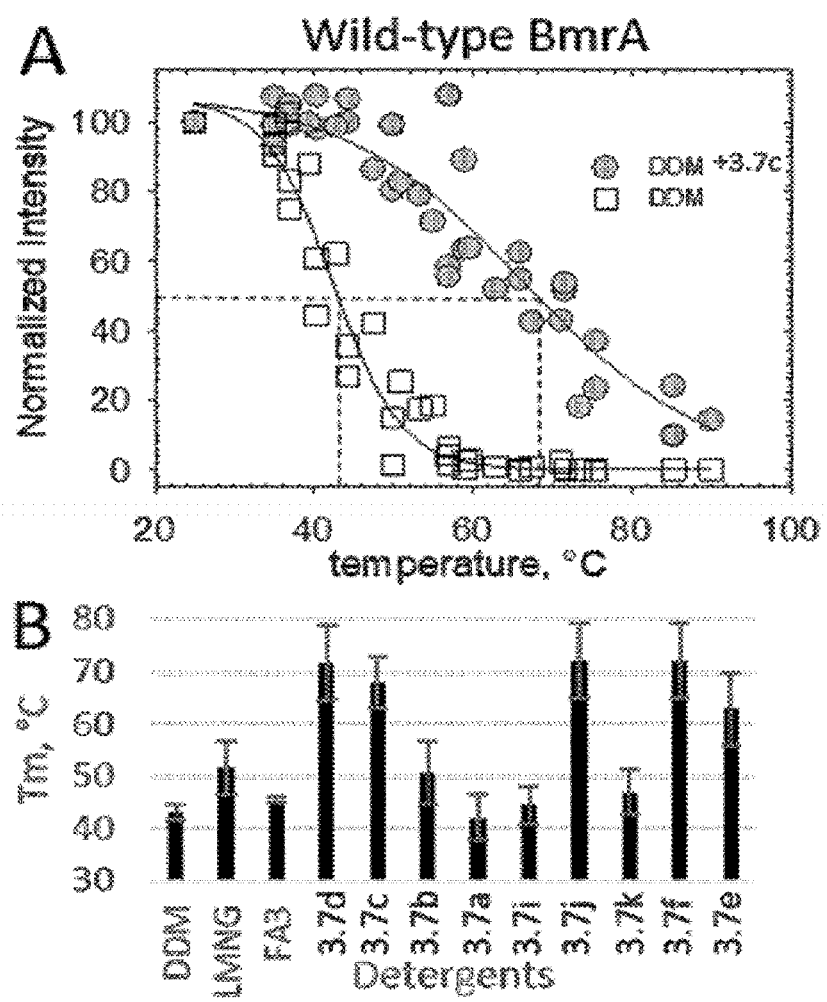
FIG. 11 represents the thermal stability of the membrane protein BmrA in the presence of compounds of the invention. A. Thermostabilization of the BmrA by detergents and compounds of the invention (from left to right: DDM, LMNG, 3.7d, 3.7c, 3.7b, 3.7a, 3.7i, 3.7j, 3.7k, 3.7f and 3.7e. The membrane fractions were extracted with 10 mM DDM with or without 1 mM detergents and compounds of the invention, clarified and subjected for 30 min to the temperatures indicated, followed by centrifugation and SDS-PAGE and Western blot of the supernatants to quantify the remaining membrane proteins (2-4 experiments). B: examples with DDM and 3.7c.

A complete experiment is presented in panel A of FIG. 11 for each protein fraction incubated with 3.7c, making it possible to estimate the apparent melting points, Tm, at which 50% of BmrA remains in solution (dashed lines). As indicated, the compounds of the invention 3.7d, 3.7c, 3.7j, 3.7f and 3.7e induce a temperature shift of 20 to 29° C. for BmrA, while the others did not produce a marked change. A clear effect was observed regarding the hydrophobic component, the largest being the best. It should be noted that this gain in thermal stability is equivalent to that obtained previously by introducing 17 mutations into a fusion protein $A_{2A}R$ with a C-terminal truncation of 96 residues (Magnani et al., ([32])). This result places the compounds of the invention at the forefront of the very small series of stabilizing detergents such as LMNG (Chae et al., ([6])), FA3 (Lee et al., ([9])) and norbornane-based maltosides (NBM) recently published (M. Das, Y. Du, O. Ribeiro, P. Hariharan, J. S. Mortensen, D. Patra, G. Skiniotis, C. J. Loland, L. Guan, B. K. Kobilka, et al., J. Am. Chem. Soc. 2017, 139, 3072-3081, ([35])) which are capable of generating an increase of more than 1 log Tm.

REFERENCE LIST

1. Israelachvili, J. N., Mitchell, D. J. & Ninham, B. W. Theory of self-assembly of lipid bilayers and vesicles. *Biochimica et Biophysica Acta (BBA)—Biomembranes* 470, 185-201 (1977).
2. Overington, J. P., Al-Lazikani, B. & Hopkins, A. L. How many drug targets are there? *Nat Rev Drug Discov* 5, 993-996 (2006).
3. Mason, J. S., Bortolato, A., Congreve, M. & Marshall, F. H. New insights from structural biology into the drugability of G protein-coupled receptors. *Trends in Pharmacological Sciences* 33, 249-260, doi:10.1016/j.tips.2012.02.005 (2012).
4. Schaffhausen, J. Advances in structure-based drug design. *Trends in Pharmacological Sciences* 33, 223, doi:10.1016/j.tips.2012.03.011 (2012).
5. Shoichet, B. K. & Kobilka, B. K. Structure-based drug screening for G-protein-coupled receptors. *Trends in Pharmacological Sciences* 33, 268-272, doi:10.1016/j.tips.2012.03.007 (2012).

6. Chae, P. S. et al. Maltose-neopentyl glycol (MNG) amphiphiles for solublization, stabilization and crystallization of membrane proteins. *Nat Meth* 7, 1003-1008, doi:http://www.nature.com/nmeth/journal/vaop/ncurrent/abs/nmeth.1526.html#supplementary-information (2010).
7. Chae, P. S. et at Tandem Facial Amphiphiles for Membrane Protein Stabilization. *Journal of the American Chemical Society* 132, 16750-16752, doi:10.1021/ja1072959 (2010).
8. Zhang, Q. et al. Designing Facial Amphiphiles for the Stabilization of Integral Membrane Proteins. *Angewandte Chemie International Edition* 46, 7023-7025 (2007).
9. Lee, S. C. et al. Steroid-based facial amphiphiles for stabilization and crystallization of membrane proteins. *Proceedings of the National Academy of Sciences of the United States of America* 110, E1203-1211, doi:10.1073/pnas.1221442110 (2013).
10. Suwinska, K. et al. Tri-Anionic Calix[4]arene Monoalkyl Derivatives: Synthesis; Solid-State Structures and Self-Assembly Properties. *New Journal of Chemistry* 32, 1988-1998, doi:10.1039/b806342g (2008).
11 Matar-Merheb, R. et al. Structuring detergents for extracting and stabilizing functional membrane proteins. *PLoS One* 6, e18036, doi:10.1371/journal.pone.0018036 (2011).
12. von Heijne, G. The distribution of positively charged residues in bacterial inner membrane proteins correlates with the trans-membrane topology. *Embo J* 5, 3021-3027 (1986).
13. Nilsson, J., Persson, B. & von Heijne, G. Comparative analysis of amino acid distributions in integral membrane proteins from 107 genomes. *Proteins: Structure, Function, and Bioinformatics* 60, 606-616, doi:10.1002/prot.20583 (2005).
14. von Heijne, G. Membrane-protein topology. *Nat Rev Mol Cell Biol* 7, 909-918 (2006).
15. Corzana, F. et al. New Insights into α-GalNAc-Ser Motif: Influence of Hydrogen Bonding versus Solvent Interactions on the Preferred Conformation. *Journal of the American Chemical Society* 128, 14640-14648, doi: 10.1021/ja064539u (2006).
16. Christensen, C. A. & Meldal, M. Efficient solid-phase synthesis of peptide-based phosphine ligands: towards combinatorial libraries of selective transition metal catalysts. *Chemistry* 11, 4121-4131, doi:10.1002/chem.200500105 (2005).
17. Boyere, C., Broze, G., Blecker, C., Jerome, C. & Debuigne, A. Monocatenary, branched, double-headed, and bolaform surface active carbohydrate esters via photochemical thiol-ene/-yne reactions. *Carbohydr Res* 380, 29-36, doi:10.1016/j.carres.2013.07.003 (2013).
18. Munteanu, M., Choi, S. & Ritter, H. Cyclodextrin Methacrylate via Microwave-Assisted Click Reaction. *Macromolecules* 41, 9619-9623, doi:10.1021/ma8018975 (2008).
19. Ward, A. B. et al. Structures of P-glycoprotein reveal its conformational flexibility and an epitope on the nucleotide-binding domain. *Proceedings of the National Academy of Sciences of the United States of America* 110, 13386-13391, doi:10.1073/pnas.1309275110 (2013).
20. Martinez, L. et al. Understanding polyspecificity within the substrate-binding cavity of the human multidrug resistance P-glycoprotein. *FEBS Journal* 281, 673-682, doi: 10.1111/febs.12613 (2014).
21. Seeger, M. A. et al. Structural asymmetry of AcrB trimer suggests a peristaltic pump mechanism. *Science* 313, 1295-1298, doi:10.1126/science.1131542 (2006).
22. Chattopadhyay, A. & London, E. Fluorimetric determination of critical micelle concentration avoiding interference from detergent charge. *Anal Biochem* 139, 408-412 (1984).
23. Chaptal, V. et al. Quantification of detergents complexed with membrane proteins. *Scientific Reports* 8; 7:41751 (2017).
24. Psakis, G., Polaczek, J. & Essen, L.-O. AcrB et al.: Obstinate contaminants in a picogram scale. One more bottleneck in the membrane protein structure pipeline. *Journal of Structural Biology* 166, 107-111, doi: http://dx.doi.org/10.1016/j.jsb.2008.12.007 (2009).
25. Centeno, F. et al. Expression of the sarcoplasmic reticulum Ca(2+)-ATPase in yeast. *FEBS Left* 354, 117-122 (1994).
26. Rasmussen, S. G. et al. Crystal structure of the beta2 adrenergic receptor-Gs protein complex. *Nature* 477, 549-555, doi:10.1038/nature10361 (2011).
27. Smith, P. K. et al. Measurement of protein using bicinchoninic acid. *Analytical Biochemistry* 150, 76-85, doi: http://dx.doi.org/10.1016/0003-2697(85) 90442-7 (1985).
28. WO2009144419.
29. WO02090533.
30. Baiceanu E et al.: "2-Indolylmethylenebenzofuranones as first effective inhibitors of ABCC2", Eur J Med Chem. 2016 Oct. 21; 122:408-18.
31. B. Wiseman, A. Kilburg, V. Chaptal, G. C. Reyes-Mejia, J. Sarwan, P. Faison, J.-M. Jault, PLoS One 2014, 9, e114864.
32. F. Magnani, Y. Shibata, M. J. Serrano-Vega, C. G. Tate, Proc. Natl. Acad. Sci. USA 2008, 105, 10744-9.
33. M. J. Serrano-Vega, F. Magnani, Y. Shibata, C. G. Tate, Proc. Natl. Acad. Sci. USA 2008, 105, 877-882.
34. Y. Ashok, R. Nanekar, V.-P. Jaakola, Protein Eng. Des. Sel. 2015, 28, 539-542.
35. M. Das, Y. Du, O. Ribeiro, P. Hariharan, J. S. Mortensen, D. Patra, G. Skiniotis, C. J. Loland, L. Guan, B. K. Kobilka, et al., J. Am. Chem. Soc. 2017, 139, 3072-3081.

The invention claimed is:

1. A compound or a pharmaceutically acceptable salt thereof, chosen from:

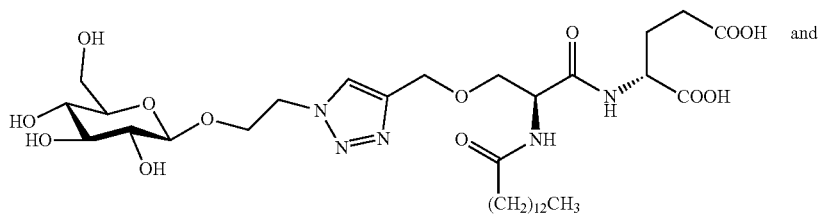

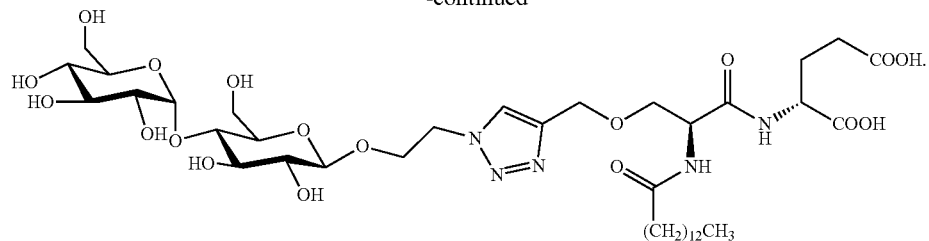

2. A process for extracting membrane proteins, comprising bringing an aqueous solution of membrane proteins associated with a biological membrane into contact with at least one compound or a pharmaceutically acceptable salt thereof chosen from:

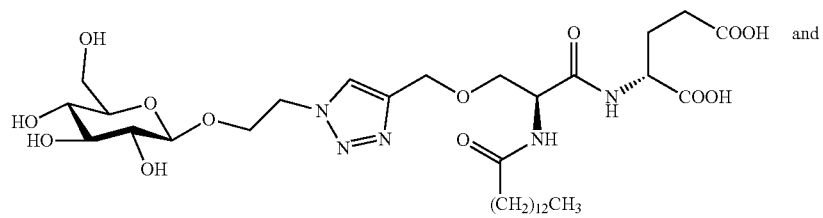

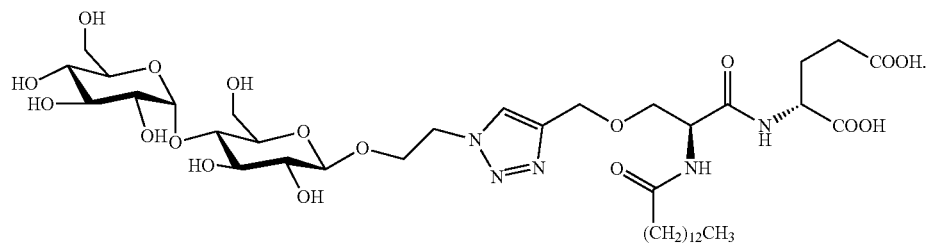

3. The process according to claim 2, wherein the membrane protein is present in a biological membrane fraction originating from a prokaryotic or eukaryotic organism.

4. The process according to claim 2, wherein the membrane protein is a transport protein.

5. The process according to claim 4, wherein the transport protein is an ABC transporter selected from the group consisting of P-glycoproteins (Pgp/ABCB1), MRP1/ABCC1, MRP2/ABCC2, BCRP/ABCG2 and BmrA.

6. The process according to claim 2, wherein the bringing of an aqueous solution comprising the membrane protein to be extracted into contact with the at least one of the compounds or a pharmaceutically acceptable salt thereof is carried out at a pH ranging from 5.5 to 10.

7. A process for stabilizing membrane proteins in solution in an aqueous solution, comprising bringing an aqueous solution of an extracted membrane protein into contact with at least one compound or a pharmaceutically acceptable salt thereof chosen from:

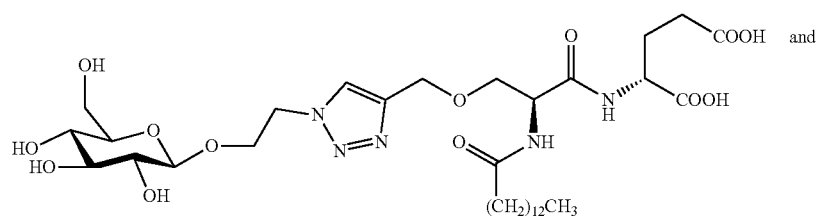

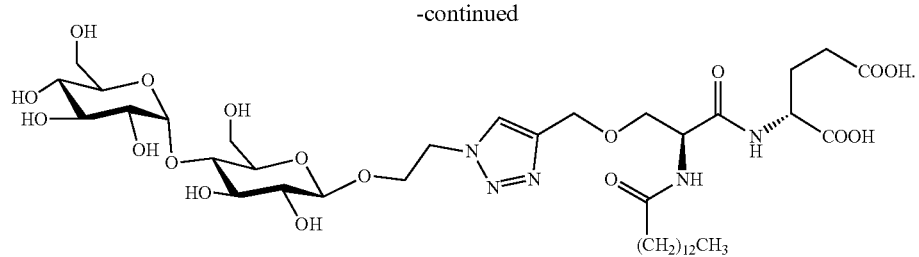

8. The process according to claim 7, wherein the membrane proteins are extracted by bringing an aqueous solution of membrane proteins associated with a biological membrane into contact with at least one of the compounds or a pharmaceutically acceptable salt thereof.

9. The process according to claim 7, wherein said protein in solution is stabilized at a temperature of from 0° C. to 10° C. for a duration of greater than 1 day.

10. The process according to claim 7, wherein the membrane proteins are extracted by detergent.

* * * * *